(12) United States Patent
Jitsuoka et al.

(10) Patent No.: US 8,158,791 B2
(45) Date of Patent: Apr. 17, 2012

(54) AZA-SUBSTITUTED SPIRO DERIVATIVES

(75) Inventors: Makoto Jitsuoka, Moriya (JP); Nagaaki Sato, Tsukuba (JP); Daisuke Tsukahara, Tsukuba (JP)

(73) Assignee: MSD K.K., Chiyoda-Ku (JP)

( * ) Notice: Subject to any disclaimer, the term of this patent is extended or adjusted under 35 U.S.C. 154(b) by 726 days.

(21) Appl. No.: 12/084,817

(22) PCT Filed: Nov. 10, 2006

(86) PCT No.: PCT/JP2006/322911
§ 371 (c)(1),
(2), (4) Date: May 8, 2008

(87) PCT Pub. No.: WO2007/055418
PCT Pub. Date: May 18, 2007

(65) Prior Publication Data
US 2009/0258871 A1    Oct. 15, 2009

(30) Foreign Application Priority Data

Nov. 10, 2005 (JP) ................................ 2005-325808
Mar. 7, 2006 (JP) ................................ 2006-060814

(51) Int. Cl.
A61K 31/44 (2006.01)
A61K 31/34 (2006.01)
A61K 31/335 (2006.01)
C07D 221/00 (2006.01)

(52) U.S. Cl. ............................ 546/15; 514/278; 514/462
(58) Field of Classification Search .................. 514/278, 514/462; 546/15
See application file for complete search history.

(56) References Cited

U.S. PATENT DOCUMENTS

| 6,117,880 | A | 9/2000 | Guo et al. |
| 6,191,160 | B1 | 2/2001 | Gao et al. |
| 6,326,375 | B1 | 12/2001 | Fukami et al. |
| 6,803,372 | B2 | 10/2004 | Fukami et al. |
| 6,906,060 | B2 | 6/2005 | Peschke et al. |
| 7,304,072 | B2 | 12/2007 | Fukami et al. |
| 7,442,791 | B2 | 10/2008 | Ackermann et al. |
| 7,632,857 | B2 | 12/2009 | Hornback et al. |
| 8,008,301 | B2 | 8/2011 | Beavers et al. |
| 2002/0188124 | A1* | 12/2002 | Fukami et al. ............... 544/230 |
| 2004/0110746 | A1 | 6/2004 | Apodaca et al. |
| 2004/0259890 | A1 | 12/2004 | Fukami et al. |
| 2005/0032820 | A1 | 2/2005 | Fukami et al. |
| 2005/0065210 | A1 | 3/2005 | Ackermann et al. |
| 2006/0111380 | A1 | 5/2006 | Otake et al. |
| 2007/0105901 | A1 | 5/2007 | Ohtake et al. |
| 2007/0208024 | A1 | 9/2007 | Beavers et al. |
| 2008/0171753 | A1* | 7/2008 | Jitsuoka et al. ........... 514/254.11 |

FOREIGN PATENT DOCUMENTS

| EP | 1415986 | 8/2002 |
| EP | 1415986 | 5/2004 |
| EP | 1566384 | 8/2005 |
| EP | 1795527 | 6/2007 |
| JP | 2005529942 | 6/2005 |
| WO | WO9922735 | 5/1999 |
| WO | WO0027845 | 5/2000 |
| WO | WO0114376 | 3/2001 |
| WO | WO02076443 | 10/2002 |
| WO | WO03104235 | 12/2003 |
| WO | WO2004037801 | 5/2004 |
| WO | WO2005028427 | 3/2005 |
| WO | 2005063745 | 7/2005 |
| WO | WO 2005/063745 | 7/2005 |
| WO | WO2005097740 | 10/2005 |

OTHER PUBLICATIONS

C. G. Wermuth et al., "Ring Transformations", The Practice of Medicinal Chemistry, pp. 240-257, Chapter 14, 1996.
European Search Report for BY065Y, Nov. 24, 2009.
International Preliminary Report on Patentability for WO2007/055418, May 14, 2008.

* cited by examiner

Primary Examiner — Barbara P Badio
Assistant Examiner — Sara E Townsley
(74) Attorney, Agent, or Firm — J. Eric Thies; Gerald M. Devlin

(57) ABSTRACT

A compound of the following formula (I) or its pharmaceutically-acceptable salt is provided:

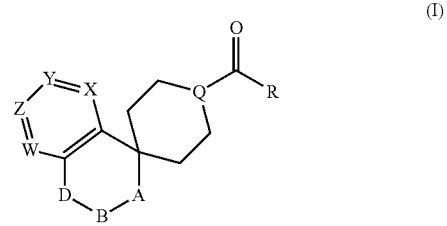

(I)

[wherein X, Y, Z and W each independently represent a methine group or a nitrogen atom, provided that a case where all of X, Y, Z and W are methine group; A represents —O— or the like, B represents —C(O)— or the like, D represent —(CH$_2$)m2-, —O— or the like, and m2 represents 0 or 1; Q represents a methine group or a nitrogen atom; and R represents a group represented by the following formula (II-1) (wherein R$^6$, R$^7$ and R$^8$ independently represent a lower alkyl group or the like].

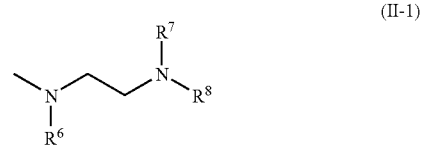

(II-1)

20 Claims, No Drawings

AZA-SUBSTITUTED SPIRO DERIVATIVES

CROSS REFERENCE TO RELATED APPLICATIONS

This application is a U.S. National Phase application under 35 U.S.C. §371 of PCT Application No. PCT/JP2006/322911, filed Nov. 10, 2006, which claims priority under 35 U.S.C. §119 from JP Application Nos. JP2005-325808, filed Nov. 10, 2005 and JP2006-60814 filed Mar. 7, 2006.

TECHNICAL FIELD

The present invention relates to aza-substituted spiro derivatives.

BACKGROUND ART

It has been known that, in organisms such as typically mammals, histamine which is a physiologically-active endogenous factor functions as a neurotransmitter and has extensive pharmacological activities (for example, see *Life Science*, Vol. 17, p. 503 (1975)).

Immunohistochemical studies have made it clear that a histamine-agonistic (producing) cell body exists in the nodal papillary nucleus in a posterior hypothalamic region and that histamine nerve fibers project in an extremely broad range in the brain, which supports various pharmacological effects of histamine (for example, see *Journal of Comparative Neurology*, Vol. 273, p. 283). The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see *Progress in Neurobiology*, Vol. 63, p. 637 (2001)).

The existence of projection to the brain region that relates to vigilance sustenance, for example, to cerebral cortex suggests the role in control of vigilance or vigilance-sleep cycle. The existence of projection to many peripheral structures such as hippocampus and amygdaloid complex suggests the role in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, histamine-H3 receptor, has been shown by various pharmacological and physiological studies (for example, see *Trends in Pharmacological Science*, Vol. 8, p. 24 (1987)); and recently, human and rodent histamine-H3 receptor genes have been identified and their existence has been made clear (for example, see *Molecular Pharmacology*, Vol. 55, p. 1101 (1999)).

It is suggested that histamine-H3 receptor exists in the presynaptic membrane of central or peripheral neurocytes and functions as a self-receptor, therefore controlling the release of histamine and controlling the release of other neurotransmitters. Specifically, it is reported that a histamine-H3 receptor agonist, or its antagonist or inverse-agonist controls the release of histamine, noradrenaline, serotonin, acetylcholine or dopamine from nerve ending. For example, the release of these neurotransmitters is inhibited by an agonist such as (R)-(α)-methylhistamine, and is promoted by an antagonist or inverse-agonist such as thioperamide (for example, see *Trends in Pharmacological Science*, Vol. 19, p. 177 (1998)).

WO99/22735 disclose the compounds similar to this invention. The compounds disclosed in this publication have a carbonyl group corresponding to R substituent in the present invention, however the compound of the present invention doesn't have a carbonyl group in R substituent. So this publication is different from the present invention. Furthermore the usage of the reference is different from that of the present invention, because the invention of the reference is related to Somatostatin agonist.

DISCLOSURE OF THE INVENTION

An object of the invention is to provide a novel substance having a histamine-H3 receptor antagonistic effect (an effect of inhibiting histamine from binding to a histamine-H3 receptor) or a histamine-H3 receptor inverse-agonistic effect (an effect of inhibiting the homeostatic activity that a histamine-H3 receptor has), or that is, a novel substance that acts as a histamine-H3 receptor antagonist or inverse agonist in living bodies.

We, the present inventors provide compounds or salts of the formula (I) for attaining the above object.

(1) A compound of the following formula (I) or its pharmaceutically-acceptable salt:

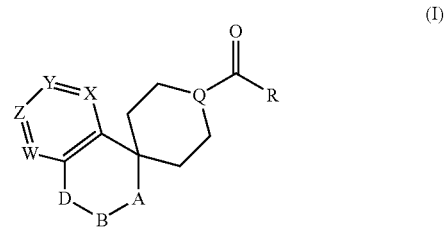

[wherein

X, Y, Z and W each independently represent a methine group optionally having substituents selected from a substituent group α, or a nitrogen atom (provided that a case where X, Y, Z and W all represent a methine group optionally having substituents selected from a substituent group α is excluded);

A represents —$(C(R^3)(R^4))_{m1}$—, —C(O)—, —O— or —$N(R^5)$—;

B represents —$N(SO_2R^1)$—, —$N(COR^2)$—, —$N(R^{50})$—, —O— or —C(O)—;

D represents —$(C(R^{30})(R^{40}))_{m2}$—, —O—, —$N(R^{51})$— or —C(O)—;

m1 and m2 each independently indicate 0 or 1;

$R^1$, $R^2$ and $R^5$ each independently represent a hydrogen atom, a lower alkyl group, an aralkyl group or an aryl group;

$R^3$, $R^4$, $R^{30}$ and $R^{40}$ each independently represent a hydrogen atom, a hydroxyl group, a lower alkyl group, an aralkyl group or an aryl group;

$R^{50}$ and $R^{51}$ each independently represent a hydrogen atom or a lower alkyl group;

Q represents a methine group or a nitrogen atom;

R represents a group of the following formula (II)

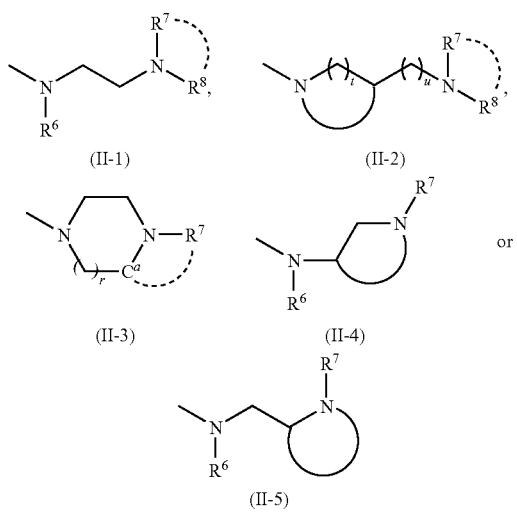

(wherein $R^6$ represents a hydrogen atom or a lower alkyl group; $R^7$ and $R^8$ each independently represent a lower alkyl group, a cycloalkyl group, an aralkyl group, a heteroarylalkyl group; or $R^7$ and $R^8$ together with the nitrogen atom to which they bond form a 4- to 8-membered nitrogen-containing aliphatic heterocyclic group; or $R^7$ forms, taken together with $C^a$ and the nitrogen atom to which it bonds, a 4- to 8-membered nitrogen-containing aliphatic heterocyclic group; a group of;

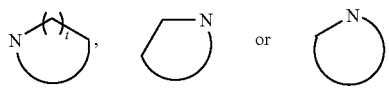

in the formulae (II-2), (II-4) and (II-5) represents a 4- to 8-membered nitrogen-containing aliphatic heterocyclic group; r indicates 0 to 2; t indicates 0 or 1; u indicates 0 or 1; but t+u=1); and any hydrogen atom in the formula (II) may have a substituent selected from a group consisting of a lower alkyl group (the lower alkyl group may be substituted with a halogen atom, an oxo group or an alkoxy group), a cycloalkyl group, a hydroxy group, an alkoxy group (the alkoxy group may be substituted with a halogen atom) and a halogen atom], and wherein, the substituent group a includes the following: Substituent group α: a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group (the group may be substituted with a halogen atom or a hydroxyl group), an amino group, a cyano group, a mono- or di-lower alkylamino group, a formyl group, an alkanoyl group, a mono- or di-lower alkylcarbamoyl group, an arylcarbamoyl group, a heteroarylcarbamoyl group, an arylalkylcarbamoyl group, a heteroarylalkylcarbamoyl group, a lower alkylsulfonyl group, a lower alkylthio group, an aryloxycarbonylamino group, an arylalkyloxycarbonylamino group, an alkoxycarbonylamino group, an alkanoylamino group, an arylcarbonylamino group, an arylalkylcarbonyl group, a lower alkylsulfonylamino group, an arylsulfonylamino group, a lower alkylsulfamoyl group, an arylsulfamoyl group, an aryl group, an aryloxy group, a heteroaryl group and an aralkyl group.

(2) The compound or its pharmaceutically-acceptable salt as above (1), wherein 1 or 2 of X, Y, Z and W is nitrogen atom.

(3) The compound or its pharmaceutically-acceptable salt as above (1), wherein 1 of X, Y, Z and W is a nitrogen atom.

(4) The compound or its pharmaceutically-acceptable salt as above (1), wherein Q is a methine group.

(5) The compound or its pharmaceutically-acceptable salt as above (1), wherein A is —O— or —N($R^5$)—, B is —C(O)—, D is —(C($R^{30}$)($R^{40}$))$_{m2}$—, and m2 is 0 or 1.

(6) The compound or its pharmaceutically-acceptable salt as above (1), wherein A is —C(O)—, B is —O— or —N($R^{50}$)—, D is —(C($R^{30}$)($R^{40}$))$_{m2}$—, and m2 is 0 or 1.

(7) The compound or its pharmaceutically-acceptable salt as above (1), wherein A is —(C($R^3$)($R^4$))$_{m1}$—, B is —O—, D is —(C($R^{30}$)($R^{40}$))$_{m2}$—, m1 is 0, and m2 is 1.

(8) The compound or its pharmaceutically-acceptable salt as above (1), wherein A is —(C($R^3$)($R^4$))$_{m1}$—, B is —C(O)—, D is —O—, —N($R^{51}$)— or —(C($R^{30}$)($R^{40}$))$_{m2}$—, m1 is 0 or 1, and m2 is 0.

(9) The compound or its pharmaceutically-acceptable salt as above (1), wherein R is formula (II-1), (II-2), (II-3) or (II-4).

(10) The compound or its pharmaceutically-acceptable salt as above (1), wherein R is formula (II-1), (II-4) or (II-5), and $R^6$ is a lower alkyl group.

(11) The compound or its pharmaceutically-acceptable salt as above (10), wherein R is formula (II-1).

(12) The compound or its pharmaceutically-acceptable salt as above (11), wherein $R^7$ and $R^8$, taken together, form a 4- to 8-membered nitrogen-containing aliphatic heterocyclic group optionally having substituents selected from a group consisting of a lower alkyl group (the lower alkyl group may be substituted with a halogen atom, an oxo group or an alkoxy group), a cycloalkyl group, a hydroxy group, an alkoxy group (the alkoxy group may be substituted with a halogen atom) and a halogen atom.

The compound or its salt of above (1) acts as a histamine-H3 receptor antagonist or inverse-agonist in living bodies. Accordingly, the invention provides a histamine-H3 receptor antagonist or inverse-agonist comprising the compound or its pharmaceutically-acceptable salt of above (1).

Recent studies have shown that a histamine-H3 receptor has extremely high homeostatic activities (activities observed in the absence of an endogenous agonistic factor (e.g., histamine)) in the receptor-expressing cells/tissues or in a membrane fraction derived from the expressing cells/tissues and even in living bodies (for example, see *Nature*, Vol. 408, p. 860). It is reported that these homeostatic activities are inhibited by an inverse-agonist. For example, thioperamide or syproxyfan inhibits the homeostatic self-receptor activity of a histamine-H3 receptor, and, as a result, promotes the release of neurotransmitters (e.g., histamine) from nerve ending.

Regarding rats, a high-level selective inhibitor of histamine synthetase (histidine decarboxylase) inhibits the vigilance of rats, and therefore histamine participates in controlling motive vigilance. Regarding cats, administration of (R)-(α)-methylhistamine to cats increases their deep slow-wave sleep (for example, see *Brain Research*, Vol. 523, p. 325 (1990)). Contrary to this, thioperamide dose-dependently increases vigilance, and decreases slow-wave and REM sleep (for example, see *Life Science*, Vol. 48, p. 2397 (1991)). A histamine-H3 receptor antagonist or inverse-agonist, thioperamide or GT-2331 reduces emotional cataplexy and sleep of narcoleptic dogs (for example, see *Brain Research*, Vol. 793, p. 279 (1998)).

These information suggest that the H3 receptor may participate in control of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia). Accordingly, it may be considered that the compounds or their salts of above (1) acting as a histamine-H3 receptor antagonist or inverse-agonist may be effective for prevention and remedy of sleep disorders and various sleep disorder-associated diseases.

In rats, thioperamide or GT-2331 relieves the condition of learning disorder (LD) and attention deficit hyperactivity disorder (ADHD) (for example, see *Life Science*, Vol. 69, p. 469 (2001)). Further in rats, (R)-(α)-methylhistamine lowers their object cognitive and learning effects in the object cognition test and the passive turnout test with them.

On the other hand, in a scopolamine-induced amnesia test, thioperamide dose-dependently relieves amnesia induced by the chemical (for example, see *Pharmacology, Biochemistry and Behavior*, Vol. 68, p. 735 (2001)).

These information suggest a possibility that a histamine-H3 receptor antagonist or inverse-agonist may be useful for prevention or remedy of memory/learning disorder and various diseases accompanied by it (e.g., Alzheimer's disease, Parkinson's disease, attention deficit/hyperactivity disorder). Accordingly, it may also be considered that the present compound or its salt may be effective for prevention or remedy of such memory/learning disorder and various diseases accompanied by it.

Regarding rats, administration of histamine to their ventricle inhibits their eating action, therefore suggesting that histamine may participate in control of eating action (for example, see *Journal of Physiology and Pharmacology*, Vol. 49, p. 191 (1998)). In fact, thioperamide dose-dependently inhibits eating action and promotes intracerebral histamine release (for example, see *Behavioral Brain Research*, Vol. 104, p. 147 (1999)).

These information suggest that a histamine H3 receptor may participate in eating action control, further suggesting that a histamine-H3 antagonist or inverse-agonist may be useful for prevention or remedy of metabolic system diseases (metabolic syndromes) such as eating disorder, obesity, diabetes, emaciation, hyperlipemia. Accordingly, it may be considered that the present compound or it salt may be effective also for prevention or remedy of such metabolic system diseases.

In rats, (R)-(α)-methylhistamine dose-dependently lowers their basal diastolic pressure, and its action is antagonized by thioperamide (for example, see *European Journal of Pharmacology*, Vol. 234, p. 129, (1993)).

These information suggest that a histamine-H3 receptor may participate in control of blood pressure, heart beat and cardiac output, further suggesting that a histamine-H3 receptor agonist, antagonist or inverse-agonist may be useful for prevention or remedy of circulatory system diseases such as hypertension and various cardiac disorders. Accordingly, it may be considered that the present compound or it salt may be effective also for prevention or remedy of such circulatory system diseases.

In mice, thioperamide dose-dependently inhibits the spasm induced by electric shock or the epileptoid seizure induced by pentylene tetrazole (PTZ) (for example, see *European Journal of Pharmacology*, Vol. 234, p. 129 (1993) and *Pharmacology, Biochemistry and Behavior*, Vol. 68, p. 735 (2001)).

These information suggest that a histamine-H3 receptor antagonist or inverse-agonist may be useful for prevention or remedy of epilepsy or central spasm. Accordingly, it may be considered that the present compound or it salt may be effective also for prevention or remedy of such epilepsy or central spasm.

Accordingly, the invention further provides a preventive or remedy for metabolic system diseases, circulatory system diseases or nervous system diseases, which contains, as the active ingredient thereof, the present compound or its pharmaceutically-acceptable salt.

The metabolic system diseases are at least one selected from obesity, diabetes, hormone secretion disorder, hyperlipemia, gout and fatty liver.

The circulatory system diseases are at least one selected from stenocardia, acute/congestive cardiac insufficiency, cardiac infarction, coronary arteriosclerosis, hypertension, nephropathy and electrolyte disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

The nervous system diseases are at least one selected from idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia.

The present compound or its pharmaceutically-acceptable salt may be used, as combined with a co-drug. Accordingly, the invention further provides a preventive or remedy for metabolic system diseases, circulator system diseases or nervous system diseases, which contains a present compound or its pharmaceutically-acceptable salt and a co-drug, as the active ingredients thereof. The co-drug includes a remedy for diabetes, a remedy for hyperlipemia, a remedy for hypertension, an anti-obesity drug. Two or more such co-drugs may be used herein, as combined.

The preventive or remedy for such diseases, which the invention provides herein, may comprise the following (i), (ii) and (iii):
(i) a compound or its pharmaceutically-acceptable salt of any one of above (1);
(ii) at least one selected from a group of the following (a) to (g):
(a) a histamine-H3 receptor antagonist or inverse-agonist except (i);
(b) a biguanide,
(c) a PPAR (peroxisome proliferator-activated receptor)-agonist;
(d) insulin,
(e) somatostatin,
(f) an α-glucosidase inhibitor,
(g) an insulin secretion promoter;
(iii) a pharmaceutically-acceptable carrier.

BEST MODE FOR CARRYING OUT THE INVENTION

The meanings of the terms used in this description are described first, and then the compounds of the invention are described.

"Aryl group" includes a hydrocarbon-ring aryl group having from 6 to 14 carbon atoms, for example, a phenyl group, a naphthyl group, a biphenyl group, an anthryl group.

"Heteroaryl group" means a 5- or 6-membered monocyclic heteroaryl group having therein from 1 to 4 hetero atoms selected from an oxygen atom, a sulfur atom and a nitrogen atom, or a bicyclic heteroaryl group of the monocyclic heteroaryl group condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, an quinoxalinyl group, a cinnolinyl group, a benzimidazolyl group, a imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group et al.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group et al.

"Alkoxy group" means a hydroxyl group of which the hydrogen atom is substituted with the above-mentioned lower alkyl group, including, for example, a methoxy group, an ethoxy group, a propoxy group et al.

"Cycloalkyl group" is preferably a cycloalkyl group having from 3 to 9 carbon atoms, including, for example, a cyclopropyl group, a cyclobutyl group, a cyclopentyl group, a cyclohexyl group, a cycloheptyl group, a cyclooctyl group, a cyclononyl group.

"Aralkyl group" means the above-mentioned lower alkyl group having the above-mentioned aryl group, including, for example, a benzyl group, a 1-phenylethyl group, a 2-phenylethyl group, a 1-naphthylmethyl group, a 2-naphthylmethyl group et al.

"Heteroarylalkyl group" means a group formed by the above-mentioned heteroaryl group and the above-mentioned alkyl group bonding to each other, including, example, a furan-3-yl-methyl group, a furan-2-ylmethyl group, a furan-3-ylethyl group, a furan-2-ylethyl group, a furan-3-ylpropyl group, a furan-2-ylpropyl group, a thiophen-3-ylmethyl group, a thiophen-2-ylmethyl group, a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-pyrrol-2-ylpropyl group, a 1H-imidazol-4-ylmethyl group, a 1H-imidazol-2-ylmethyl group, a 1H-imidazol-5-ylmethyl group, a 1H-imidazol-4-ylethyl group, a 1H-imidazol-2-ylethyl group, a 1H-imidazol-5-ylethyl group, a 1H-imidazol-4-ylpropyl group, a 1H-imidazol-2-ylpropyl group, a 1H-imidazol-5-ylpropyl group, a 1H-[1,2,3]triazol-4-ylmethyl group, a 1H-[1,2,3]triazol-5-ylmethyl group, a 1H-[1,2,3]triazol-4-ylethyl group, a 1H-[1,2,3]triazol-5-ylethyl group, a 1H-[1,2,3]triazol-4-ylpropyl group, a 1H-[1,2,3]triazol-5-ylpropyl group, a 1H-[1,2,4]triazol-3-ylmethyl group, a 1H-[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group, a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group, a thiazol-4-ylpropyl group, a thiazol-3-ylpropyl group, a thiazol-2-ylpropyl group, a [1,2,4]thiadiazol-3-ylmethyl group, a [1,2,4]thiadiazol-3-ylethyl group, a [1,2,4]thiadiazol-3-ylpropyl group, a [1,2,4]thiadiazol-5-ylmethyl group, a [1,2,4]thiadiazol-5-ylethyl group, a [1,2,4]thiadiazol-5-ylpropyl group, a [1,3,4]thiadiazol-2-2-ylmethyl group, a [1,3,4]thiadiazol-2-ylethyl group, a [1,3,4]thiadiazol-2-ylpropyl group et al.

"Halogen atom" means, for example, a fluorine atom, a chlorine atom, a bromine atom, an iodine atom.

For further more concretely disclosing the compounds of the formula (I) of the invention, the compounds of the formula (I):

X, Y, Z and W each independently represent a methine group optionally having substituents selected from a substituent group α, or a nitrogen atom.

However, a case where X, Y, Z and W all represent a methine group optionally having substituents selected from a substituent group α is excluded.

Concretely, one or two of X, Y, Z, and W are nitrogen atom, specially one is nitrogen atom is preferable.

Preferable combinations of X, Y, Z, and W are as follow;

X, Z and W are methine groups optionally having substituents, and Y is a nitrogen atom;

X, Y and W are methine groups optionally having substituents, and Z is a nitrogen atom;

X, Y and Z are methine groups optionally having substituents, and W is a nitrogen atom, and more preferably, X, Y and Z are methine groups optionally having substituents, and W is a nitrogen atom;

X, Y and W are methine groups optionally having substituents, and Z is a nitrogen atom, are recommended.

"Methine group optionally having substituents selected from a substituent group α" means an unsubstituted methine group, or a methine group having substituents selected from a substituent group α.

The substituent group α includes a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group (the group may be substituted with a cycloalkyl group, a halogen atom or a hydroxyl group), a cycloalkoxy group (one carbon atom constituting the cycloalkoxy group may be substituted with a nitrogen atom, and the nitrogen atom may be substituted with an alkanoyl group), an amino group, a cyano group, a mono- or di-lower alkylamino group, a formyl group, an alkanoyl group, a mono- or di-lower alkylcarbamoyl group, an arylcarbamoyl group, a heteroarylcarbamoyl group, an arylalkylcarbamoyl group, a heteroarylalkylcarbamoyl group, a lower alkylsulfonyl group, a lower alkylthio group, an aryloxycarbonylamino group, an arylalkyloxycarbonylamino group, an alkoxycarbonylamino group, an alkanoylamino group, an arylcarbonylamino group, an arylalkylcarbonyl group, a lower alkylsulfonylamino group, an arylsulfonylamino group, a lower alkylsulfamoyl group, an arylsulfamoyl group, an aryl group, an aryloxy group, a heteroaryl group, an aralkyl group and an aralkyloxy group.

The halogen atom for the substituent includes, for example, a fluorine atom, a chlorine atom, a bromine atom or an iodine atom.

The lower alkyl group for the substituent includes, for example, a methyl group, an ethyl group, an n-propyl group, an isopropyl group.

The lower alkyl group may be substituted with a halogen atom, a hydroxyl group or an alkoxy group.

The lower alkyl group substituted with a halogen atom includes, for example, a fluoromethyl group, a chloromethyl group, a 2-fluoroethyl group, a 2-chloroethyl group et al.

The lower alkyl group substituted with a hydroxyl group includes, for example, a hydroxymethyl group, a 2-hydroxyethyl group et al.

The cycloalkyl group for the substituent includes, for example, a cyclopropyl group, a cyclobutyl group, a cyclopentyl group, a cyclohexyl group et al.

The cycloalkyl group may be substituted with a halogen atom, a hydroxyl group or an alkoxy group.

The alkoxy group for the substituent includes, for example, a methoxy group, an ethoxy group, an isopropoxy group et al.

The alkoxy group may be substituted with a halogen atom or a hydroxyl group.

The cycloalkyloxy group for the substituent means a group of the above-mentioned cycloalkyl group bonding to an oxygen atom, concretely including, for example, a cyclopropyloxy group, a cyclobutyloxy group, a cyclopentyloxy group, a cyclohexyloxy group et al.

One carbon atom constituting the cycloalkyloxy group may be substituted with a nitrogen atom.

The cycloalkyloxy group in which one carbon atom is substituted with a nitrogen atom is preferably a 4- to 7-membered aliphatic ring, concretely including, for example, an azetidin-3-yloxy group, a pyrrolidin-3-yloxy group, a piperidin-4-yloxy group, a homopiperidin-4-yl group et al.

The nitrogen atom in the 4- to 7-membered nitrogen-containing aliphatic ring may be substituted with an alkanoyl group, a lower alkylsulfonyl group, a diphenylmethyl group, a formyl group or a lower alkoxycarbonyl group.

The lower alkanoyl group includes, for example, an acetyl group, a propionyl group et al.

The lower alkylsulfonyl group means a group of the above-mentioned lower alkyl group bonding to a sulfonyl group, concretely including, for example, a methylsulfonyl group, an ethylsulfonyl group, an isopropylsulfonyl group, a propylsulfonyl group, a butylsulfonyl group et al.

The lower alkoxycarbonyl group means a group of the above-mentioned lower alkoxy group bonding to a carbonyl group, concretely including, for example, a methoxycarbonyl group, an ethoxycarbonyl group, an isopropyloxycarbonyl group et al.

The mono-lower alkylamino group for the substituent means an amino group mono-substituted with the above-mentioned lower alkyl group, including, for example, a methylamino group, an ethylamino group, a propylamino group, an isopropylamino group, a butylamino group, a sec-butylamino group and a tert-butylamino group.

The di-lower alkylamino group for the substituent is an amino group di-substituted with the same or different, above-mentioned lower alkyl groups, including, for example, a dimethylamino group, a diethylamino group, a dipropylamino group, a methylpropylamino group and a diisopropylamino group.

The alkanoyl group for the substituent means a group of the above-mentioned alkyl group bonding to a carbonyl group, including, for example, a methylcarbonyl group, an ethylcarbonyl group, a propylcarbonyl group, an isopropylcarbonyl group et al.

The mono-lower alkylcarbamoyl group for the substituent means a carbamoyl group mono-substituted with the above-mentioned lower alkyl group, including, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group et al.

The di-lower alkylcarbamoyl group for the substituent means a carbamoyl group di-substituted with the same or different, above-mentioned lower alkyl groups. "Di-lower alkylcarbamoyl group" includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group et al.

The arylcarbamoyl group for the substituent means a carbamoyl group with the above-mentioned one or two "aryl groups" bonding thereto, including, for example, a phenylcarbamoyl group, a naphthalene-1-ylcarbamoyl group, a naphthalene-2-ylcarbamoyl group et al.

The heteroarylcarbamoyl group for the substituent means a carbamoyl group with the above-mentioned one or two "heteroaryl groups" bonding thereto, including, for example, a furan-2-ylcarbamoyl group, a furan-3-ylcarbamoyl group, a thiophen-2-ylcarbamoyl group, a thiophen-3-ylcarbamoyl group, a 1H-pyrrol-2-ylcarbamoyl group, a 1H-pyrrol-3-ylcarbamoyl group, a 1H-imidazol-2-ylcarbamoyl group, a 1H-imidazol-4-ylcarbamoyl group, a 3H-imidazol-4-ylcarbamoyl group, a 4H-[1,3,4]triazol-3-ylcarbamoyl group, a 2H-[1,2,4]triazol-3-ylcarbamoyl group, a 1H-[1,2,4]triazol-3-ylcarbamoyl group, a thiazol-2-ylcarbamoyl group, a thiazol-4-ylcarbamoyl group, a thiazol-5-ylcarbamoyl group, a pyridin-2-ylcarbamoyl group, a pyridin-3-ylcarbamoyl group, a pyridin-4-ylcarbamoyl group, a pyrimidine-2-ylcarbamoyl group, a pyrimidine-4-ylcarbamoyl group, a pyrimidine-5-ylcarbamoyl group, a pyridazin-3-ylcarbamoyl group, a pyridazin-4-ylcarbamoyl group, a 2H-pyrazol-3-ylcarbamoyl group, a 1H-pyrazol-4-ylcarbamoyl group, a 1H-pyrazol-3-ylcarbamoyl group, a pyrazin-3-ylcarbamoyl group, a pyrazin-4-ylcarbamoyl group, a quinolin-2-ylcarbamoyl group, a quinolin-3-ylcarbamoyl group, a quinolin-4-ylcarbamoyl group, an isoquinolin-1-ylcarbamoyl group, an isoquinolin-3-ylcarbamoyl group, an isoquinolin-4-ylcarbamoyl group, a quinazolin-2-ylcarbamoyl group, a quinazolin-3-ylcarbamoyl group, a quinoxalin-2-ylcarbamoyl group, a quinoxalin-3-ylcarbamoyl group, a cinnolin-3-ylcarbamoyl group, a cinnolin-4-ylcarbamoyl group, a 1H-benzimidazol-2-ylcarbamoyl group, a 1H-imidazo[4,5-b]pyridin-5-ylcarbamoyl group, a 1H-imidazo[4,5-b]pyridin-6-ylcarbamoyl group, a 1H-imidazo[4,5-b]pyridin-7-ylcarbamoyl group, a benzo[d]isoxazol-4-ylcarbamoyl group, a benzo[d]isoxazol-5-ylcarbamoyl group, a benzo[d]isoxazol-6-ylcarbamoyl group, a benzoxazol-4-ylcarbamoyl group, a benzoxazol-5-ylcarbamoyl group, a benzoxazol-6-ylcarbamoyl group et al.

The arylalkylcarbamoyl group for the substituent is a carbamoyl group with the above-mentioned one or two "aralkyl groups" bonding thereto, including, for example, a benzylcarbamoyl group, a 1-phenylethylcarbamoyl group, a 2-phenylethylcarbamoyl group, a 1-naphthylmethylcarbamoyl group, a 2-naphthylmethylcarbamoyl group et al.

The heteroarylalkylcarbamoyl group for the substituent means a carbamoyl group with the above-mentioned one or two "heteroarylalkyl groups" bonding thereto, including, for example, a furan-3-yl-methylcarbamoyl group, a furan-2-yl-methylcarbamoyl group, a furan-3-ylethylcarbamoyl group, a furan-2-ylethylcarbamoyl group, a furan-3-ylpropylcarbamoyl group, a furan-2-ylpropylcarbamoyl group, a thiophen-3-ylmethylcarbamoyl group, a thiophen-2-ylmethylcarbamoyl group, a thiophen-3-ylethylcarbamoyl group, a thiophen-2-ylethylcarbamoyl group, a thiophen-3-ylpropylcarbamoyl group, a thiophen-2-ylpropylcarbamoyl group, a 1H-pyrrol-3-ylmethylcarbamoyl group, a 1H-pyrrol-2-ylmethylcarbamoyl group, a 1H-pyrrol-3-ylethylcarbamoyl group, a 1H-pyrrol-2-ylethylcarbamoyl group, a 1H-pyrrol-3-ylpropylcarbamoyl group, a 1H-pyrrol-2-ylpropylcarbamoyl group, a 1H-imidazol-4-ylmethylcarbamoyl group, a 1H-imidazol-2-ylmethylcarbamoyl group, a 1H-imidazol-5-ylmethylcarbamoyl group, a 1H-imidazol-4-ylethylcarbamoyl group, a 1H-imidazol-2-ylethylcarbamoyl group, a 1H-imidazol-5-ylethylcarbamoyl group, a 1H-imidazol-4-ylpropylcarbamoyl group, a 1H-imidazol-2-ylpropylcarbamoyl group, a 1H-imidazol-5-ylpropylcarbamoyl group, a 1H-[1,2,3]triazol-4-ylmethylcarbamoyl group, a 1H-[1,2,3]triazol-5-ylmethylcarbamoyl group, a 1H-[1,2,3]triazol-4-ylethylcarbamoyl group, a 1H-[1,2,3]triazol-5-ylethylcarbamoyl group, a 1H-[1,2,3]triazol-4-ylpropylcarbamoyl group, a 1H-[1,2,3]triazol-5-ylpropylcarbamoyl group, a 1H-[1,2,4]triazol-3-ylmethylcarbamoyl group, a 1H-[1,2,4]triazol-5-ylmethylcarbamoyl group, a 1H-[1,2,4]triazol-3-ylethylcarbamoyl group, a 1H-[1,2,4]triazol-5-ylethylcarbamoyl group, a 1H-[1,2,4]triazol-3-ylpropylcarbamoyl group, a 1H-[1,2,4]triazol-5-ylpropylcarbamoyl group, a thiazol-4-ylmethylcarbamoyl group, a thiazol-3-ylmethylcarbamoyl group, a thiazol-2-ylmethylcarbamoyl group, a thiazol-4-ylethylcarbamoyl group, a thiazol-3-ylethylcarbamoyl group, a thiazol-2-ylethylcarbamoyl group, a thiazol-4-ylpropylcarbamoyl group, a thiazol-3-ylpropylcarbamoyl group, a thiazol-2-ylpropylcarbamoyl group, a [1,2,4]thiadiazol-3-ylmethylcarbamoyl group, a [1,2,4]thiadiazol-3-ylethylcarbamoyl group, a [1,2,4]thiadiazol-3-ylpropylcarbamoyl group, a [1,2,4]thiadiazol-5-ylmethylcarbamoyl group, a [1,2,4]thiadiazol-5-ylethylcarbamoyl group, a [1,2,4]thiadiazol-5-ylpropylcarbamoyl group, a [1,3,4]thiadiazol-2-2-ylmethylcarbamoyl group, a [1,3,4]thiadiazol-2-ylethylcarbamoyl group, a [1,3,4]thiadiazol-2-ylpropylcarbamoyl group et al.

The lower alkylthio group for the substituent means a group of the above-mentioned lower alkyl group bonding to a sulfur atom, including, for example, a methylthio group, an ethylthio group, a propylthio group, an isopropylthio group et al.

The aryloxy group for the substituent means a group of the above-mentioned aryl group bonding to an oxygen atom, including, for example, a phenoxy group, a naphthalen-1-yloxy group, a naphthalen-2-yloxy group.

The aryloxycarbonylamino group for the substituent means a group of the above-mentioned aryloxy group bonding to a carbonylamino group, including, for example, a phenoxycarbonylamino group et al.

The arylalkyloxycarbonylamino group for the substituent includes, for example, a benzyloxycarbonylamino group, a 1-phenylethyloxycarbonylamino group, a 2-phenylethyloxycarbonylamino group, a 1-naphthylmethyloxycarbonylamino group, a 2-naphthylmethyloxycarbonylamino group et al.

The alkoxycarbonylamino group for the substituent means the above-mentioned alkoxy group bonding to a carbonylamino group, including, for example, a methoxycarbonylamino group, an ethoxycarbonylamino group, a propoxycarbonylamino group et al.

The alkanoylamino group for the substituent means the above-mentioned alkanoyl group bonding to an amino group, including, for example, a methylcarbonylamino group, an ethylcarbonylamino group, a propylcarbonylamino group, an isopropylcarbonylamino group, an isobutylcarbonylamino group et al.

The arylcarbonylamino group for the substituent means the above-mentioned aryl carbonyl group bonding to a carbonylamino group, including, for example, a phenylcarbonylamino group, a naphthalen-1-ylcarbonylamino group, a naphthalen-2-ylcarbonylamino group et al.

The arylalkylcarbonyl group for the substituent means the above-mentioned aralkyl group bonding to a carbonyl group, including, for example, a benzylcarbonyl group, a naphthalen-1-ylcarbonyl group, a naphthalen-2-ylcarbonyl group et al.

The lower alkylsulfonylamino group for the substituent means the above-mentioned lower alkyl group bonding to a sulfonylamino group, including, for example, a methylsulfonylamino group, an ethylsulfonylamino group, an isopropylsulfonylamino group, an n-butylsulfonylamino group et al.

The arylsulfonylamino group for the substituent means the above-mentioned aryl group bonding to a sulfonylamino group, including, for example, a phenylsulfonylamino group, a naphthalen-1-ylsulfonylamino group, a naphthalen-2-ylsulfonylamino group et al.

The lower alkylsulfamoyl group for the substituent means a sulfonyl group with the above-mentioned one or two "alkylamino groups" bonding thereto, including, for example, a methylsulfamoyl group, an ethylsulfamoyl group, a propylsulfamoyl group, an isopropylsulfamoyl group, a dimethylsulfamoyl group, a diethylsulfamoyl group, an ethylmethylsulfamoyl group, an isopropylmethylsulfamoyl group et al.

The arylsulfamoyl group for the substituent means the above-mentioned aryl group bonding to an aminosulfonyl group, including, for example, a phenylsulfamoyl group, a naphthalen-1-ylsulfamoyl group, a naphthalen-2-ylsulfamoyl group.

The aryl group for the substituent includes the same as those of the above-mentioned aryl group.

The heteroaryl group for the substituent includes the same as those of the above-mentioned heteroaryl group.

The aralkyl group for the substituent includes the same as those of the above-mentioned aralkyl group.

The aralkyloxy group for the substituent includes the above-mentioned aralkyl group bonding to an oxygen atom.

The substituent group α is preferably a halogen atom, a hydroxyl group, a lower alkyl group (the group may be substituted with a halogen atom, a hydroxyl group or an alkoxy group), a cycloalkyl group (the group may be substituted with a halogen atom, a hydroxyl group or an alkoxy group), an alkoxy group, a cycloalkoxy group (one carbon atom constituting the cycloalkoxy group may be substituted with a nitrogen atom, and the nitrogen atom may be substituted with an alkanoyl group), a cyano group, an alkanoyl group, a lower alkylsulfonyl group, a lower alkylthio group, an aryl group, an aryloxy group or a heteroaryl group; more preferably a halogen atom, a hydroxyl group, a lower alkyl group (the group may be substituted with a halogen atom, a hydroxyl group or an alkoxy group), or an alkoxy group.

A represents —(C(R$^3$)(R$^4$))$_{m1}$—, —C(O)—, —O— or —N(R$^5$)—.

$R^3$ and $R^4$ each independently represent a hydrogen atom, a hydroxyl group, a lower alkyl group, an aralkyl group or an aryl group.

m1 means 0 or 1.

$R^5$ represents a hydrogen atom, a lower alkyl group, an aralkyl group or an aryl group.

—C($R^3$)($R^4$)— for A concretely includes, for example, a single bond, a methylene group, —CH(CH$_3$)—, —C(CH$_3$)$_2$—. Of those, preferred are a single bond, a methylene group.

—N($R^5$)— for A includes, for example, —NH—, a methylamino group, an ethylamino group, an isopropylamino group et al. Of those, preferred are —NH—, a methylamino group, an ethylamino group.

B represents —N(SO$_2$R$^1$)—, —N(COR$^2$)—, —N(R$^{50}$)—, —O— or —C(O)—.

$R^1$ and $R^2$ each independently represent a hydrogen atom, a lower alkyl group, an aralkyl group or an aryl group.

$R^{50}$ represents a hydrogen atom or a lower alkyl group.

—N(SO$_2$R$^1$)— for B includes, for example, a methanesulfonylamino group, an ethanesulfonylamino group, an isopropylsulfonylamino group, a benzylsulfonylamino group, a phenylsulfonylamino group et al. Of those, preferred are a methanesulfonylamino group, an ethanesulfonylamino group.

—N(COR$^2$)— for B includes, for example, a methylcarbonylamino group, an ethylcarbonylamino group, an isopropylcarbonylamino group, a phenylcarbonylamino group, a benzylcarbonylamino group et al. Of those, preferred are a methylcarbonylamino group, an ethylcarbonylamino group.

—N(R$^{50}$)— for B includes, for example, —NH—, a methylamino group, an ethylamino group, an isopropylamino group, a benzylsulfonylamino group, a phenylsulfonylamino group et al. Of those, preferred are —NH—, a methylamino group, an ethylamino group.

D represents —(C(R$^{30}$)(R$^{40}$))$_{m2}$—, —O—, —N(R$^{51}$)— or —C(O)—.

$R^{30}$ and $R^{40}$ each independently represent a hydrogen atom, a hydroxyl group, a lower alkyl group, an aralkyl group or an aryl group.

m2 means 0 or 1.

$R^{51}$ represents a hydrogen atom or a lower alkyl group.

—(C(R$^{30}$)(R$^{40}$))$_{m2}$— for D includes, for example, a single bond, a methylene group, —CH(CH$_3$)—, —C(CH$_3$)$_2$— et al.

—N(R$^{51}$)— for D includes, for example, —NH—, a methylamino group, an ethylamino group, an isopropylamino group et al. Of those, preferred are —NH—, a methylamino group, an ethylamino group.

Q represents a methine group or a nitrogen atom.

A group of the following formula (III):

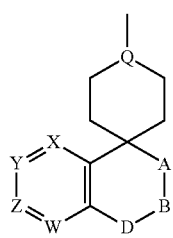
(III)

[wherein the symbols have the same meanings as above] concretely includes, for example, groups of the following formula (III-1):

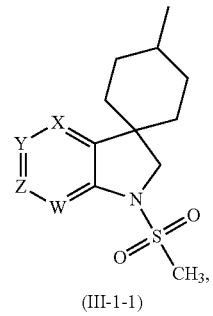
(III-1)

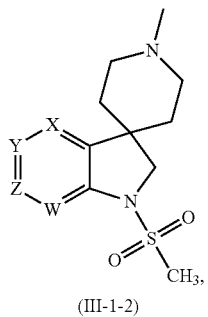
(III-1-1)

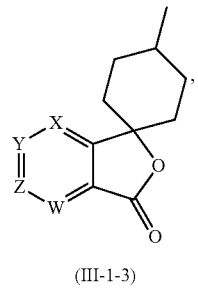
(III-1-2)

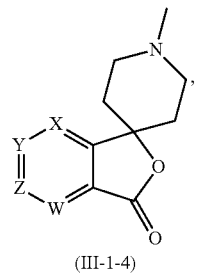
(III-1-3)

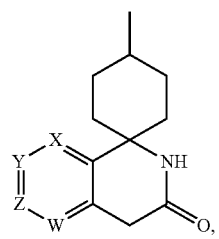
(III-1-4)

(III-1-5)

groups of the following formula (III-2):

-continued
or
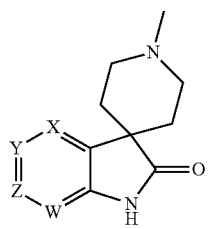
(III-2-6)
groups of the following formula (III-3):
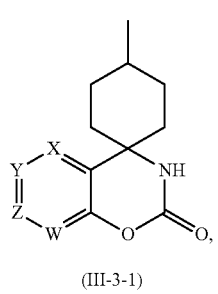
(III-3)
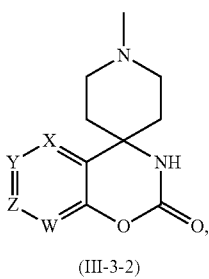
(III-3-1)
(III-3-2)
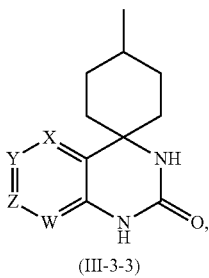
(III-3-3)
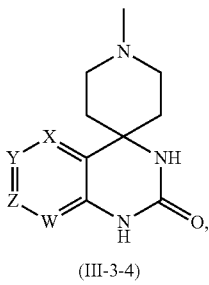
(III-3-4)
-continued
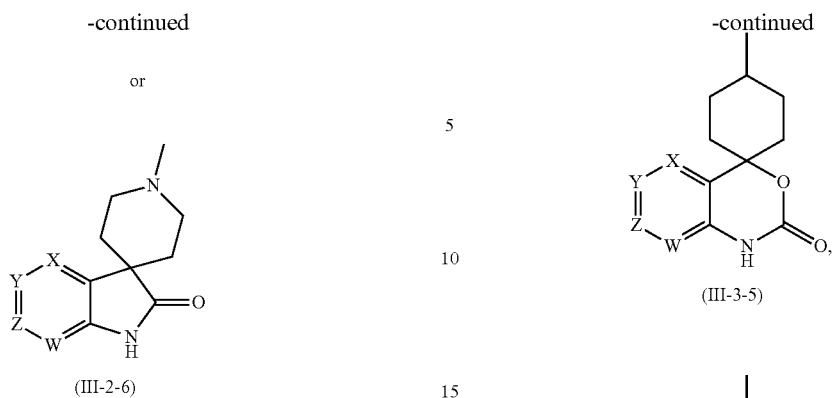
(III-3-5)
(III-3-6)
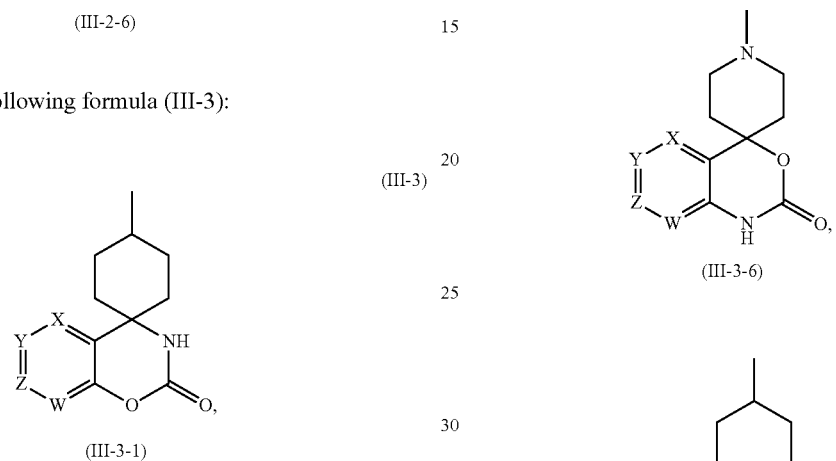
(III-3-7)
(III-3-8)
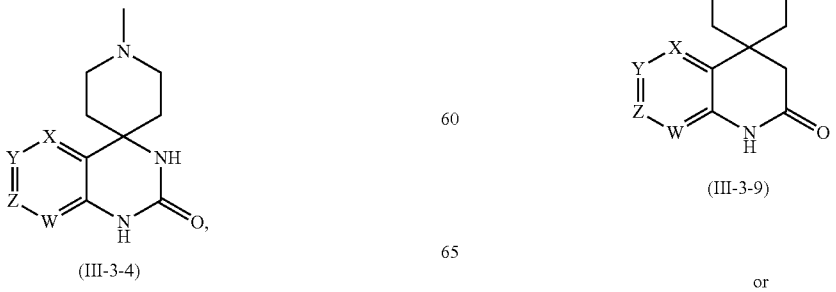
(III-3-9)
or

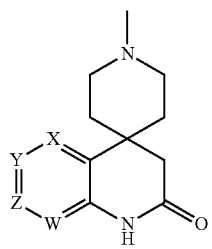
(III-3-10)
groups of the following formula (III-4):
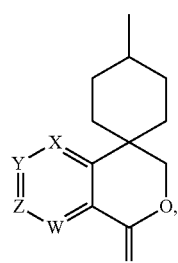
(III-4-1)
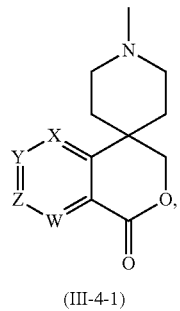
(III-4-1)
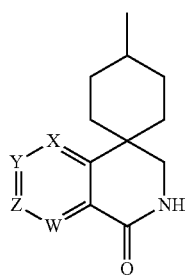
(III-4-1)
or
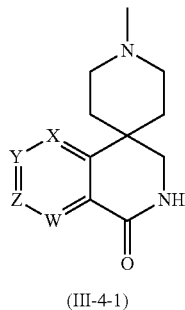
(III-4-1)
groups of the following formula (III-5):
(III-5)
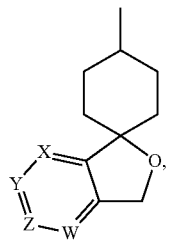
(III-5-1)
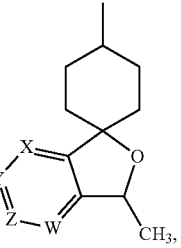
(III-5-2)
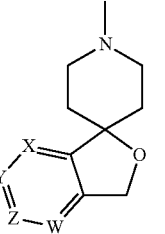
(III-5-3)
or
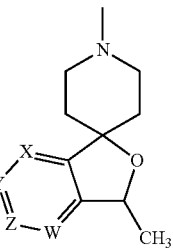
(III-5-4)

Of the groups of formulae (III-1) to (III-5), preferred are groups (III-1), (III-2) or (III-5); more preferred are groups of (III-1).

Of the groups of formulae (III-1), preferred are groups of (III-1-1), (III-1-2), (III-1-3), (III-1-4), (III-1-5), (III-1-6), (III-1-7), (III-1-8), (III-1-9); more preferred are groups of (III-1-3), (III-1-4), (III-1-5), (III-1-6) and (III-1-7).

R represents a group of the following formula (II):

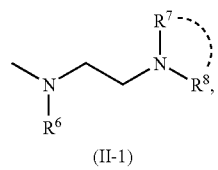
(II-1)

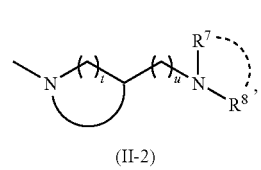
(II-2)

(II)

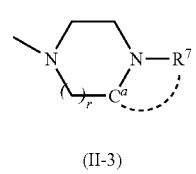
(II-3)

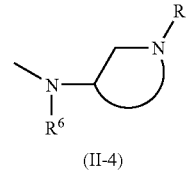
(II-4)

or

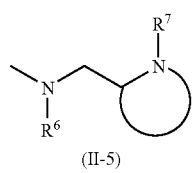
(II-5)

[wherein the symbols have the same meanings as above].

Any hydrogen atom in the formulae (II) may be substituted with a group consisting from a lower alkyl (this alkyl may be substituted with halogen, oxo or an alkoxy), a cycloalkyl, a hydroxy, an alkoxy(this alkoxy may be substituted with a halogen), and a halogen.

$R^6$ represents a hydrogen atom or a lower alkyl group.

$R^7$ and $R^8$ each independently represent a lower alkyl group, a cycloalkyl group, an aralkyl group, a heteroarylalkyl group; or $R^7$ and $R^8$ together with the nitrogen atom to which they bond form a 4- to 8-membered nitrogen-containing aliphatic heterocyclic group.

Or $R^7$ and $C^a$ together with the nitrogen atom to which they bond form a 4- to 8-membered nitrogen-containing aliphatic heterocyclic group.

"4- to 8-Membered nitrogen-containing aliphatic heterocyclic group" concretely include, for example, an azetidinyl group, a pyrrolidinyl group, a piperidinyl group, a homopiperidinyl group, a morpholino group et al.

The group of formula (II-1) concretely includes, for example, groups of the following formula (II-1-1):

(II-1-1)

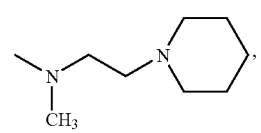

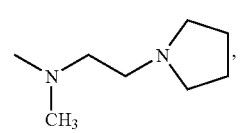

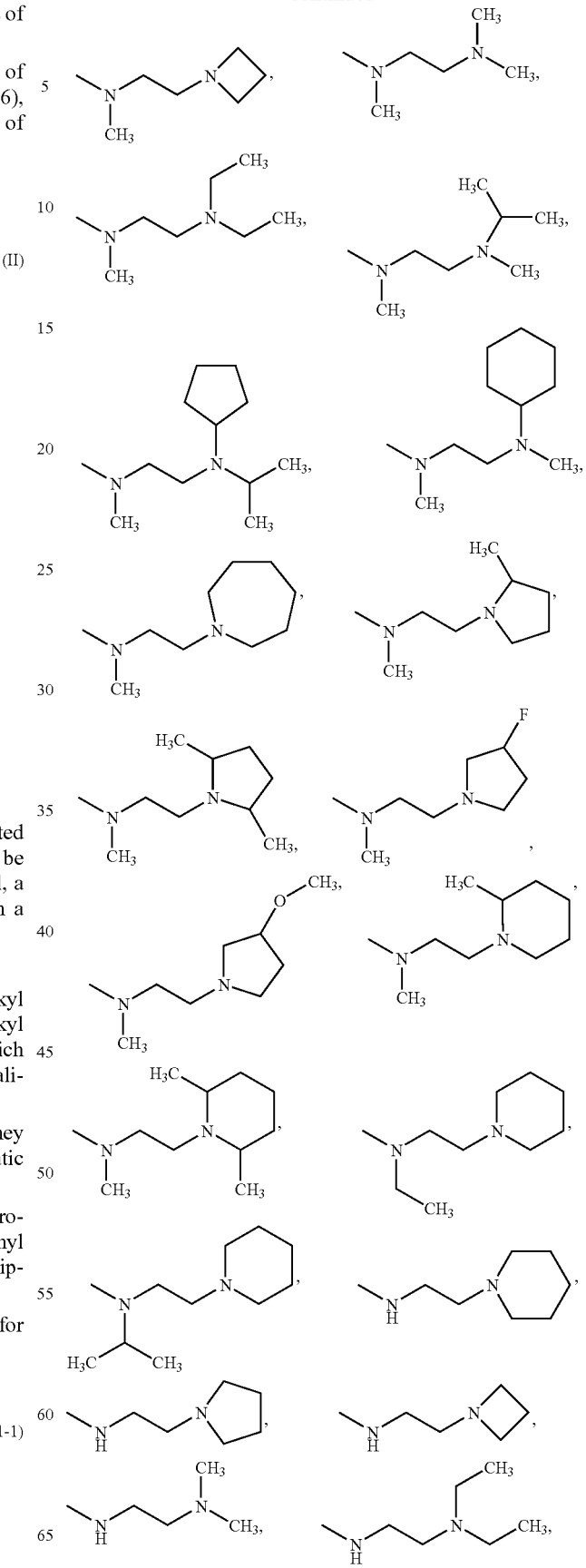

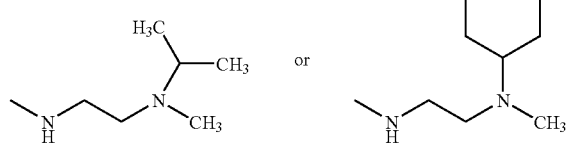
Of those, preferred are groups of the following formula (II-1-2):
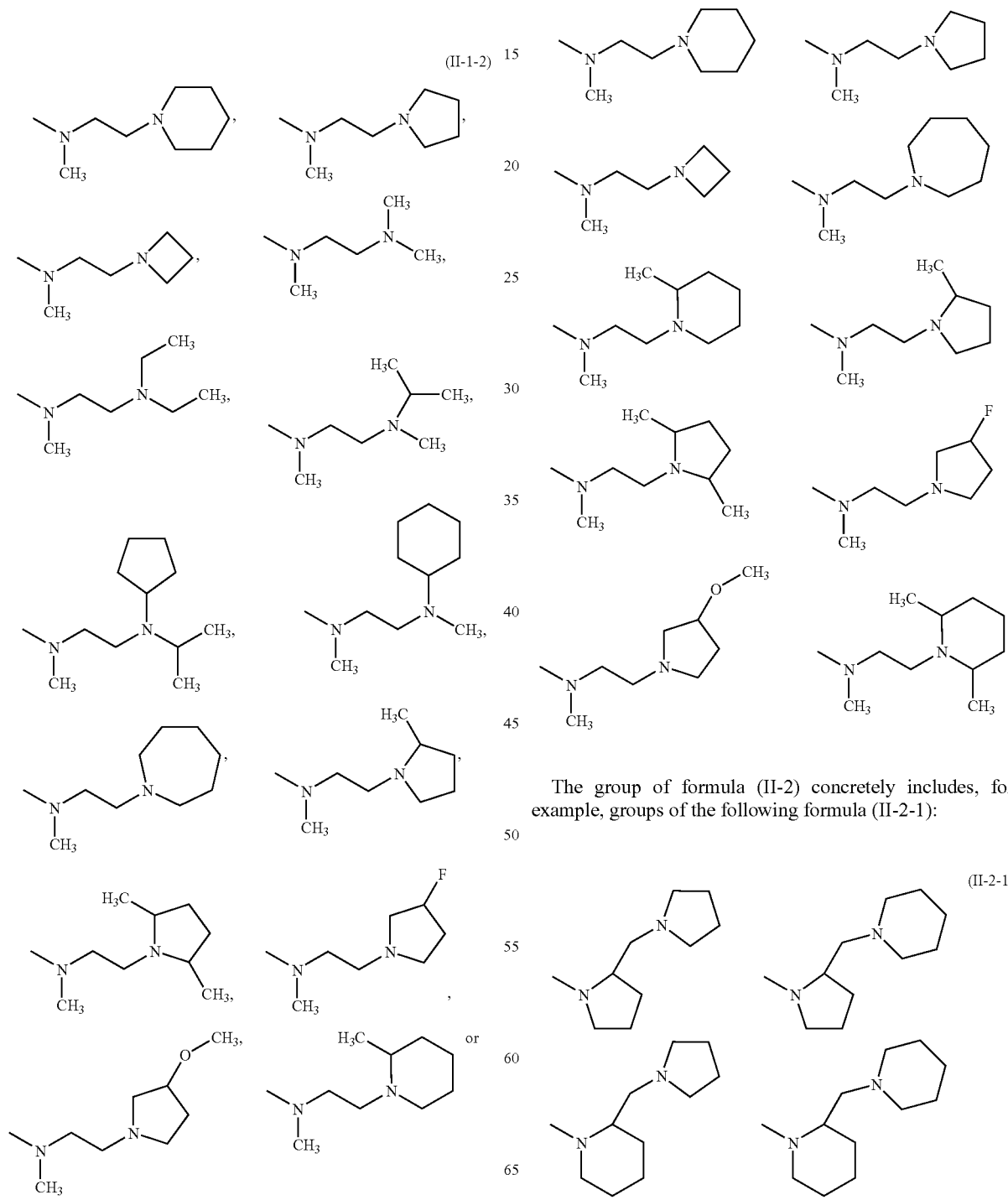
and more preferred is following;
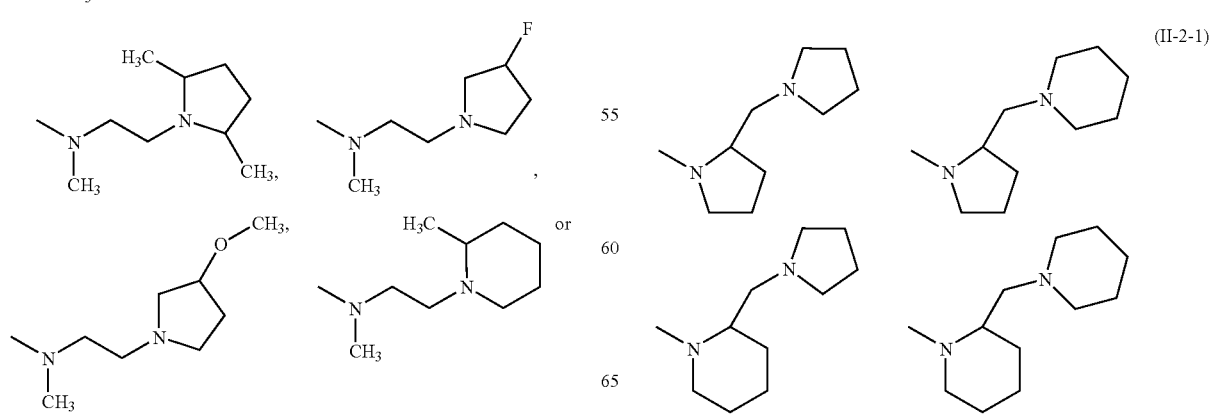
The group of formula (II-2) concretely includes, for example, groups of the following formula (II-2-1):

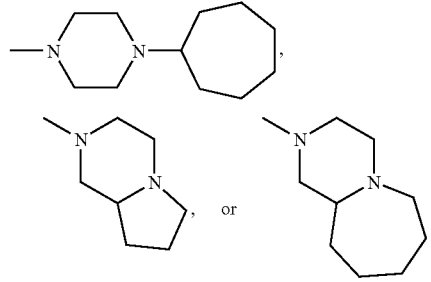
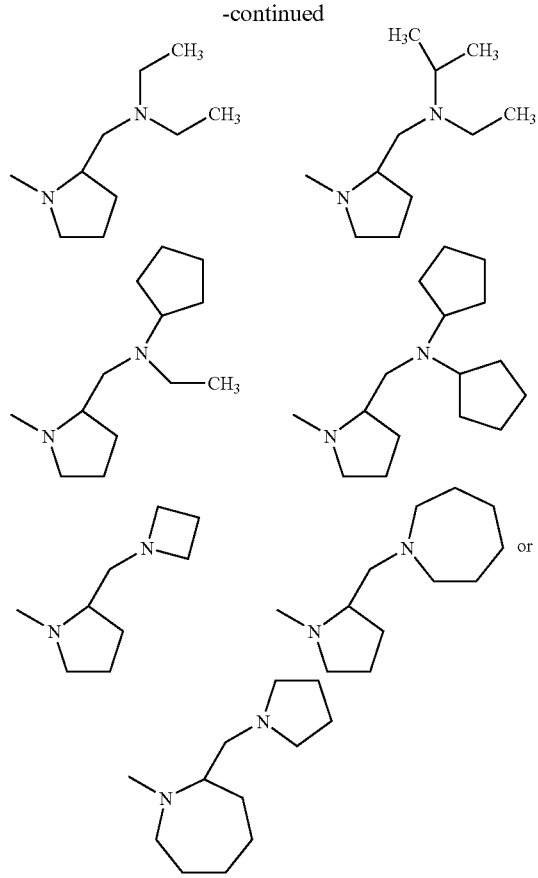
The group of formula (II-3) concretely includes, for example, groups of the following formula (II-3-1):
The group of formula (II-4) concretely includes, for example, groups of the following formula (II-4-1):
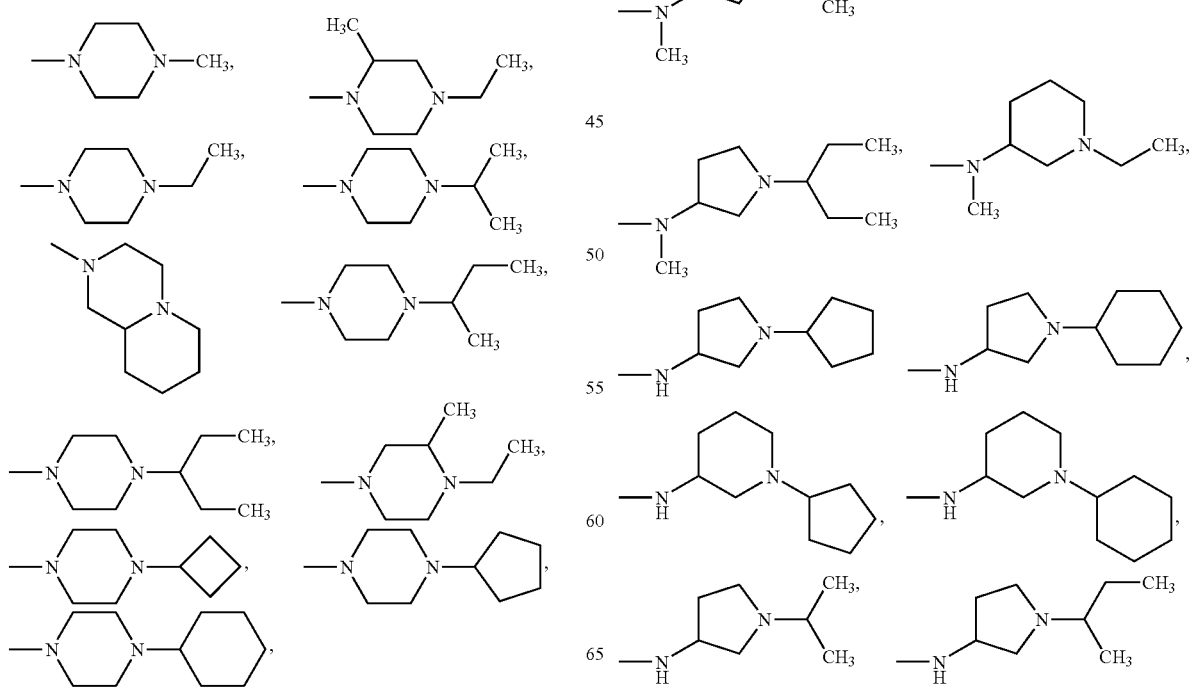

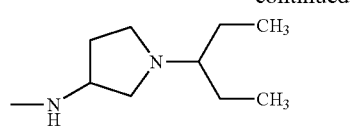

Of those, preferred are groups of the following formula (II-4-2):

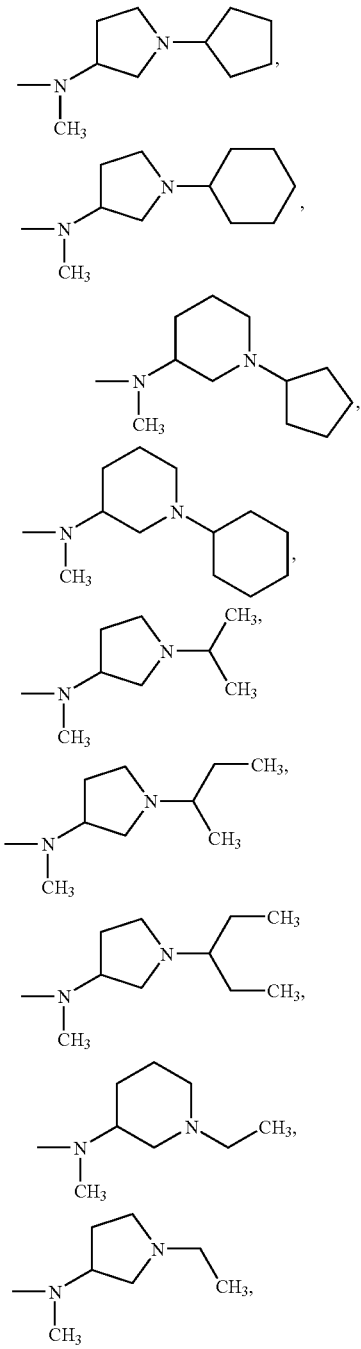

The group of formula (II-5) concretely includes, for example, groups of the following formula (II-5-1):

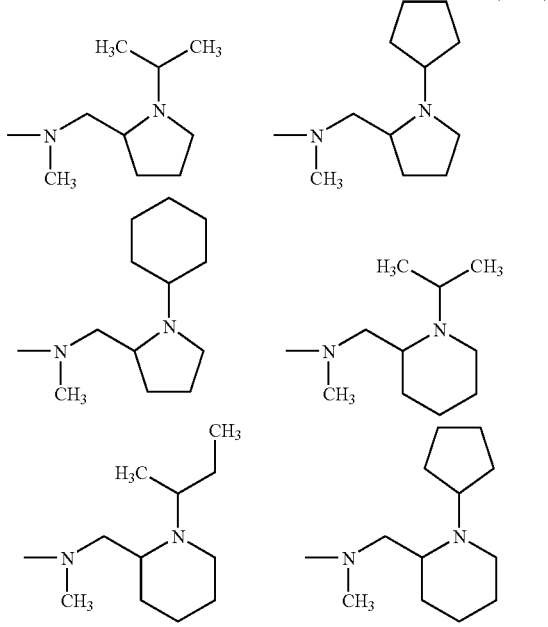

Of the groups of formula (II), preferred are groups of (II-1), (II-2), (II-3), (II-4); more preferred are groups of (II-1).

Concretely, the compounds of formula (I) or their pharmaceutically-acceptable salts include, for example, the following:

Trans-5'-chloro-3'-oxo-N-methyl-N-(2-pyrrolidin-1-yl-ethyl)-spiro[cyclohexane-1,1'-(3'H)-4'-azaisobenzofuran]-4-carboxamide, Trans-3'-oxo-N-methyl-N-(2-piperidin-1-ylethyl)-spiro[cyclohexane-1,1'-(3'H)-4'-azaisobenzofuran]-4-carboxamide, Trans-3'-oxo-N-methyl-N-(2-pyrrolidin-1-ylethyl)-spiro[cyclohexane-1,1'-(3'H)-4'-azaisobenzofuran]-4-carboxamide, Trans-5'-chloro-3'-oxo-N-methyl-N-(2-piperidin-1-ylethyl)-spiro[cyclohexane-1,1'-(3'H)-4'-azaisobenzofuran]-4-carboxamide, Trans-3'-oxo-N-methyl-N-(2-piperidin-1-ylethyl)-spiro[cyclohexane-1,1'-(3'H)-5'-azaisobenzofuran]-4-carboxamide, Trans-3'-oxo-N-methyl-N-(2-pyrrolidin-1-ylethyl)-spiro[cyclohexane-1,1'-(3'H)-5'-azaisobenzofuran]-4-carboxamide, Trans-3'-oxo-N-methyl-N-(2-piperidin-1-ylethyl)-spiro[cyclohexane-1,1'-(3'H)-6'-azaisobenzofuran]-4-carboxamide, Trans-3'-oxo-N-methyl-N-(2-piperidin-1-ylethyl)-spiro[cyclohexane-1,1'-(3'H)-7'-azaisobenzofuran]-4-carboxamide, Trans-5'-fluoro-3'-oxo-N-methyl-N-(2-pyrrolidin-1-yl-ethyl)-spiro[cyclohexane-1,1'-(3'H)-6'-azaisobenzofuran]-4-carboxamide, Trans-5'-ethoxy-3'-oxo-N-methyl-N-(2-pyrrolidin-1-yl-ethyl)-spiro[cyclohexane-1,1'-(3'H)-4'-azaisobenzofuran]-4-carboxamide, Trans-5'-methoxy-3'-oxo-N-methyl-N-(2-piperidin-1-yl-ethyl)-spiro[cyclohexane-1,1'-(3'H)-4'-azaisobenzofuran]-4-carboxamide, Trans-5'-ethoxy-3'-oxo-N-methyl-N-(2-piperidin-1-yl-ethyl)-spiro[cyclohexane-1,1'-(3'H)-4'-azaisobenzofuran]-4-carboxamide, Trans-5'-methoxy-3'-oxo-N-methyl-N-(2-pyrrolidin-1-yl-ethyl)-spiro[cyclohexane-1,1'-(3'H)-4'-azaisobenzofuran]-4-carboxamide,
Trans-5'-propoxy-3'-oxo-N-methyl-N-(2-pyrrolidin-1-yl-ethyl)-spiro[cyclohexane-1,1'-(3'H)-4'-azaisobenzofuran]-4-carboxamide,
Trans-5'-(morpholin-4-yl)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(dimethylamino)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(piperidin-1-yl)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(piperidin-1-yl)-3'-oxo-N-methyl-N-(2-piperidin-1-ylethyl)-spiro[cyclohexane-1,1'-(3'H)-4'-azaisobenzofuran]-4-carboxamide,
Trans-5'-phenoxy-3'-oxo-N-methyl-N-(2-piperidin-1-ylethyl)-spiro[cyclohexane-1,1'-(3'H)-4'-azaisobenzofuran]-4-carboxamide,
Trans-5'-(pyridin-3-yloxy)-3'-oxo-N-methyl-N-(2-piperidin-1-ylethyl)-spiro[cyclohexane-1,1'-(3'H)-4'-azaisobenzofuran]-4-carboxamide,
Trans-5'-phenyl-3'-oxo-N-methyl-N-(2-pyrrolidin-1-ylethyl)-spiro[cyclohexane-1,1'-(3'H)-4'-azaisobenzofuran]-4-carboxamide,
Trans-5'-phenyl-3'-oxo-N-methyl-N-(2-piperidin-1-ylethyl)-spiro[cyclohexane-1,1'-(3'H)-4'-azaisobenzofuran]-4-carboxamide,
Trans-5'-(4-fluorophenyl)-3'-oxo-N-methyl-N-(2-piperidin-1-ylethyl)-spiro[cyclohexane-1,1'-(3'H)-4'-azaisobenzofuran]-4-carboxamide,
Trans-5'-(pyrimidin-5-yl)-3'-oxo-N-methyl-N-(2-piperidin-1-ylethyl)-spiro[cyclohexane-1,1'-(3'H)-4'-azaisobenzofuran]-4-carboxamide,
Trans-5'-(6-methoxypyridin-3-yl)-3'-oxo-N-methyl-N-(2-piperidin-1-ylethyl)-spiro[cyclohexane-1,1'-(3'H)-4'-azaisobenzofuran]-4-carboxamide,
Trans-5'-[4-(methylsulfonyl)phenyl]-3'-oxo-N-methyl-N-(2-piperidin-1-ylethyl)-spiro[cyclohexane-1,1'-(3'H)-4'-azaisobenzofuran]-4-carboxamide,
Trans-5'-(6-methoxypyridin-3-yl)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(1-methyl-1H-pyrazol-4-yl)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(2,4-dimethoxypyrimidin-5-yl)-3'-oxo-N-methyl-N-(2-piperidin-1-ylethyl)-spiro[cyclohexane-1,1'-(3'H)-4'-azaisobenzofuran]-4-carboxamide,
Trans-5'-ethyl-3'-oxo-N-methyl-N-(2-piperidin-1-ylethyl)-spiro[cyclohexane-1,1'-(3'H)-4'-azaisobenzofuran]-4-carboxamide,
N-methyl-7'-oxo-N-(2-piperidin-1-ylethyl)-7'H-spiro[cyclohexane-1,5'-furo[3,4-b]pyridine]-4-carboxamide,
Trans-4'-chloro-3'-oxo-N-methyl-N-(2-piperidin-1-ylethyl)-spiro[cyclohexane-1,1'-(3'H)-5'-azaisobenzofuran]-4-carboxamide,
Trans-4'-chloro-3'-oxo-N-methyl-N-(2-pyrrolidin-1-yl-ethyl)-spiro[cyclohexane-1,1'-(3'H)-5'-azaisobenzofuran]-4-carboxamide,
Trans-4'-methoxy-3'-oxo-N-methyl-N-(2-piperidin-1-yl-ethyl)-spiro[cyclohexane-1,1'-(3'H)-5'-azaisobenzofuran]-4-carboxamide,
Trans-4'-methoxy-3'-oxo-N-methyl-N-(2-pyrrolidin-1-yl-ethyl)-spiro[cyclohexane-1,1'-(3'H)-5'-azaisobenzofuran]-4-carboxamide,
Trans-4'-ethoxy-3'-oxo-N-methyl-N-(2-piperidin-1-yl-ethyl)-spiro[cyclohexane-1,1'-(3'H)-5'-azaisobenzofuran]-4-carboxamide,
Trans-4'-ethoxy-3'-oxo-N-methyl-N-(2-pyrrolidin-1-yl-ethyl)-spiro[cyclohexane-1,1'-(3'H)-5'-azaisobenzofuran]-4-carboxamide,
Trans-4'-isopropoxy-3'-oxo-N-methyl-N-(2-piperidin-1-yl-ethyl)-spiro[cyclohexane-1,1'-(3'H)-5'-azaisobenzofuran]-4-carboxamide,
Trans-4'-isopropoxy-3'-oxo-N-methyl-N-(2-pyrrolidin-1-yl-ethyl)-spiro[cyclohexane-1,1'-(3'H)-5'-azaisobenzofuran]-4-carboxamide,
Trans-4'-cyclopropylmethoxy-3'-oxo-N-methyl-N-(2-pyrrolidin-1-ylethyl)-spiro[cyclohexane-1,1'-(3'H)-5'-azaisobenzofuran]-4-carboxamide,
Trans-4'-methyl-3'-oxo-N-methyl-N-(2-piperidin-1-yl-ethyl)-spiro[cyclohexane-1,1'-(3'H)-5'-azaisobenzofuran]-4-carboxamide,
Trans-4'-ethyl-3'-oxo-N-methyl-N-(2-pyrrolidin-1-ylethyl)-spiro[cyclohexane-1,1'-(3'H)-5'-azaisobenzofuran]-4-carboxamide,
Trans-4'-phenyl-3'-oxo-N-methyl-N-(2-piperidin-1-yl-ethyl)-spiro[cyclohexane-1,1'-(3'H)-5'-azaisobenzofuran]-4-carboxamide,
Trans-4'-(4-fluorophenyl)-3'-oxo-N-methyl-N-(2-pyrrolidin-1-ylethyl)-spiro[cyclohexane-1,1'-(3'H)-5'-azaisobenzofuran]-4-carboxamide,
Trans-4'-(1-methyl-1H-pyrazol-4-yl)-3'-oxo-N-methyl-N-(2-piperidin-1-ylethyl)-spiro[cyclohexane-1,1'-(3'H)-5'-azaisobenzofuran]-4-carboxamide,
Trans-4'-phenoxy-3'-oxo-N-methyl-N-(2-piperidin-1-yl-ethyl)-spiro[cyclohexane-1,1'-(3'H)-5'-azaisobenzofuran]-4-carboxamide,
Trans-4'-(4-fluorophenoxy)-3'-oxo-N-methyl-N-(2-pyrrolidin-1-ylethyl)-spiro[cyclohexane-1,1'-(3'H)-5'-azaisobenzofuran]-4-carboxamide,
Trans-4'-(pyrrolidin-1-yl)-3'-oxo-N-methyl-N-(2-piperidin-1-ylethyl)-spiro[cyclohexane-1,1'-(3'H)-5'-azaisobenzofuran]-4-carboxamide,
Trans-4'-(piperidin-1-yl)-3'-oxo-N-methyl-N-(2-pyrrolidin-1-ylethyl)-spiro[cyclohexane-1,1'-(3'H)-5'-azaisobenzofuran]-4-carboxamide,
Trans-4'-(pyrrolidin-1-yl)-3'-oxo-N-methyl-N-(2-pyrrolidin-1-ylethyl)-spiro[cyclohexane-1,1'-(3'H)-5'-azaisobenzofuran]-4-carboxamide,
Trans-4'-(morpholin-4-yl)-3'-oxo-N-methyl-N-(2-piperidin-1-ylethyl)-spiro[cyclohexane-1,1'-(3'H)-5'-azaisobenzofuran]-4-carboxamide,
Trans-5'-(pyridin-3-yl)-3'-oxo-N-methyl-N-(2-pyrrolidin-1-ylethyl)-spiro[cyclohexane-1,1'-(3'H)-4'-azaisobenzofuran]-4-carboxamide,
Trans-5'-(pyridin-3-yl)-3'-oxo-N-methyl-N-(2-piperidin-1-ylethyl)-spiro[cyclohexane-1,1'-(3'H)-4'-azaisobenzofuran]-4-carboxamide,
Trans-5'-pyrazinyl-3'-oxo-N-methyl-N-(2-piperidin-1-yl-ethyl)-spiro[cyclohexane-1,1'-(3'H)-4'-azaisobenzofuran]-4-carboxamide,
Trans-5'-benzyloxy-3'-oxo-N-methyl-N-(2-piperidin-1-yl-ethyl)-spiro[cyclohexane-1,1'-(3'H)-4'-azaisobenzofuran]-4-carboxamide,
Trans-5'-hydroxy-3'-oxo-N-methyl-N-(2-piperidin-1-yl-ethyl)-spiro[cyclohexane-1,1'-(3'H)-4'-azaisobenzofuran]-4-carboxamide, or Trans-6'-bromo-5'-methoxy-3'-oxo-N-methyl-N-(2-piperidin-1-ylethyl)-spiro[cyclohexane-1,1'-(3'H)-4'-azaisobenzofuran]-4-carboxamide et al.

Preferably,

Trans-5'-methoxy-3'-oxo-N-methyl-N-(2-piperidin-1-ylethyl)-spiro[cyclohexane-1,1'-(3'H)-4'-azaisobenzofuran]-4-carboxamide, Trans-5'-methoxy-3'-oxo-N-methyl-N-(2-pyrrolidin-1-ylethyl)-spiro[cyclohexane-1,1'-(3'H)-4'-azaisobenzofuran]-4-carboxamide, Trans-4'-methoxy-3'-oxo-N-methyl-N-(2-piperidin-1-ylethyl)-spiro[cyclohexane-1,1'-(3'H)-5'-azaisobenzofuran]-4-carboxamide, Trans-4'-methyl-3'-oxo-N-methyl-N-(2-piperidin-1-ylethyl)-spiro[cyclohexane-1,1'-(3'H)-5'-azaisobenzofuran]-4-carboxamide, Trans-4'-(1-methyl-1H-pyrazol-4-yl)-3'-oxo-N-methyl-N-(2-piperidin-1-ylethyl)-spiro[cyclohexane-1,1'-(3'H)-5'-azaisobenzofuran]-4-carboxamide, Trans-5'-pyrazinyl-3'-oxo-N-methyl-N-(2-piperidin-1-ylethyl)-spiro[cyclohexane-1,1'-(3'H)-4'-azaisobenzofuran]-4-carboxamide et al, are recommended.

The method for preparing the compound of the formula (I)

A compound (I-1) or its pharmaceutically-acceptable salt of the invention can be produced, for example, according to the following method:

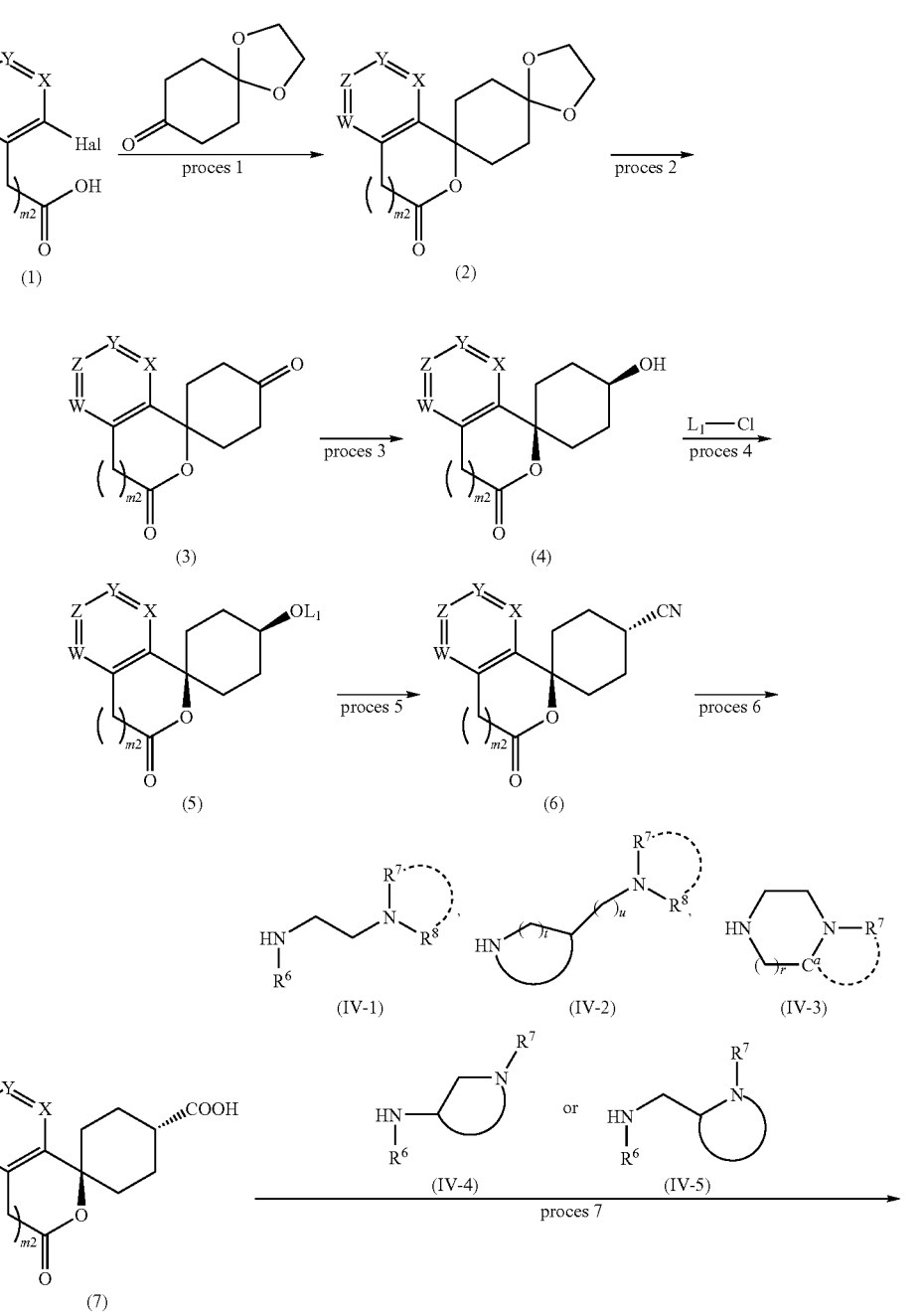

(I-1)

[wherein Hal represents a halogen atom; $L_1$ represents a methanesulfonyl group, a trifluoromethanesulfonyl group or a p-toluenesulfonyl group; and the other symbols have the same meanings as above].

(Step 1)

This step is a process for producing a compound (2) by reacting a compound (1) with 1,4-cyclohexanedione monoethylene ketal in the presence of a base.

The compound (1) to be used in this reaction may be produced according to a method described in literature (for example, WO03/014083), or a method similar to it, or a combination of the method with an ordinary method. The compound (1) includes, for example, 3-bromo-4-pyridinecarboxylic acid, 3-bromo-2-pyridinecarboxylic acid, 2-fluoro-3-chloro-4-pyridinecarboxylic acid et al.

The amount of 1,4-cyclohexanedione monoethylene ketal to be used in this step may be generally from 1 to 5 equivalents relative to one equivalent of the compound (1), preferably from 1 to 2 equivalents.

The usable base includes, for example, butyl lithium, lithium 2,2,6,6-tetramethylpiperidide et al.

The amount of the base to be used may be generally from 2 to 10 equivalents relative to one equivalent of the compound (1), preferably from 2 to 4 equivalents.

Not specifically defined, the reaction solvent may be any one not interfering with the reaction, and includes, for example, tetrahydrofuran (hereinafter abbreviated as "THF"), diethyl ether, tert-butyl methyl ether et al. Of those, preferred are THF.

The reaction temperature may be generally from −100° C. to 100° C., preferably from −78° C. to 50.

The reaction time may be generally from 1 hour to 48 hours, preferably from 1 hour to 24 hours.

Thus obtained, the compound (2) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 2)

This step is a process for producing a compound (3) by removing the ketal group from the compound (2) obtained in the previous step 1. The ketal group may be removed according to a method described in literature (for example, Protective Groups in Organic Synthesis, by T. W. Green, 2nd Ed., John Wiley & Sons, 1991), or a method similar to it, or a combination of the method with an ordinary method.

Concretely, for removing the acetal group, for example, hydrochloric acid, sulfuric acid, paratoluenesulfonic acid or trifluoroacetic acid can be used.

The amount of acid to be used may be generally from 0.1 to 100 equivalents relative to one equivalent of the compound (2), preferably from 0.5 to 50 equivalents.

Not specifically defined, the reaction solvent may be any one not interfering with the reaction, and includes, for example, water, and water-containing methanol, ethanol, acetone, THF, 1,4-dioxane and acetic acid et al. Of those, preferred are methanol, ethanol acetone, THF, 1,4-dioxane.

The reaction temperature may be generally from 0° C. to 200° C., preferably from 20° C. to 150° C.

The reaction time may be generally from 1 hour to 48 hours, preferably from 1 hour to 10 hours.

Thus obtained, the compound (3) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 3)

This step is a process for producing a compound (4) by reducing the carbonyl group of the compound (3) obtained in the previous step 2.

The reducing agent to be used in this step includes, for example, sodium borohydride, lithium borohydride, lithium aluminium hydride, diisobutylaluminium hydride, tri(tert-butoxy)aluminium lithium hydride et al.

The amount of the reducing agent to be used in this step may be generally from 1 to 20 equivalents relative to one equivalent of the compound (3), preferably from 1 to 3 equivalents.

Not specifically defined, the reaction solvent may be any one not interfering with the reaction, and includes, for example, THF, mixed solvent of THF-water, 1,4-dioxane, mixed solvent of dioxane-water, methanol, ethanol, diethyl ether, dichloromethane et al. Of those preferred are THF, mixed solvent of THF-water.

The reaction temperature may be generally from −100° C. to 100° C., preferably from −100° C. to 50° C.

The reaction time may be generally from 5 minutes to 24 hours, preferably from 5 minutes to 4 hours.

Thus obtained, the compound (4) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 4)

This step is a process for producing a compound (5) by reacting the compound (4) with a compound $L_1$-Cl, in the presence of a base.

Concretely, the base to be used in this step includes, for example, triethylamine, sodium carbonate, potassium carbonate, diisopropylethylamine, pyridine et al. Of those, preferred are triethylamine, diisopropylethylamine et al.

The amount of the base to be used may be generally from 1 to 10 equivalents relative to one equivalent of the compound (4), preferably from 1 to 3 equivalents.

The compound $L_1$-Cl to be used includes, for example, methanesulfonyl chloride, trifluoromethanesulfonyl chloride, p-toluenesulfonyl chloride, benzenesulfonyl chloride et al. Of those, preferred are methanesulfonyl chloride, p-toluenesulfonyl chloride et al.

The amount of the compound $L_1$-Cl to be used may be generally from 1 to 10 equivalents relative to one equivalent of the compound (4), preferably from 1 to 3 equivalents.

Not specifically defined, the reaction solvent may be any one not interfering with the reaction, and includes, for example, THF, methylene chloride, chloroform, ethyl acetate et al. Of those, preferred are THF, methylene chloride, chloroform.

The reaction temperature may be generally from 0° C. to 100° C., preferably from 0° C. to 50° C.

The reaction time may be generally from 5 minutes to 12 hours, preferably from 5 minutes to 4 hours.

Thus obtained, the compound (5) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.
(Step 5)

This step is a process for producing a compound (6) by reacting the compound (5) with a cyano compound.

Concretely, the cyano compound to be used in this step includes, for example, tetraethylammonium cyanide, tetrabutylammonium cyanide, sodium cyanide, potassium cyanide et al. Of those, preferred are tetraethylammonium cyanide, tetrabutylammonium cyanide.

The amount of the cyano compound may be generally from 1 to 20 equivalents relative to one equivalent of the compound (5), preferably from 1 to 5 equivalents.

Not specifically defined, the reaction solvent may be any one not interfering with the reaction, and includes, for example, N,N-dimethylformamide (herein after abbreviated as DMF), THF, dimethylsulfoxide, acetonitrile et al. Of those, preferred is DMF.

The reaction temperature may be generally from 0° C. to 150° C., preferably from 50° C. to 100° C.

The reaction time may be generally from 1 hour to 48 hours, preferably from 1 hour to 24 hours.

Thus obtained, the compound (6) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.
(Step 6)

This step is a process for producing a compound (7) by hydrolyzing the compound (6), in the presence of an acid.

The usable acid includes, for example, sulfuric acid, hydrochloric acid et al.

The amount of the acid to be used may be generally from 1 to 100 equivalents relative to one equivalent of the compound (6), preferably from 1 to 50 equivalents.

Not specifically defined, the reaction solvent may be any one not interfering with the reaction, and includes, for example, dioxane, water et al.

The reaction temperature may be generally from 20° C. to 200° C., preferably from 50° C. to 150° C.

The reaction time may be generally from 1 hour to 72 hours, preferably from 1 hour to 24 hours.

Thus obtained, the compound (7) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

The compound (7) may also be produced according to a method described in literature (for example, WO03/014083).
(Step 7)

This step is a process for producing a compound (I-1) of the invention by reacting the compound (7), with a compound (IV-1), (IV-2), (IV-3), (IV-4) or (IV-5).

This reaction may be attained through ordinary amide-forming reaction according to a method described in literature (for example, Bases and Experiments of Peptide Synthesis, Nobuo Izumiya, by Maruzen, 1983; Comprehensive Organic Synthesis, Vol. 6, by Pergamon Press, 1991), or a method similar to it, or a combination of the method with an ordinary method. Specifically, it may be attained using a condensing agent well known by anyone skilled in the art or according to an ester-activation method, a mixed acid anhydride method, an acid chloride method or a carbodiimide method available to anyone skilled in the art. The amide-forming reagent includes, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, 2-chloro-1,3-dimethylimidazolinium chloride, ethyl chloroformate, isobutyl chloroformate, O-(7-azabenzotriazol-1-yl)-1,1,3,3-tetramethyluronium hexafluorophosphate (hereinafter referred to as "HATU"), benzotriazol-1-yl-oxy-tris (dimethylamino)phosphonium hexafluorophosphate et al. Of those, for example, preferred are thionyl chloride, 1-ethyl-3-(3-dimethylaminopropyl)carbodiimide hydrochloride, 2-chloro-1,3-dimethylimidazolinium chloride, N,N-dicyclohexylcarbodiimide, HATU or benzotriazol-1-yl-oxy-tris (dimethylamino)phosphonium hexafluorophosphate et al. In the amide-forming reaction, a base and a condensation promoter may be used along with the above amide-forming reagent.

The usable base includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN) et al; aromatic amines such as pyridine, 4-dimethylaminopyridine, picoline, lutidine, quinoline, isoquinoline et al. Of those, for example, preferred are tertiary aliphatic amines; more preferred are triethylamine or N,N-diisopropylethylamine et al.

The usable condensation promoter includes, for example, N-hydroxybenzotriazole hydrate, N-hydroxysuccinimide, N-hydroxy-5-norbornene-2,3-dicarboxyimide or 3-hydroxy-3,4-dihydro-4-oxo-1,2,3-benzotriazole et al. Of those, for example, preferred is N-hydroxybenzotriazole et al.

The amount of the compound (IV-1), (IV-2), (IV-3), (IV-4) or (IV-5) to be used herein may be generally from 0.1 to 10 equivalents relative to one equivalent of the carboxylic acid derivative (7) or its reactive derivative, preferably from 0.5 to 3 equivalents.

The compound (IV-1) to be used means an amino compound corresponding to the above-mentioned (II-1), concretely including, for example, amino compounds corresponding to the above-mentioned (II-1-1).

The compound (IV-2) to be used means an amino compound corresponding to the above-mentioned (II-2), concretely including, for example, amino compounds corresponding to the above-mentioned (II-2-1).

The compound (IV-3) to be used means an amino compound corresponding to the above-mentioned (II-3), concretely including, for example, amino compounds corresponding to the above-mentioned (II-3-1).

The compound (IV-4) to be used means an amino compound corresponding to the above-mentioned (II-4), concretely including, for example, amino compounds corresponding to the above-mentioned (II-4-1).

The compound (IV-5) to be used means an amino compound corresponding to the above-mentioned (II-5), concretely including, for example, amino compounds corresponding to the above-mentioned (II-5-1).

The amount of the amide-forming reagent to be used may vary depending on the type of the compound and the solvent used and on the other reaction conditions, and may be generally from 1 to 10 equivalents relative to one equivalent of the carboxylic acid compound (7) or its reactive derivative, preferably from 1 to 3 equivalents.

The amount of the condensation promoter to be used may vary depending on the type of the compound and the solvent used and on the other reaction conditions, and may be generally from 1 to 10 equivalents relative to one equivalent of the carboxylic acid compound (7) or its reactive derivative, preferably from 1 to 3 equivalents.

The amount of the base to be used may be generally from 1 to 10 equivalents, preferably from 1 to 5 equivalents.

The reaction solvent to be used in this step is, for example, an inert solvent. Not specifically defined, the solvent may be any one not interfering with the reaction, and concretely includes, for example, methylene chloride, chloroform, 1,2-dichloroethane, DMF, ethyl acetate, methyl acetate, acetonitrile, benzene, xylene, toluene, 1,4-dioxane, THF, dimethoxyethane, and their mixed solvents. From the viewpoint of ensuring favorable reaction temperature, the solvent is, for example, preferably methylene chloride, chloroform, 1,2-dichloroethane, acetonitrile or DMF et al.

The reaction temperature may be generally from −78° C. to the boiling point of the solvent, preferably from 0 to 30° C.

The reaction time may be generally from 0.5 to 96 hours, preferably from 3 to 24 hours.

One or more different types of the base, the amide-forming reagent and the condensation promoter may be used in this step, optionally as combined.

Thus obtained, the compound (I-1) of the invention may be isolated and purified through any ordinary isolation and purification method of, for example, concentration, concentration under reduced pressure, crystallization, solvent extraction, reprecipitation or chromatography.

The compound (I-2) of the invention may also be produced according to the following method:

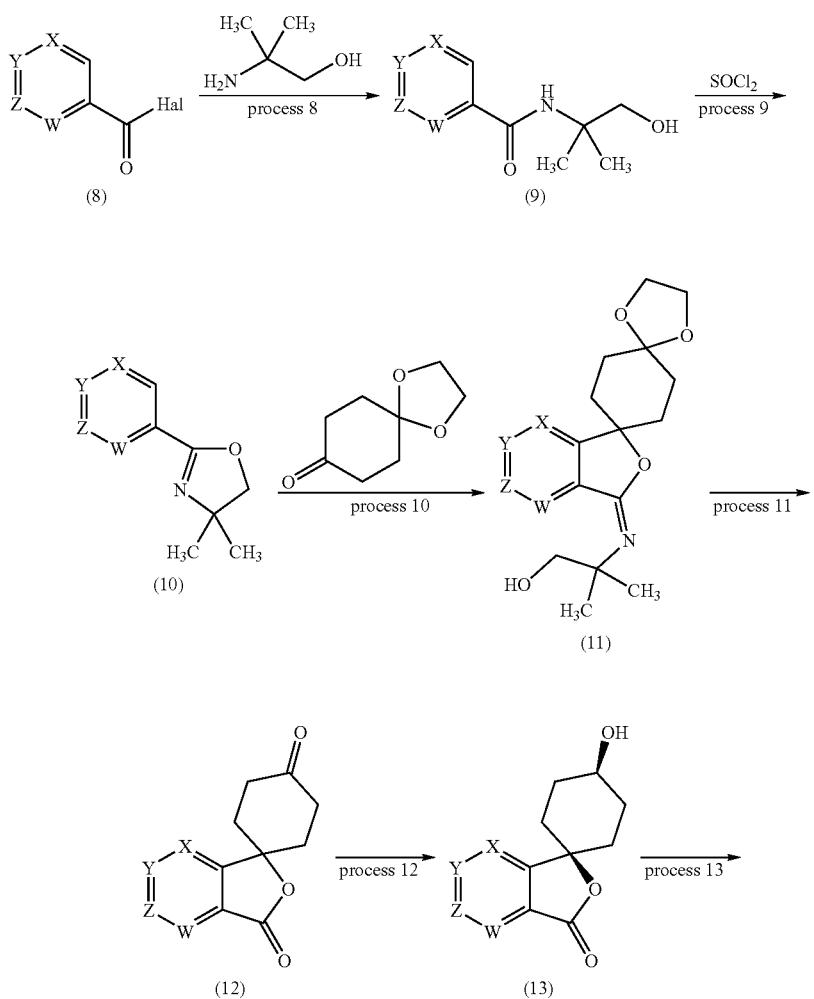

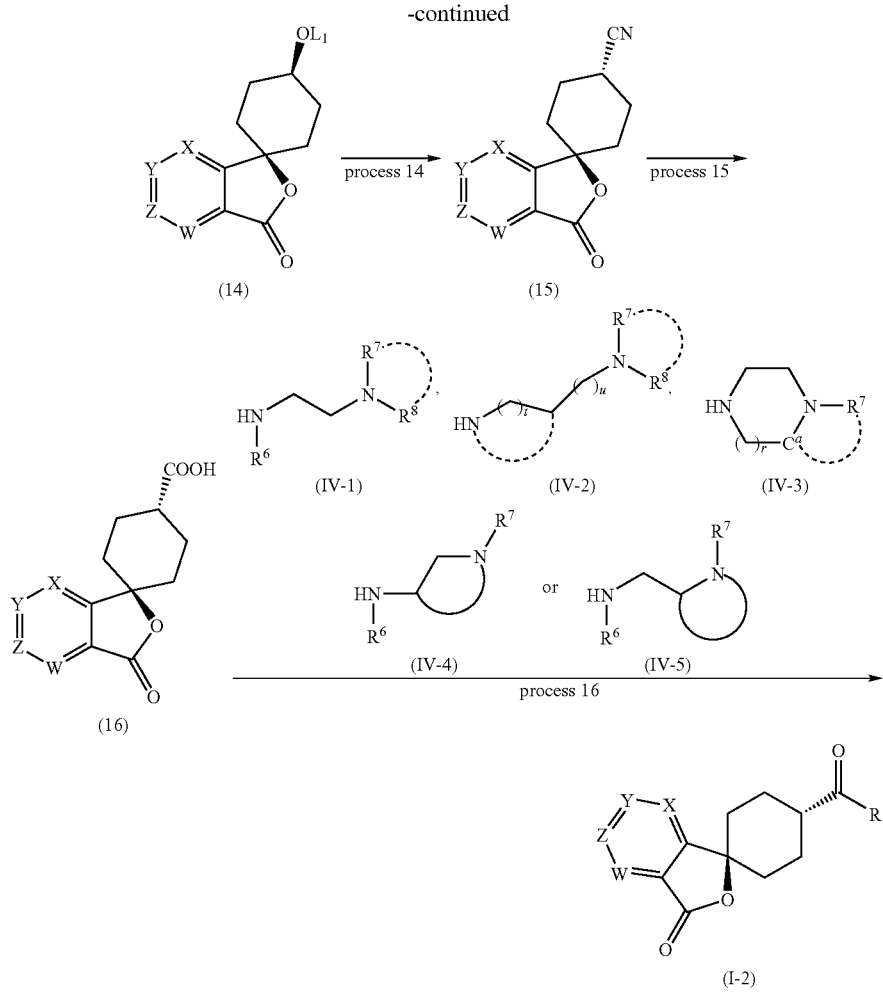

[wherein the symbols have the same meanings as above].
(Step 8)

This step is a process for producing a compound (9) by reacting a compound (8) with 1,1-dimethyl-2-hydroxyethylamine in the presence of a base.

The base to be used includes, for example, triethylamine, trimethylamine, N,N-diisopropylethylamine, N-methylmorpholine, pyridine et al. Of those, preferred are triethylamine, N,N-diisopropylethylamine, pyridine et al.

The amount of the base may be generally from 1 to 10 equivalents relative to one equivalent of the compound (8), preferably from 1 to 3 equivalents.

The reaction temperature may be generally from −78° C. to 100° C., preferably from 0° C. to 50° C.

The reaction time may be generally from 10 minutes to 48 hours, preferably from 30 minutes to 24 hours.

Not specifically defined, the reaction solvent to be used in this step may be any one not interfering with the reaction. Concretely, it includes, for example, chloroform, methylene chloride, 1,2-dichloroethane, THF, ethyl acetate, acetonitrile, 1,4-dioxane, toluene, dimethoxyethane et al. Preferred are chloroform, methylene chloride, THF et al.

Thus obtained, the compound (9) may be isolated and purified through any ordinary isolation and purification method of, for example, concentration, concentration under reduced pressure, crystallization, solvent extraction, repre-cipitation or chromatography, or not subjected to isolation and purification, it may be subjected to the next step.

(Step 9)

This step is a process for producing a compound (10) by reacting the compound (9) with thionyl chloride.

In place of thionyl chloride, also usable is sulfuryl chloride or phosphorus oxychloride et al.

The amount of thionyl chloride to be used may be generally from 1 to 10 equivalents relative to one equivalent of the compound (9), preferably from 1 to 3 equivalents.

The reaction temperature may be generally from 0° C. to 100° C., preferably from 0° C. to 50° C.

The reaction time may be generally from 10 minutes to 48 hours, preferably from 10 minutes to 24 hours.

Not specifically defined, the reaction solvent to be used in this step may be any one not interfering with the reaction. For example, it includes benzene, methylene chloride, 1,2-dichloromethane et al.

Thus obtained, the compound (10) may be isolated and purified through any ordinary isolation and purification method of, for example, concentration, concentration under reduced pressure, crystallization, solvent extraction, repre-cipitation or chromatography, or not subjected to isolation and purification, it may be subjected to the next step.

(Step 10)

This step is a process for producing a compound (11) by reacting the compound (10) with 1,4-cyclohexanedione monomethylene ketal, in the presence of a base.

The base includes, for example, butyl lithium, lithium 2,2,6,6-tetramethylpiperidide et al. Butyl lithium is preferred.

The amount of the base to be used may be generally from 1 to 10 equivalents relative to one equivalent of the compound (10), preferably from 1 to 3 equivalents.

The amount of 1,4-cyclohexanedione monomethylene ketal to be used may be generally from 1 to 10 equivalents relative to one equivalent of the compound (10), preferably from 1 to 3 equivalents.

The reaction temperature may be generally from −78° C. to 100° C., preferably from −78° C. to 50° C.

The reaction time may be generally from 10 minutes to 24 hours, preferably from 10 minutes to 12 hours.

The reaction solvent to be used in this step may be any one not interfering with the reaction, and includes, for example, THF, diethyl ether, tert-butyl methyl ether et al. Of those, preferred is THF.

Thus obtained, the compound (11) may be isolated and purified through any ordinary isolation and purification method of, for example, concentration, concentration under reduced pressure, solvent extraction, crystallization, reprecipitation or chromatography, or not subjected to isolation and purification, it may be subjected to the next step.

(Step 11)

This step is a process for producing a compound (12) by reacting the compound (11) with an acid.

The usable acid includes sulfuric acid, hydrochloric acid, paratoluenesulfonic acid, trifluoroacetic acid et al.

The amount of the acid to be used may be generally from 0.1 to 1000 equivalents relative to one equivalent of the compound (11), preferably from 0.1 to 10 equivalents.

The reaction temperature may be generally from 0° C. to 200° C., preferably from 20° C. to 100° C.

The reaction time may be generally from 1 hour to 72 hours, preferably from 1 hour to 48 hours.

The reaction solvent to be used in this step may be any one not interfering with the reaction, and includes, for example, water, acetone, THF, 1,4-dioxane et al. Of those, preferred are acetone, THF et al.

Thus obtained, the compound (12) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 12)

This step is a process for producing a compound (13) by reducing the compound (12).

The reaction in this step may be attained in the same manner as in the above step 3, or according to a method similar to it, or a combination of the method with an ordinary method.

Thus obtained, the compound (13) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 13)

This step is a process for producing a compound (14) by reacting the compound (13) with a compound $L_1$-Cl, in the presence of a base.

The reaction in this step may be attained in the same manner as in the above step 4, or according to a method similar to it, or a combination of the method with an ordinary method.

Thus obtained, the compound (14) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 14)

This step is a process for producing a compound (15) by reacting the compound (14) with a cyano compound.

The reaction in this step may be attained in the same manner as in the above step 5, or according to a method similar to it, or a combination of the method with an ordinary method.

Thus obtained, the compound (15) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 15)

This step is a process for producing a compound (16) by hydrolyzing the compound (15).

The reaction in this step may be attained in the same manner as in the above step 6, or according to a method similar to it, or a combination of the method with an ordinary method.

Thus obtained, the compound (16) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 16)

This step is a process for producing a compound (I-2) of the invention by reacting the compound (16) with a compound (IV-1), (IV-2), (IV-3), (IV-4) or (IV-5).

The reaction in this step may be attained in the same manner as in the above step 7, or according to a method similar to it, or a combination of the method with an ordinary method.

Compound (IV-1) includes, for example, N-methyl-N-(piperidinoethyl)amine, N-methyl-N-(pyrrolidinoethyl)amine, 1-(2-aminoethyl)piperidine, 1-(2-aminoethyl)pyrrolidine, N,N,N'-trimethylethylenediamine, N-cyclohexyl-N,N'-dimethylethylenediamine, N-ethyl-N-(piperidinoethyl)amine et al.

Compound (IV-2) includes, for example, (S)-1-(2-pyrrolidinylmethyl)pyrrolidine, (S)-1-(2-pyrrolidinylmethyl)piperidine, (S)-1-(2-piperidinylmethyl)piperidine or (S)-1-(2-piperidinylmethyl)pyrrolidine et al.

Compound (IV-3) includes, for example, 1-methylpiperazine, 1-isobutylpiperazine, 1-cyclopentylpiperazine, (R)-octahydropyrrolo[1,2-a]pyrazine or 1-ethyl-(3S)-methylpiperazine et al.

Compound (IV-4) includes, for example, N-(1-cyclopentyl-3-pyrrolidinyl)-N-methylamine or N-(1-isobutyl-3-pyrrolidinyl)-N-methylamine et al.

Compound (IV-5) includes, for example, 1-(1-isopropylpyrrolidin-2-yl)-N-methyl-methaneamine et al.

Thus obtained, the compound (I-2) of the invention may be isolated and purified through any ordinary isolation and purification method of, for example, concentration, concentration under reduced pressure, solvent extraction, crystallization, reprecipitation or chromatography.

The compounds (I-3), (I-4) and (I-5) of the invention may be produced, for example, according to the following method:

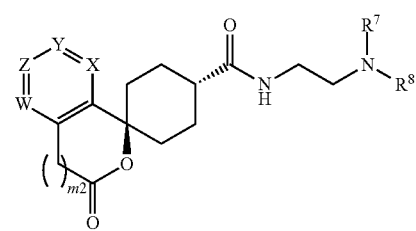

(I-1-1)

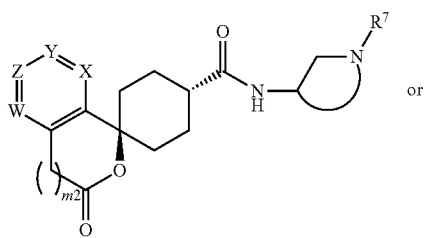

(I-1-2) or

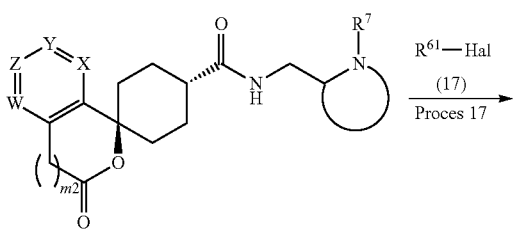

(I-1-3)

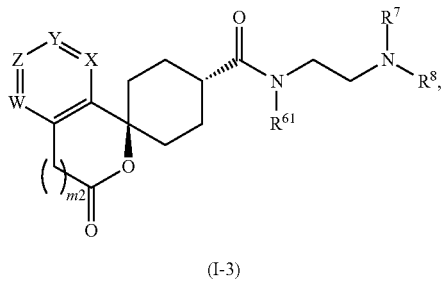

(I-3)

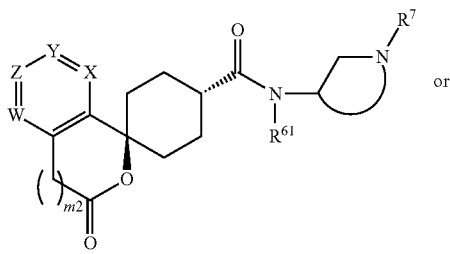

(I-4) or

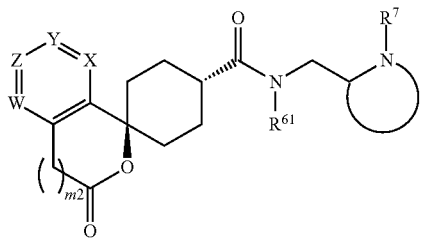

(I-5)

[wherein $R^{61}$ represents a lower alkyl group; Hal represents a halogen atom; and the other symbols have the same meanings as above].

(Step 17)

This step is a process for producing a compound (I-3), (I-4) or (I-5) of the invention by reacting the compound of formula (I-1-1), (I-1-2) or (I-1-3) of the invention, which is within the scope of the above-mentioned formula (I-1), with a compound (17) in the presence of a base.

The usable base includes, for example, sodium hydride, potassium hydride, calcium hydride, butyl lithium et al. Of those, preferred is NaH.

The amount of the base to be used may be generally from 1 to 10 equivalents relative to one equivalent of the compound (I-1-1), (I-1-2) or (I-1-3), preferably from 1 to 3 equivalents.

Concretely, the usable compound (17) includes, for example, ethyl iodide, methyl iodide, methyl trifluoromethylsulfonate, methyl methylsulfonate, methyl paratoluenesulfonate, methyl bromide, ethyl bromide et al.

The amount of the compound (17) to be used may be generally from 1 to 10 equivalents relative to one equivalent of the compound (I-1-1), (I-1-2) or (I-1-3), preferably from 1 to 3 equivalents.

Not specifically defined, the reaction solvent to be used in this step may be any one not interfering with the reaction. For example, it includes N,N-dimethylformamide, THF et al.

The reaction temperature may be generally from −78° C. to 100° C., preferably from 0° C. to 50° C.

The reaction time may be generally from 10 minutes to 48 hours, preferably from 10 minutes to 24 hours.

Thus obtained, the compound (I-3), (I-4) or (I-5) may be isolated and purified through any ordinary isolation and purification method of, for example, concentration, concentration under reduced pressure, crystallization, solvent extraction, reprecipitation or chromatography.

The compound (I-6) of the invention may be obtained, for example, according to the following method:

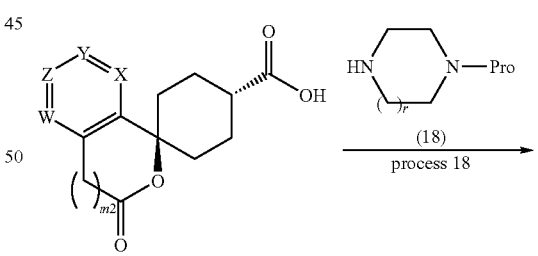

(7)

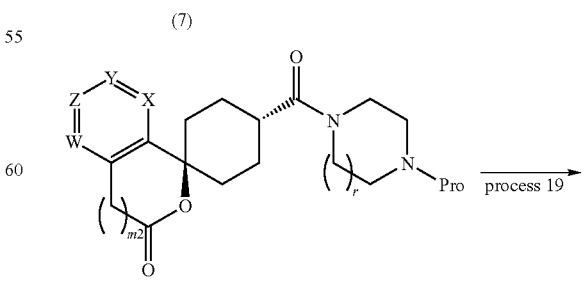

(19)

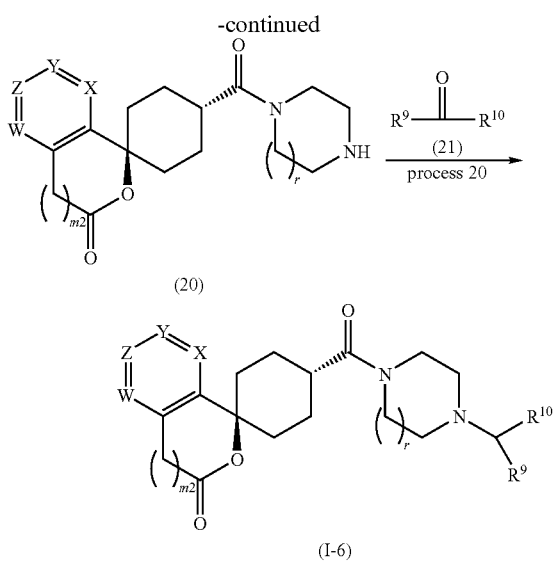

[wherein Pro represents a protective group for an amino group; $R^9$ represents a hydrogen atom, or a lower alkyl group; $R^{10}$ represents a hydrogen atom, a lower alkyl group, an aryl group or a heteroaryl group, or $R^9$ and $R^{10}$ may together form a 3- to 9-membered cycloalkyl group; and the other symbols have the same meanings as above].

(Step 18)

This step is a process for producing a compound (19) by reacting the above-mentioned compound (7) with a compound (18).

The reaction in this step may be attained in the same manner as in the above step 7, or according to a method similar to it, or a combination of the method with an ordinary method.

The usable compound (18) includes, for example, 1-Boc-piperazine, 1-Boc-homopiperazine, 1-benzyloxycarbonyl-piperazine, 1-acetylpiperazine, 1-benzoylpiperazine, 1-benzylpiperazine et al.

Thus obtained, the compound (19) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 19)

This step is a process for producing a compound (20) by removing the amino-protective group from the compound (19) obtained in the above step 18.

The amino-protective group may be removed according to a method described in literature (for example, Protective Groups in Organic Synthesis, by T. W. Green, 2nd Ed., John Wiley & Sons, 1991), or a method similar to it, or a combination of the method with an ordinary method.

Thus obtained, the compound (20) may be isolated and purified through any ordinary isolation and purification method of, for example, concentration, concentration under reduced pressure, crystallization, solvent extraction, reprecipitation or chromatography, or not subjected to isolation and purification, it may be subjected to the next step.

(Step 20)

This step is a process for producing a compound (I-6) of the invention by reacting the compound (20) obtained in the above step 18 with a compound (21).

The reaction in this step is so-called reductive alkylation, in which the compound (20) is reacted with a compound (21) in the presence of a base and a reducing agent to give a compound (I-6) of the invention.

The usable compound (21) includes, for example, cyclobutanone, cyclopentanone, cyclohexanone, cycloheptanone, acetone, 3-pentanone, 2-butanone, 3-methyl-2-butanone, 3-hexanone, formaldehyde, acetaldehyde, propionaldehyde, isobutylaldehyde et al.

The amount of the compound (21) to be used may be generally from 1 to 10 equivalents relative to one equivalent of the compound (20), preferably from 1 to 3 equivalents.

The usable base includes, for example, triethylamine, trimethylamine, N,N-diisopropylethylamine, N-methylmorpholine, N-methylpyrrolidine, N-methylpiperidine et al.

The amount of the base to be used may be generally from 0 to 5 equivalents relative to one equivalent of the compound (20), preferably from 0 to 2 equivalents.

The usable reducing agent includes, for example, $ZnCl_2$—$NaBH_3CN$, acetic acid-$NaBH_3CN$, acetic acid-NaBH$(OAc)_3$, sodium borohydride et al. Of those, preferred are $ZnCl_2$—$NaBH_3CN$, acetic acid-$NaBH_3CN$ et al.

The amount of the reducing agent to be used may be generally from 1 to 20 equivalents relative to one equivalent of the compound (20), preferably from 1 to 5 equivalents.

Not specifically defined, the reaction solvent to be used in this step may be any one not interfering with the reaction, and concretely includes, for example, methanol, ethanol, chloroform, methylene chloride, THF, 1,4-dioxane et al. Of those, preferred are methanol, ethanol, methylene chloride.

The reaction temperature may be generally from 0° C. to 100° C., preferably from 0° C. to 50° C.

The reaction time may be generally from 10 minutes to 48 hours, preferably from 10 minutes to 24 hours.

Thus obtained, the compound (I-6) may be isolated and purified through any ordinary isolation and purification method of, for example, concentration, concentration under reduced pressure, crystallization, solvent extraction, reprecipitation or chromatography.

The compound (I-2-1) of the invention:

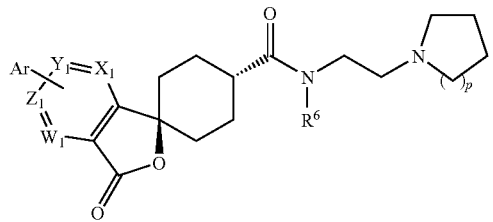

[wherein $X_1$, $Y_1$, $Z_1$ and $W_1$ each independently represent a methine group or a nitrogen atom, but all of $X_1$, $Y_1$, $Z_1$ and $W_1$ are not a methine group; Ar represents an aryl or heteroaryl group optionally substituted with a lower alkyl group, a lower alkoxy group, a halogen atom, a cyano group et al; p indicates from 0 to 4; and the other symbols are the same as above] may be produced according to the method mentioned below, for example, using a compound of a formula (A).

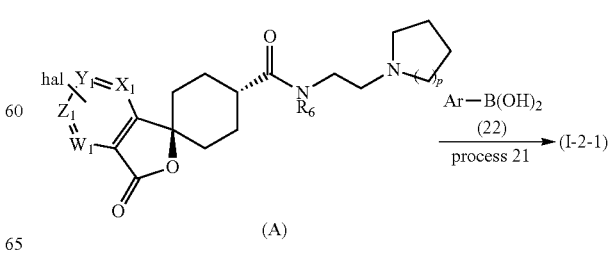

[wherein the symbols have the same meanings as above].

(Step 21)

This step is a process for producing a compound (I-2-1) of the invention by reacting the compound (A) with a compound (22) in the presence of a base and a palladium catalyst.

The base includes, for example, sodium carbonate, cesium carbonate, cesium fluoride, calcium carbonate, sodium hydride, sodium carbonate, potassium carbonate, potassium phosphate, potassium acetate, potassium tert-butoxide, triethylamine et al.

The amount of the base to be used may be generally from 0.1 to 20 equivalents relative to 1 equivalent of the compound (A), preferably from 1 to 5 equivalents.

The palladium catalyst includes, for example, tetrakistriphenylphosphine-palladium, dichlorobistriphenylphosphine-palladium, dichloro(1,1'-bis(diphenylphosphino)ferrocene)-palladium, palladium acetate et al.

The amount of the palladium catalyst to be used may be generally from 0.01 to 10 equivalents relative to 1 equivalent of the compound (A), preferably from 0.05 to 5 equivalents.

The compound (A) includes, for example, the compounds produced in Examples 1, 4, 32 and 33.

The compound (22) includes, for example, pyridin-3-ylboronic acid, pyridin-4-ylboronic acid, pyrimidin-5-ylboronic acid, 2-methoxypyrimidin-5-ylboronic acid, 2-methoxypyridin-5-ylboronic acid, 2-methylpyridin-5-ylboronic acid, phenylboronic acid, (1-methyl-1H-pyrazol-4-yl)boronic acid et al.

Not specifically defined, the reaction solvent may be any one not interfering with the reaction, and includes, for example, ethylene glycol dimethyl ether, DMF, toluene, THF, 1,4-dioxane, benzene, acetone, methanol et al.

The reaction temperature may be generally from 0° C. to the reflux temperature of the reaction solvent, preferably from room temperature to 150° C.

The reaction time may be generally from 0.1 hours to 72 hours, preferably from 0.5 hours to 12 hours.

The compound (I-2-1) may also be produced according to the following method:

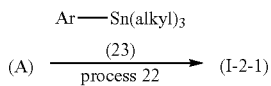

[wherein the symbols are the same as above].

(Step 22)

This step is a process for producing a compound (I-2-1) by reacting the compound (A) with a compound (23) in the presence of lithium chloride and a palladium catalyst.

The amount of lithium chloride to be used may be generally from 0.01 to 10 equivalents relative to 1 equivalent of the compound (A), preferably from 0.05 to 5 equivalents.

The palladium catalyst includes, for example, tetrakistriphenylphosphine-palladium, dichlorobistriphenylphosphine-palladium, dichloro(1,1'-bis(diphenylphosphino)ferrocene)palladium, palladium acetate et al. The amount of the palladium catalyst may be generally from 0.01 to 10 equivalents relative to 1 equivalent of the compound (A), preferably from 0.05 to 5 equivalents.

The compound (23) includes, for example, 2-(tri-n-butyltin)pyrazine, 2-(tri-n-butyltin)pyridine et al.

The amount of the compound (23) may be generally from 0.1 to 50 equivalents relative to 1 equivalent of the compound (A), preferably from 1 to 10 equivalents.

Not specifically defined, the reaction solvent may be any one not interfering with the reaction, and includes, for example, DMF, toluene, THF, 1,4-dioxane, benzene, acetone et al.

The reaction temperature may be generally from 0° C. to the reflux temperature of the reaction solvent, preferably from room temperature to 150° C.

The reaction time may be generally from 0.1 hours to 72 hours, preferably from 0.5 hours to 12 hours.

Thus obtained, the compound (I-2-1) may be isolated and purified through any ordinary isolation and purification method of, for example, concentration, concentration under reduced pressure, crystallization, solvent extraction, reprecipitation or chromatography.

A compound of a formula (I-2-2) of the invention:

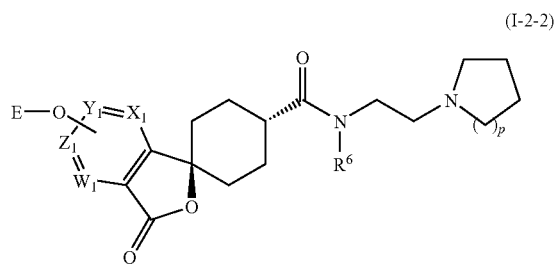

[wherein E represents a lower alkyl group having from 1 to 6 carbon atoms, or Ar; and the other symbols are the same as above] may be produced, for example, according to the following method:

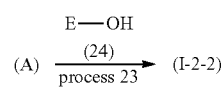

(Step 23)

This step is a process for producing a compound (I-2-2) by reacting the compound (A) with a compound (24) in the presence of a base.

The usable base includes, for example, cesium carbonate, potassium carbonate, sodium carbonate, sodium hydride et al.

The amount of the base to be used may be generally from 0.1 to 20 equivalents relative to 1 equivalent of the compound (A), preferably from 1 to 5 equivalents.

The compound (24) includes, for example, methanol, ethanol, propanol, butanol and benzyl alcohol et al when E is a lower alkyl group, and includes phenol, 2-hydroxypyridine and 3-hydroxypyridine et al when E is Ar.

The amount of the compound (24) to be used may be generally from 0.1 to 50 equivalents relative to 1 equivalent of the compound (A), preferably from 1 to 10 equivalents. Not specifically defined, the reaction solvent may be any one not interfering with the reaction, and includes, for example, DMF, acetone, 1,4-dioxane, benzene, toluene, N-methyl-2-pyrrolidone, THF et al.

The reaction temperature may be generally from 0° C. to the reflux temperature of the reaction solvent, preferably from room temperature to 150° C.

The reaction time may be generally from 0.1 hours to 72 hours, preferably from 0.5 hours to 12 hours.

Thus obtained, the compound (I-2-2) may be isolated and purified through any ordinary isolation and purification method of, for example, concentration, concentration under reduced pressure, crystallization, solvent extraction, reprecipitation or chromatography.

A compound (I-2-3) of the invention may be produced, for example, according to the following method:

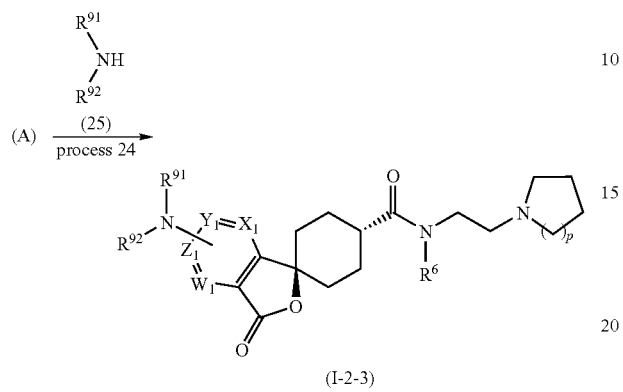

(I-2-3)

[wherein $R^{91}$ and $R^{92}$ are the same or different, each representing a hydrogen atom or a lower alkyl group, or $R^{91}$ and $R^{92}$, taken together with the nitrogen atom to which they bond, form a 4- to 8-membered nitrogen-containing aliphatic ring optionally having substituents; and the other symbols are the same as above].

(Step 24)

This step is a process for producing a compound (I-2-3) by reacting the compound (A) with a compound (25) in the presence or absence of a base.

The base includes, for example, potassium carbonate, cesium carbonate, sodium hydride, potassium phosphate, sodium carbonate et al.

The amount of the base, when used, may be generally from 0.1 to 20 equivalents relative to 1 equivalent of the compound (A), preferably from 1 to 5 equivalents.

The amount of the compound (25) to be used may be generally from 0.1 to 50 equivalents relative to 1 equivalent of the compound (A), preferably from 1 to 10 equivalents.

Not specifically defined, the reaction solvent may be any one not interfering with the reaction, and includes, for example, DMF, N-methyl-2-pyrrolidone, toluene, benzene, 1,4-dioxane, THF et al.

The reaction temperature may be generally from 0° C. to the reflux temperature of the reaction solvent, preferably from room temperature to 150° C.

The reaction time may be generally from 0.1 hours to 72 hours, preferably from 0.5 hours to 12 hours.

The compound (25) includes dimethylamine, morpholine et al.

Thus obtained, the compound (I-2-3) may be isolated and purified through any ordinary isolation and purification method of, for example, concentration, concentration under reduced pressure, crystallization, solvent extraction, reprecipitation or chromatography.

In the step 21, the step 22 and the step 23, preferred is a case where in $X_1$, $Y_1$, $Z_1$ and $W_1$, the nitrogen atom is adjacent to the carbon atom to which Hal bonds.

A compound (I-7), (I-8) or (I-9) of the invention:

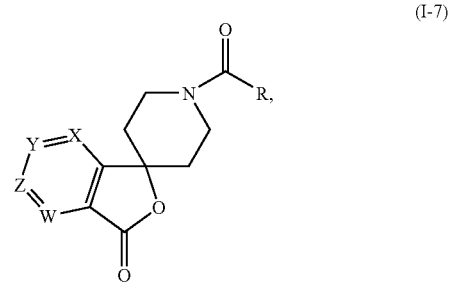

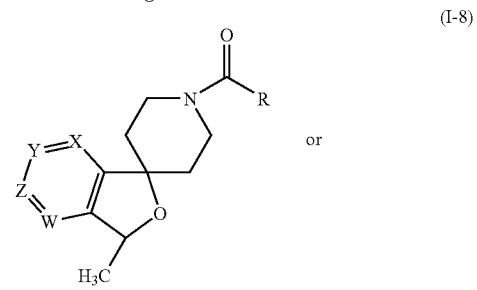

or

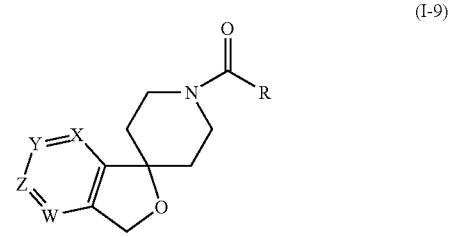

[wherein the symbols have the same meanings as above] may be produced according to a method described in literature (for example, Journal of Organic Chemistry, 1976, Vol. 41, No. 15, pp. 2628-2633), or a method similar to it, or a combination of the method with an ordinary method.

A compound (I-10) of the invention:

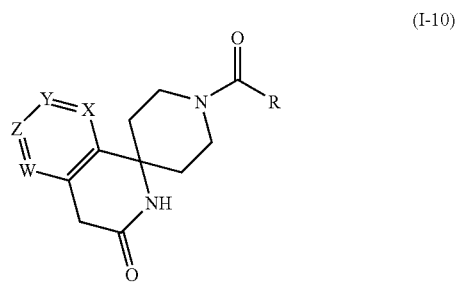

[wherein the symbols have the same meanings as above] may be produced according to a method described in literature (for example, WO95/28389), or a method similar to it, or a combination of the method with an ordinary method.

In case where the formula (I), or the formula (I-1), (I-2), (I-3), (I-4), (I-5), (I-6), (I-7), (I-8), (I-9) or (I-10) which is within the scope of the formula (I) has a protective group in X, Y, Z or W, the protective group may be removed to convert the starting compound into the objective compound. The protective group may be removed according to a method described in literature (for example, Protective Groups in Organic Synthesis, by T. W. Green, 2nd Ed., John Wiley & Sons, 1991), or a method similar to it, or a combination of the method with an ordinary method.

These compounds may be converted into salts or esters acceptable as medicines, according to any ordinary method. On the contrary, the salts and the esters may be converted into free compounds also according to any ordinary method.

The carbamoyl-substituted spiro derivatives of the invention may exit as pharmaceutically-acceptable salts, and such salts may be produced from the compounds of the above formula (I), or the above formula (I-1), (I-1-1), (I-1-2), (I-1-3), (I-2), (I-2-1), (I-2-2), (I-2-3), (I-2-4), (I-2-5), (I-3), (I-4), (I-5), (I-6), (I-7), (I-8), (I-9) or (I-10) which is within the scope of the formula (I). These compounds may be formed into salts or esters acceptable as medicines according to any ordinary method, and on the contrary, the salts and the esters may be converted into free compounds also according to any ordinary method.

The acid addition salts include, for example, hydrohalides (e.g., hydrochlorides, hydrofluorides, hydrobromides, hydroiodides et al), inorganic acid salts (e.g., nitrates, perchlorates, sulfates, phosphates, carbonates et al), lower alkyl-sulfonates (e.g., methanesulfonates, trifluoromethane-sulfonates, ethanesulfonates et al), arylsulfonates (e.g., benzenesulfonates, p-toluenesulfonates et al), organic acid salts (e.g., fumarates, succinates, citrates, tartrates, oxalates, maleates et al), and amino acid salts (e.g., glutamates, aspartates et al).

The base addition salts include, for example, alkali metal salts (e.g., sodium salts, potassium salts et al), alkaline earth metal salts (e.g., calcium salts, magnesium salts et al), ammonium salts, and organic base (e.g., guanidine, triethylamine, dicyclohexylamine et al) addition salts. Further, the compounds of the invention may be in any form of hydrates or solvates of their free compounds or salts.

The compounds of the formula (I) and their pharmaceutically-acceptable salts may be administered orally or parenterally.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin et al.

Combined with such additives, the compound of the invention may be formulated into solid preparations (e.g., tablets, capsules, granules, powders, suppositories) and liquid preparations (e.g., syrups, elixirs, injections). These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

FORMULATION EXAMPLE 1

10 parts of the compound of Example 1 to be described hereinunder, 15 parts of heavy magnesium oxide and 75 parts of lactose are uniformly mixed to prepare a powdery or granular preparation having a particle size of at most 350 µm. The preparation is encapsulated to give capsules.

FORMULATION EXAMPLE 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 µm.

FORMULATION EXAMPLE 3

A granular preparation is prepared in the same manner as in Formulation Example 2. 96 parts of the granular preparation is mixed with 3 parts of calcium stearate, and shaped under compression into tablets having a diameter of 10 mm.

FORMULATION EXAMPLE 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time during the period of treatment, either as one preparation or as divided different preparations. The combination of the compound of the invention with any other drug effective for treatment of metabolic disorders or dietary disorders includes, in principle, combinations thereof with any and every drug effective for treatment of metabolic disorders or dietary disorders.

The compounds of the invention may also be combined with any other drug effective for hypertension, obesity-related hypertension, hypertension-related disorders, cardiomegaly, left ventricle hypertrophy, metabolic disorders, obesity, obesity-related disorders (these are hereinafter referred to as "co-drugs"). Such co-drugs may be administered at the same time or at different times or successively in order in prevention or treatment of the above-mentioned disorders. When the compound of the invention is used simultaneously with one or more co-drugs, then it may be in a pharmaceutical composition for one-dose administration. However, in such combination therapy, the composition containing the compound of the invention and the co-drug may be administered to subjects simultaneously, or separately or successively. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: 1) A compound of the invention is combined with a co-drug to give a single preparation for single administration; 2) a compound of the invention and a co-drug are separately formulated into different two preparations, and the two preparations are simultaneously administered in one administration route; 3) a compound of the invention and a co-drug are separately formulated into different two preparations, and they are administered at different times in one and the same administration route; 4) a compound of the invention and a co-drug are separately formulated into different two preparations, and they are administered at the same time in two different administration routes; 5) a compound of the invention and a co-drug are separately formulated into different two preparations, and they are administered at different times in different administration routes (for example, a compound of the invention and a co-drug are administered in that order, or in an order contrary to this). The blend ratio of the compound of the invention and the co-drug may be suitably determined depending on the administration subject, the administration route, and the disease for the administration.

The co-drugs usable in the invention includes therapeutical drugs for diabetes, therapeutical drugs for hyperlipemia, therapeutical drugs for hypertension, and anti-obesity drugs. Two or more such co-drugs may be combined in any desired ratio.

The therapeutical drugs for diabetes includes, for example, the following:

1) PPAR (peroxisome proliferator-activated receptor)-γ agonists such as glitazones (e.g., ciglitazone, darglitazone, englitazone, isaglitazone, MCC-555 et al, pioglitazone, rosiglitazone, troglitazone, BRL49653, CLX-0921, 5-BTZD), GW-0207, LG-100641, LY-300512 et al;
2) biguanides such as metformin, buformin, phenformin et al;
3) protein tyrosine phosphatase 1B inhibitors;
4) sulfonylureas such as acetohexamide, chloropropamide, diabinese, glibenclamide, glipizide, glyburide, glimepiride, glicilazide, glipentide, gliquidone, glisolamide, trazamide, tolubutamide et al;
5) meglitinides such as repaglinide, nateglinide et al;
6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14 et al;
7) α-amylase inhibitors such as tendamistat, trestatin, A13688 et al;
8) insulin secretion promoters such as linogliride, A-4166 et al;
9) fatty acid oxidation inhibitors such as clomoxir, etomoxir et al;
10) A2 antagonists such as midaglizole, isaglidole, deriglidole, idazoxan, earoxan, fluparoxan et al;
11) insulin or insulin mimetix such as biota, LP-100, novalapid, insulin detemir, insulin lispro, insulin glargine, insulin zinc, Lys-Pro-insulin, GLP-1 (73-7), GLP1 (7-36)-$NH_2$ et al;
12) non-thiazolidinediones such as JT-501, farglitazar et al;
13) PPARα/γ dual-agonists such as CLX-0940, GW-1536, GW-1929, GW-2433, KRP-297, L-796449, LR-90, SB219994 et al;
14) other insulin sensitizes, and
15) VPAC2 receptor agonists.

The therapeutical drugs for hyperlipemia include, for example, the following:

1) bile acid absorption promoters such as cholesterylamine, colesevelem, colestipol, crosslinked dextran dialkylaminoalkyl derivatives, Colestid®, LoCholest®, Questran® et al;
2) HMG-CoA reductase inhibitors such as atorvastatin, itavastatin, fluvastatin, lovastatin, pravastatin, rivastatin, rosuvastatin, simvastatin, ZD-4522 et al;
3) HMG-CoA synthase inhibitors;
4) cholesterol absorption inhibitors such as snatol ester, β-sitosterol, sterol glucoside, ezetimibe et al;
5) ACAT (acyl-CoA.cholesterol acyltransacylase) inhibitors such as avasimibe, eflucimibe, KY-505, SMP-709 et al;
6) CETP inhibitors such as JTT705, torcetrapib, CP532632, BAY-63-2149, SC-591, SC-795 et al;
7) squalane synthetase inhibitors;
8) antioxidants such as probucol;
9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®) et al;
10) FXR receptor antagonists such as GW-4064, SR-103912 et al;
11) LXR receptor agonists such as GW3965, T9013137, XTCO-179628 et al;
12) lipoprotein synthesis inhibitors such as niacin et al;
13) renin-angiotensin system inhibitors;
14) PPARδ partial agonists;
15) bile acid re absorption inhibitors such as BARA1453, SC435, PHA384640, S-435, AZD7706 et al;
16) PPARδ agonists such as GW501516, GW590735 et al;
17) triglyceride synthesis inhibitors;
18) MTTP (microsomic triglyceride transportation) inhibitors such as inplitapide, LAB687, CP346086 et al;
19) transcription modifying factors;
20) squalane epoxidase inhibitors;
21) LDL (low-density lipoprotein) receptor derivatives,
22) platelet agglutination inhibitors;
23) 5-LO (5-lipoxygenase)/FLAP (5-lipoxygenase activated protein) inhibitors; and
24) niacin receptor agonists.

The therapeutical drugs for hypertension include, for example, the following:

1) thiazide diuretics such as chlorothialidon, chlorothiazide, dichlorofenamide, hydrofluorothiazide, indapamide, hydrochlorothiazide et al; loop diuretics such as bumetanide, ethacrynic acid, flosemide, tolusemide et al; sodium diuretics such as amyloride, triamuteren et al; aldosterone antagonist diuretics such as spironolactone, epilenone et al;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tertatolol, tilisolol, timolol et al;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil et al;
4) angiotensin converting enzyme inhibitors such as benazepril, captopril, cilazapril, delapril, enalapril, fosinopril, imidapril, rosinopril, moexipril, quinapril, quinaprilat, ramipril, perindopril, perindoropril, quanipril, spirapril, tenocapril, trandolapril, zofenopril et al;
5) neutral endopeptidase inhibitors such as omapatrilat, cadoxatril, ecadotril, fosidotril, sampatrilat, AVE7688, ER4030 et al;
6) endothelin antagonists such as tezosentan, A308165, YM62899 et al;
7) vasodilators such as hydraladine, clonidine, minoxidil, nicotinyl alcohol et al;
8) angiotensin II receptor antagonists such as candesartan, eporsartan, iribesartan, losartan, pratosartan, tasosartan, telmisartan, valsartan, EXP-3137, FI6828K, RNH6270 et al;
9) α/β adrenalin blockers such as nipradilol, arotinolol, amoslalol et al;
10) α1 blockers such as terazosin, urapidil, purazosin, bunazosin, trimazosin, doxazosin, naphthopidil, indolamin, WHIP164, XENO010 et al;
11) α2 agonists such as lofexidine, tiamenidine, moxonidine, rilmenidine, guanobenz et al; and
12) aldosterone inhibitors.

The anti-obesity drugs include, for example, the following:
1) 5HT (serotonin) transporter inhibitors such as paroxetine, fluoxetine, fenfluramine, fluvoxamine, sertraline, imipramine et al;
2) NE (norepinephrine) transporter inhibitors such as GW320659, desipramine, talsupram, nomifensin et al;
3) CB-1 (cannabinoid-1 receptor) antagonists/inverse-agonists such as rimonabant (Sanofi Synthelabo), SR-147778 (Sanofi Synthelabo), BAY-65-2520 (Bayer), SLV-319 (Sorbay), as well as compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546 et al;
4) ghrelin antagonists such as compounds disclosed in WO01/87355, WO02/08250 et al;
5) histamine (H3) receptor antagonists/inverse-agonists such as thioperamide, 3-(1H-imidazol-4-yl)propyl-N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives Sasse, A. et al., Arch. Pharm. (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000)) et al;
6) MCH-1R (melamine concentrating hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027 and JP-A-2001-226269 et al;
7) MCH-2R (melamine concentrating hormone receptor 2) agonists/antagonists;
8) NPY1 (neuropeptide Y Y1) antagonists such as BIBP3226, J-115814, BIB03304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528 et al;
9) NPY5 (neuropeptide Y Y5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326,375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312 (2000) et al;
10) leptins such as human recombinant leptin (PEG-OB, Hoffman La Roche), recombinant methionylleptin (Amgen) et al;
11) leptin derivatives such as compounds disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519 and WO96/23520 et al;
12) opioid antagonists such as narlefen (Revex®), 3-methoxynaltorexon, naloxone, naltorexon, compounds disclosed in WO00/21509 et al;
13) Orexin antagonists such as SB-334867A, and other compounds disclosed in WO01/96302, WO01/68609, WO02/51232, WO02/51838 and WO03/023561 et al;
14) BRS3 (bonbesin receptor subtype-3) agonists;
15) CCK-A (cholecystokinin A) agonists such as AR-R15849, GI-181771, JMV-180, A-71378, A-71623, SR-146131, and other compounds disclosed in U.S. Pat. No. 5,739,106 et al;
16) CNTF (ciliary neurotrophic factors) such as GI-181771 (Glaxo-Smith Kline), SR146131 (Sanofi Synthelabo), butabindide, PD170,292, PS149164 (Pfizer) et al;
17) CNTF derivatives such as axokine (Regeneron), and other compounds disclosed in WO94/09134, WO98/22128, WO99/43813 et al;
18) GHS (growth hormone secretion promoter receptor) agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888 et al;
19) 5HT2c (serotonin receptor-2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456 and WO02/40457 et al;
20) Mc3r (melanocortin-3 receptor) agonists;
21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847 et al;

22) monoamine re-uptake inhibitors such as sibutramine (Meridia®/Reductil®) and its salts, and other derivatives disclosed in U.S. Pat. Nos. 4,746,680, 4,806,570, 5,436,272, US Patent Application No. 2002/0006964, WO01/27068 and WO01/62341;

23) serotonin re-uptake inhibitors such as dexfenfluramine, fluoxetine, and other compounds disclosed in U.S. Pat. No. 6,365,633, WO01/27060 and WO01/162341 et al;

24) GLP 1 (glucagon-like peptide-1) agonists;

25) topiramate (Topimax®);

26) phytopharm compound 57 (e.g., CP644,673);

27) ACC2 (acetyl CoA carboxylase-2) inhibitors;

28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. Nos. 5,705,515, 5,451,677, WO01/74782 and WO02/32897 et al;

29) DGAT1 (diacylglycerol acyltransferase-1) inhibitors;

30) DGAT2 (diacylglycerol acyltransferase-2) inhibitors,

31) FAS (fatty acid synthase) inhibitors such as cerulenin, C75;

32) PDE (phosphodiesterase) inhibitors such as theophylline, pentoxiphylline zaprinast, sildenafil, aminone, milrinone, cilostamide, rolipram and cilomilast et al;

33) thyroid hormone-β agonists such as KB-2611 (KaroBio BMS), and other compounds disclosed in WO02/15845, JP-A 2000-256190 et al;

34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TT-NPB), retinoic acid, and other compounds disclosed in WO99/00123 et al;

35) acylestrogens such as oleoylestrone (disclosed in del Mar-Grasa, M. et al., Obesity Research, 9:202-9 (2001)), 36) glucocorticoid antagonists;

37) 11-β HSD1 (11-β-hydroxysteroid dehydrogenase-1) inhibitors such as BVT3498, BVT2733, and other compounds disclosed in WO01/90091, WO01/90090, WO01/90092 et al;

38) SCD1 (stearoyl-CoA desaturase-1) inhibitors;

39) DP-IV (dipeptidyl peptidase-IV) inhibitors such as isoleucine thiazolidine, valine pyrrolidide, NVP-DPP728, AF237, P93/01, TSL225, TMC-2A/2B/2C, FE999011, P93101/K364, VIP0177, SDZ274-444, and other compounds disclosed in WO03/004498, WO03/004496, EP 1258476, WO02/083128, WO02/062764, WO03/000250, WO03/002530, WO03/002531, WO03/002553, WO03/002593, WO03/000180 and WO03/000181 et al;

40) lipase inhibitors such as tetrahydroliptatin (Orlistat/Xenical®), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. Nos. 4,598,089, 4,452,813, 5,512,565, 5,391,571, 5,602,151, 4,405,644, 4,189,438 and 4,242,453 et al;

41) fatty acid transporter inhibitors;

42) dicarboxylate transporter inhibitors;

43) glucose transporter inhibitors;

44) phosphate transporter inhibitors;

45) melanocortin agonists such as melanotan II, and other compounds disclosed in WO99/64002 and WO00/746799 et al;

46) melanin concentrating hormone antagonists;

47) galanin antagonists;

48) CCK agonists;

49) corticotropin release hormones;

50) PDE3 (phosphodiesterase 3B) agonists.

The compounds of the invention may be combined with one or more of the above-mentioned co-drugs. The combination of the compound of the invention with one or more co-drugs selected from a group consisting of drugs for diabetes and drugs for hyperlipemia is useful for prevention or remedy of metabolic disorders. In particular, a combination of the compound of the invention with a drug for hypertension and an anti-obesity drug along with a drug for diabetes or a drug for hyperlipemia is useful for prevention or remedy of metabolic disorders owing to the synergistic effect thereof.

When the compounds of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Ordinary physicians, veterinarians and clinicians may readily determine the effective dose necessary for retarding, inhibiting or stopping the development of diseases.

EXAMPLES

The invention is described more concretely with reference to the following Examples, which, however, do not whatsoever restrict the invention.

For the thin-layer chromatography of the compounds in the Examples, used was a plate of Silicagel 60F$_{245}$ (Merck); and for detection, used was a UV detector. Wakogel™ C-300 (Wako Pure Chemicals) was used for the column silica gel; and LC-SORB™ SP-B-ODS (Chemco) or YMC-GEL™ ODS-AQ 120-S50 (Yamamura Chemical Laboratories) was for the reversed-phase column silica gel. Mass spectrum was determined according to an electrospray ionization (ESI) process, using QuattroII (Micromass).

In NMR spectrometry, dimethylsulfoxide was used for the internal standard in a heavy dimethylsulfoxide solution. Using a spectrometer of Gemini-200 (200 MHz; Varian), Gemini-300 (300 MHz; Varian), Mercury 400 (400 MHz; Varian) or Inova 400 (400 MHz; Varian), the sample was analyzed for the total δ value in ppm.

The meanings of the abbreviations in the following Examples are mentioned below.

i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d6: heavy dimethylsulfoxide The meanings of the abbreviations in nuclear magnetic resonance spectra are mentioned below.

s: singlet
d: doublet
dd: double-doublet
t: triplet
m: multiplet
br: broad
q: quartet
J: coupling constant
Hz: hertz Example 1

Trans-5'-chloro-3'-oxo-N-methyl-N-(2-pyrrolidin-1-ylethyl)-spiro[cyclohexane-1,1'-(3'H)-4'-azaisobenzofuran]-4-carboxamide

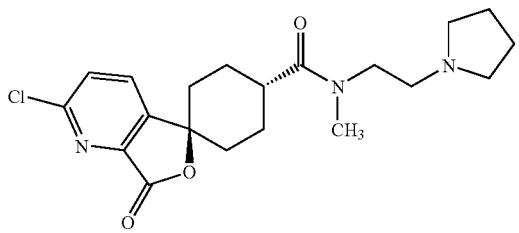

To a chloroform (15 mL) solution of trans-2'-chloro-3'-oxo-spiro[cyclohexane-1,1'-(3'H)-4'-azaisobenzofuran]-4-carboxylic acid (1.00 g) obtained in Reference Example 1 and N-methyl-N-(pyrrolidinoethyl)amine (546 mg), triethylamine (0.99 mL), 1-hydroxybenzotriazole (652 mg) and 1-ethyl-3-(3-(dimethylaminopropyl)carbodiimide hydrochloride (817 mg) were added, and stirred at room temperature for 6 hours. Aqueous saturated sodium bicarbonate solution was added to it, and extracted with ethyl acetate. The organic layer was washed with saturated saline water, then dried with sodium sulfate, filtered and concentrated under reduced pressure. The resulting residue was purified through silica gel column chromatography (Biotage Column NH, ethyl acetate/hexane=10% to 90%, gradient) to obtain the entitled compound (1.30 g, 93%) as a colorless oily substance.

$^1$HNMR (400 MHz, CDCl$_3$, δ): 1.71-2.16 (10H, m), 2.22-2.35 (2H, m), 2.51-2.73 (6H, m), 2.91-3.02 (1H, m), 2.99 (3H×1/2, s), 3.13 (3H×1/2, s), 3.49 (2H×1/2, t, J=7.3 Hz), 3.57 (2H×1/2, t, J=7.3 Hz), 7.56 (1H×1/2, d, J=8.0 Hz), 7.56 (1H×1/2, d, J=8.0 Hz), 8.07 (1H×1/2, d, J=8.0 Hz), 8.11 (1H×1/2, d, J=8.0 Hz).
Mass spectrum (ESI): 392.1 (M+H).

Example 2

Trans-3'-oxo-N-methyl-N-(2-piperidin-1-ylethyl)-spiro[cyclohexane-1,1'-(3'H)-4'-azaisobenzofuran]-4-carboxamide

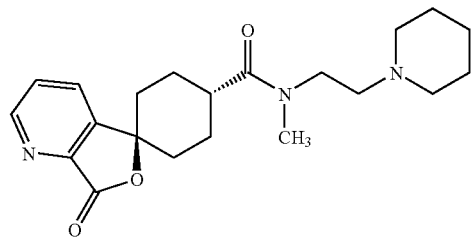

The entitled compound was obtained according to the method of Example 1 but starting from trans-3'-oxo-spiro[cyclohexane-1,1'-(3'H)-4'-azaisobenzofuran]-4-carboxylic acid and N-methyl-N-(piperidinoethyl)amine.

$^1$HNMR (400 MHz, CDCl$_3$, δ): 1.33-1.65 (6H, m), 1.78-2.11 (6H, m), 2.17-2.31 (2H, m), 2.33-2.50 (6H, m), 2.86-3.00 (1H, m), 2.95 (3H×1/2, s), 3.09 (3H×1/2, s), 3.43 (2H×1/2, t, J=6.9 Hz), 3.50 (2H×1/2, t, J=7.0 Hz), 7.45-7.54 (1H, m), 8.03-8.15 (1H, m), 8.84 (1H, d, J=4.7 Hz).
Mass spectrum (ESI): 372.2 (M+H).

Example 3

Trans-3'-oxo-N-methyl-N-(2-pyrrolidin-1-ylethyl)-spiro[cyclohexane-1,1'-(3'H)-4'-azaisobenzofuran]-4-carboxamide

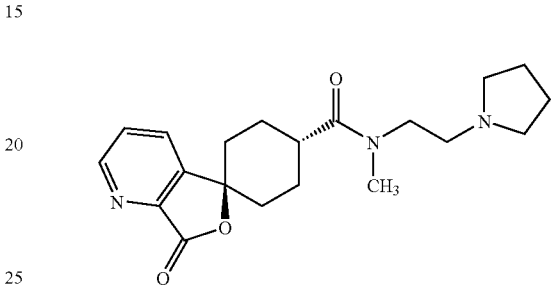

The entitled compound was obtained according to the method of Example 1 but starting from trans-3'-oxo-spiro[cyclohexane-1,1'-(3'H)-4'-azaisobenzofuran]-4-carboxylic acid and N-methyl-N-(pyrrolidinoethyl)amine.

$^1$HNMR (400 MHz, CDCl$_3$, δ): 1.67-2.11 (10H, m), 2.17-2.30 (2H, m), 2.47-2.69 (6H, m), 2.86-2.98 (1H, m), 2.96 (3H×1/2, s), 3.10 (3H×1/2, s), 3.47 (2H×1/2, t, J=7.5 Hz), 3.54 (2H×1/2, t, J=7.3 Hz), 7.46-7.54 (1H, m), 8.07 (1H×1/2, d, J=7.8 Hz), 8.12 (1H×1/2, d, J=7.8 Hz), 8.85 (1H, d, J=4.7 Hz).
Mass spectrum (ESI): 358.3 (M+H).

Example 4

Trans-5'-chloro-3'-oxo-N-methyl-N-(2-piperidin-1-ylethyl)-spiro[cyclohexane-1,1'-(3'H)-4'-azaisobenzofuran]-4-carboxamide

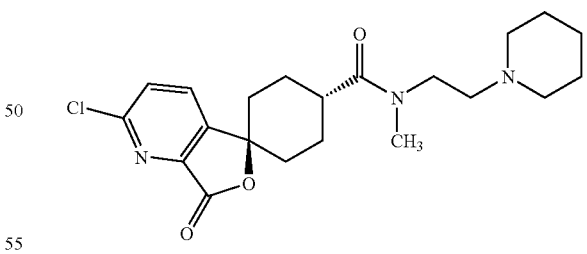

The entitled compound was obtained according to the method of Example 1 but starting from the compound obtained in Reference Example 1 (2) and N-methyl-N-(piperidinoethyl)amine.

$^1$HNMR (400 MHz, CDCl$_3$, δ): 1.34-1.46 (2H, m), 1.48-1.59 (4H, m), 1.79-2.11 (6H, m), 2.20-2.31 (2H, m), 2.34-2.53 (6H, m), 2.87-2.98 (1H, m), 2.94 (3H×1/2, s), 3.09 (3H×1/2, s), 3.42 (2H×1/2, t, J=6.9 Hz), 3.51 (2H×1/2, t, J=6.9 Hz), 7.52 (1H×1/2, d, J=8.2 Hz), 7.53 (1H×1/2, d, J=8.2 Hz), 8.02 (1H×1/2, d, J=8.2 Hz), 8.07 (1H×1/2, d, J=8.2 Hz).
Mass spectrum (ESI): 406.3 (M+H).

Example 5

Trans-3'-oxo-N-methyl-N-(2-piperidin-1-ylethyl)-spiro[cyclohexane-1,1'-(3'H)-5'-azaisobenzofuran]-4-carboxamide

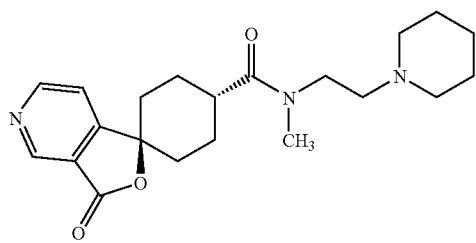

The entitled compound was obtained according to the method of Example 1 but starting from trans-3'-oxo-spiro[cyclohexane-1,1'-(3'H)-5'-azaisobenzofuran]-4-carboxylic acid and N-methyl-N-(piperidinoethyl)amine.

$^1$HNMR (400 MHz, CDCl$_3$, δ): 1.35-1.46 (2H, m), 1.47-1.64 (4H, m), 1.76-1.89 (2H, m), 1.93-2.08 (4H, m), 2.20-2.33 (2H, m), 2.35-2.50 (6H, m), 2.87-2.98 (1H, m), 2.95 (3H×1/2, s), 3.08 (3H×1/2, s), 3.42 (2H×1/2, t, J=7.0 Hz), 3.50 (2H×1/2, t, J=7.0 Hz), 7.62 (1H×1/2, d, J=5.1 Hz), 7.66 (1H×1/2, d, J=5.1 Hz), 8.77-8.83 (1H, m), 9.11 (1H, s).

Mass spectrum (ESI): 372.2 (M+H).

Example 6

Trans-3'-oxo-N-methyl-N-(2-pyrrolidin-1-ylethyl)-spiro[cyclohexane-1,1'-(3'H)-5'-azaisobenzofuran]-4-carboxamide

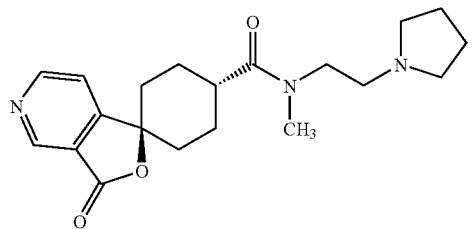

The entitled compound was obtained according to the method of Example 1 but starting from trans-3'-oxo-spiro[cyclohexane-1,1'-(3'H)-5'-azaisobenzofuran]-4-carboxylic acid and N-methyl-N-(pyrrolidinoethyl)amine.

$^1$HNMR (400 MHz, CDCl$_3$, δ): 1.69-1.91 (8H, m), 1.94-2.10 (4H, m), 2.22-2.34 (2H, m), 2.48-2.70 (6H, m), 2.87-2.99 (1H, m), 2.96 (3H, s), 3.10 (3H, s), 3.46 (2H, t, J=7.4 Hz), 3.55 (2H, t, J=7.2 Hz), 7.61 (1H×1/2, d, J=5.1 Hz), 7.66 (1H×1/2, d, J=5.1 Hz), 8.80 (1H, d, J=5.1 Hz), 9.12 (1H, s).

Mass spectrum (ESI): 358.3 (M+H).

Example 7

Trans-3'-oxo-N-methyl-N-(2-piperidin-1-ylethyl)-spiro[cyclohexane-1,1'-(3'H)-6'-azaisobenzofuran]-4-carboxamide

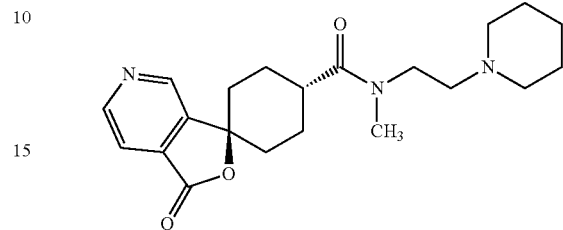

The entitled compound was obtained according to the method of Example 1 but starting from trans-3'-oxo-spiro[cyclohexane-1,1'-(3'H)-6'-azaisobenzofuran]-4-carboxylic acid and N-methyl-N-(piperidinoethyl)amine.

$^1$HNMR (400 MHz, CDCl$_3$, δ): 1.38-1.49 (2H, m), 1.52-1.62 (4H, m), 1.78-1.93 (2H, m), 2.0-2.13 (4H, m), 2.33-2.52 (8H, m), 2.90-3.02 (1H, m), 2.98 (3H×1/2, s), 3.11 (3H×1/2, s), 3.45 (2H×1/2, d, J=7.0 Hz), 3.54 (2H×1/2, d, J=7.0 Hz), 7.74 (1H, d, J=5.1 Hz), 8.84 (1H, d, J=4.8 Hz), 9.05-9.14 (1H, m).

Mass spectrum (ESI): 372.4 (M+H).

Example 8

Trans-3'-oxo-N-methyl-N-(2-piperidin-1-ylethyl)-spiro[cyclohexane-1,1'-(3'H)-7'-azaisobenzofuran]-4-carboxamide

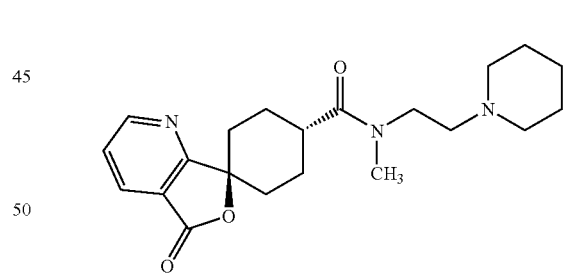

The entitled compound was obtained according to the method of Example 1 but starting from trans-3'-oxo-spiro[cyclohexane-1,1'-(3'H)-7'-azaisobenzofuran]-4-carboxylic acid and N-methyl-N-(piperidinoethyl)amine.

$^1$HNMR (400 MHz, CDCl$_3$, δ): 1.34-1.47 (2H, m), 1.47-1.61 (4H, m), 1.81-2.00 (6H, m), 2.22-2.51 (8H, m), 2.76-2.89 (1H, m), 2.94 (3H×1/2, s), 3.08 (3H×1/2, s), 3.42 (2H×1/2, t, J=7.1 Hz), 3.51 (2H×1/2, t, J=7.1 Hz), 7.41 (1H, dd, J=7.8 Hz, 4.9 Hz), 8.12 (1H×1/2, d, J=7.8 Hz, 1.6 Hz), 8.79-8.86 (1H, m).

Mass spectrum (ESI): 372.2 (M+H).

Example 9

Trans-5'-fluoro-3'-oxo-N-methyl-N-(2-pyrrolidin-1-ylethyl)-spiro[cyclohexane-1,1'-(3'H)-6'-azaisobenzofuran]-4-carboxamide

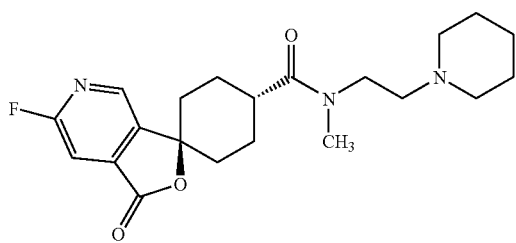

The entitled compound was obtained according to the method of Example 1 but starting from 6'-fluoro-1'-oxo-1'H-spiro[cyclohexane-1,3'-furo[3,4-c]pyridine]-4-carboxylic acid and N-methyl-N-(piperidinoethyl)amine.

$^1$HNMR (400 MHz, CDCl$_3$, δ): 1.38-1.50 (2H, m), 1.52-1.64 (4H, m), 1.83-1.94 (2H, m), 1.98-2.13 (4H, m), 2.32-2.53 (6H, m), 2.91-3.00 (1H, m), 2.98 (3H×1/2, s), 3.12 (3H×1/2, s), 3.45 (2H×1/2, t, J=7.1 Hz), 3.55 (2H×1/2, t, J=7.1 Hz), 7.35-7.36 (1H, m), 8.64 (1H×1/2, s), 8.68 (1H×1/2, s).

Mass spectrum (ESI): 390.2 (M+H).

Example 10

Trans-5'-ethoxy-3'-oxo-N-methyl-N-(2-pyrrolidin-1-ylethyl)-spiro[cyclohexane-1,1'-(3'H)-4'-azaisobenzofuran]-4-carboxamide

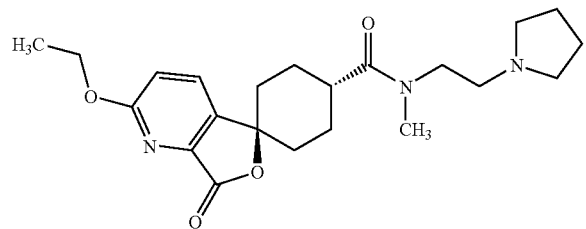

Sodium hydride (10 mg) was added to ethanol (1.0 mL). The solution was added to ethanol (1.0 mL) solution of the compound (40 mg) obtained in Example 1, and stirred at 65° C. for 18 hours. It was made to have a pH of 2 with 6 N hydrochloric acid at 0° C. This was neutralized with aqueous saturated sodium bicarbonate solution, and then extracted with ethyl acetate. The organic layer was washed with saturated saline water, dried with sodium sulfate, filtered and concentrated under reduced pressure. The resulting residue was purified through silica gel column chromatography (Biotage Column NH, ethyl acetate/hexane=10% to 90%, gradient) to obtain the entitled compound (34 mg, 83%) as a colorless oily substance.

$^1$HNMR (400 MHz, CDCl$_3$, δ): 1.41 (3H, t, J=7.1 Hz), 1.74-1.94 (6H, m), 1.94-2.13 (4H, m), 2.15-2.27 (2H, m), 2.51-2.73 (6H, m), 2.85-2.97 (1H, m), 2.99 (3H×1/2, s), 3.13 (3H×1/2, s), 3.49 (2H×1/2, t, J=7.4 Hz), 3.57 (2H×1/2, t, J=7.4 Hz), 4.51 (2H, q, J=7.1 Hz), 6.96 (1H×1/2, d, J=8.5 Hz), 6.96 (1H×1/2, d, J=8.5 Hz), 7.93 (1H×1/2, d, J=8.5 Hz), 7.98 (1H×1/2, d, J=8.5 Hz).

Mass spectrum (ESI): 402.3 (M+H).

Example 11

Trans-5'-methoxy-3'-oxo-N-methyl-N-(2-piperidin-1-ylethyl)-spiro[cyclohexane-1,1'-(3'H)-4'-azaisobenzofuran]-4-carboxamide

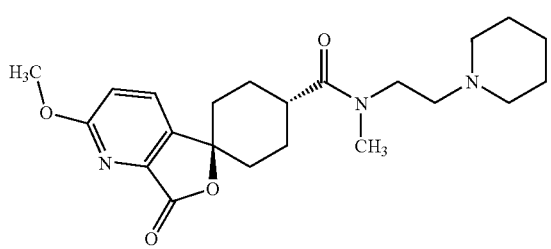

The entitled compound was obtained according to the method of Example 10 but starting from the compound obtained in Example 4 and methanol.

$^1$HNMR (400 MHz, CDCl$_3$, δ): 1.34-1.45 (2H, m), 1.48-1.60 (4H, m), 1.77-2.08 (6H, m), 2.13-2.25 (2H, m), 2.35-2.49 (6H, m), 2.83-2.95 (1H, m), 2.94 (3H×1/2, s), 3.08 (3H×1/2, s), 3.42 (2H×1/2, t, J=7.0 Hz), 3.50 (2H×1/2, t, J=7.0 Hz), 4.02 (3H, s), 6.95 (1H×1/2, d, J=8.6 Hz), 6.95 (1H×1/2, d, J=8.6 Hz), 7.91 (1H×1/2, d, J=8.6 Hz), 7.96 (1H×1/2, d, J=8.6 Hz).

Mass spectrum (ESI): 402.3 (M+H).

Example 12

Trans-5'-ethoxy-3'-oxo-N-methyl-N-(2-piperidin-1-ylethyl)-spiro[cyclohexane-1,1'-(3'H)-4'-azaisobenzofuran]-4-carboxamide

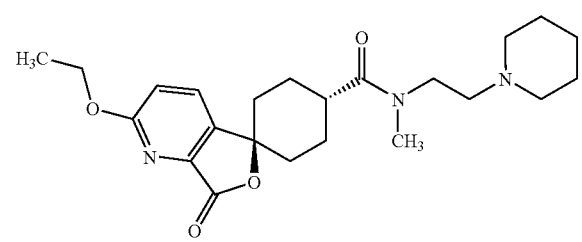

The entitled compound was obtained according to the method of Example 10 but starting from the compound obtained in Example 4 and ethanol.

$^1$HNMR (400 MHz, CDCl$_3$, δ): 1.37-1.49 (2H, m), 1.41 (3H, t, J=7.1 Hz), 1.52-1.62 (4H, m), 1.80-2.11 (6H, m), 2.15-2.26 (2H, m), 2.37-2.53 (6H, m), 2.86-2.97 (1H, m), 2.98 (3H×1/2, s), 3.12 (3H×1/2, s), 3.45 (2H×1/2, t, J=7.1 Hz), 3.54 (2H×1/2, t, J=7.1 Hz), 4.51 (2H, q, J=7.1 Hz), 6.96 (1H×1/2, d, J=8.5 Hz), 6.96 (1H×1/2, d, J=8.5 Hz), 7.93 (1H×1/2, d, J=8.5 Hz), 7.99 (1H×1/2, d, J=8.5 Hz).

Mass spectrum (ESI): 416.3 (M+H).

Example 13

Trans-5'-methoxy-3'-oxo-N-methyl-N-(2-pyrrolidin-1-ylethyl)-spiro[cyclohexane-1,1'-(3'H)-4'-azaisobenzofuran]-4-carboxamide

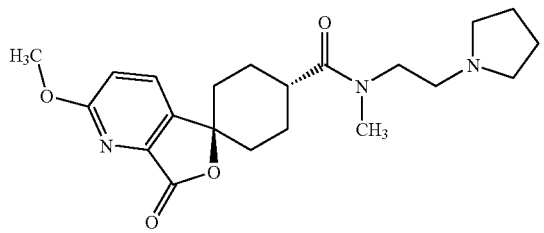

The entitled compound was obtained according to the method of Example 10 but starting from the compound obtained in Example 1 and methanol.

¹HNMR (400 MHz, CDCl₃, δ): 1.72-1.93 (6H, m), 1.93-2.12 (4H, m), 2.15-2.30 (2H, m), 2.48-2.75 (6H, m), 2.86-2.98 (1H, m), 2.99 (3H×1/2, s), 3.12 (3H×1/2, s), 3.49 (2H×1/2, t, J=7.4 Hz), 3.56 (2H×1/2, t, J=7.4 Hz), 4.06 (3H, s), 6.98 (1H×1/2, d, J=8.5 Hz), 6.99 (1H×1/2, d, J=8.5 Hz), 7.94 (1H×1/2, d, J=8.5 Hz), 7.99 (1H×1/2, d, J=8.5 Hz).

Mass spectrum (ESI): 388.3 (M+H).

Example 14

Trans-5'-propoxy-3'-oxo-N-methyl-N-(2-pyrrolidin-1-ylethyl)-spiro[cyclohexane-1,1'-(3'H)-4'-azaisobenzofuran]-4-carboxamide

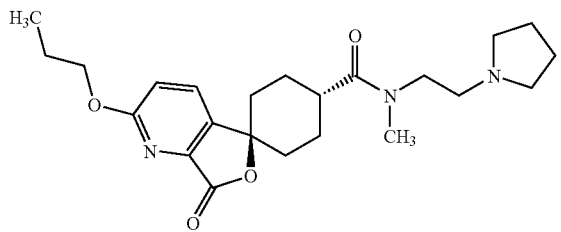

The entitled compound was obtained according to the method of Example 10 but starting from the compound obtained in Example 1 and propanol.

¹HNMR (400 MHz, CDCl₃, δ): 1.02 (3H, t, J=7.3 Hz), 1.72-1.93 (8H, m), 1.94-2.13 (4H, m), 2.14-2.32 (2H, m), 2.51-2.74 (6H, m), 2.86-2.97 (1H, m), 2.99 (3H×1/2, s), 3.12 (3H×1/2, s), 3.49 (2H×1/2, t, J=7.4 Hz), 3.56 (2H×1/2, t, J=7.4 Hz), 4.40 (2H, t, J=6.7 Hz), 6.97 (1H×1/2, d, J=8.5 Hz), 6.97 (1H×1/2, d, J=8.5 Hz), 7.93 (1H×1/2, d, J=8.5 Hz), 7.98 (1H×1/2, d, J=8.5 Hz).

Mass spectrum (ESI): 416.4 (M+H).

Example 15

Trans-5'-(morpholin-4-yl)-3'-oxo-N-methyl-N-(2-pyrrolidin-1-ylethyl)-spiro[cyclohexane-1,1'-(3'H)-4'-azaisobenzofuran]-4-carboxamide

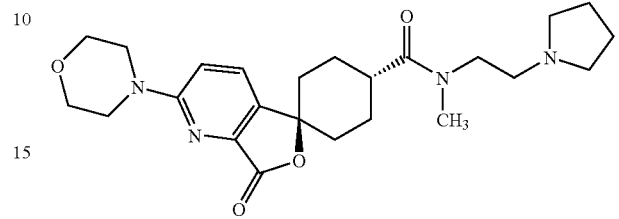

Morpholine (1.0 mL) was added to the compound (30 mg) obtained in Example 1, and stirred at 65° C. for 17 hours. The reaction liquid was concentrated under reduced pressure, and then purified through reversed-phase HPLC (0.1% TFA acetonitrile/H₂O=5% to 75%, gradient) to obtain the entitled compound (31 mg, 92%) as a colorless oily substance.

¹HNMR (400 MHz, CDCl₃, δ): 1.75-2.08 (10H, m), 2.09-2.20 (2H, m), 2.51-2.75 (6H, m), 2.84-2.95 (1H, m), 2.99 (3H×1/2, s), 3.13 (3H×1/2, s), 3.50 (2H×1/2, t, J=7.4 Hz), 3.58 (2H×1/2, t, J=7.4 Hz), 3.65 (4H, t, J=4.9 Hz), 3.82 (4H, t, J=4.9 Hz), 6.84 (1H×1/2, d, J=9.0 Hz), 6.85 (1H×1/2, d, J=9.0 Hz), 7.87 (1H×1/2, d, J=9.0 Hz), 7.92 (1H×1/2, d, J=9.0 Hz).

Mass spectrum (ESI): 443.3 (M+H).

Example 16

Trans-5'-(dimethylamino)-3'-oxo-N-methyl-N-(2-pyrrolidin-1-ylethyl)-spiro[cyclohexane-1,1'-(3'H)-4'-azaisobenzofuran]-4-carboxamide

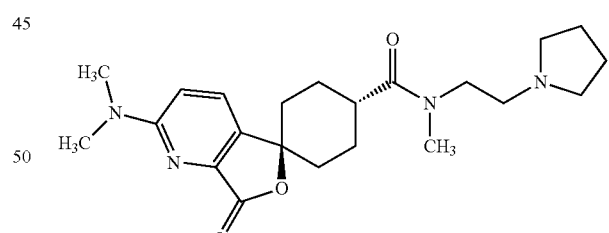

The entitled compound was obtained according to the method of Example 15 but starting from the compound obtained in Example 1 and dimethylamine.

¹HNMR (400 MHz, CDCl₃, δ): 1.76-1.94 (6H, m), 1.95-2.19 (6H, m), 2.52-2.77 (6H, m), 2.82-2.93 (1H, m), 2.99 (3H×1/2, s), 3.13 (3H×1/2, s), 3.18 (6H, s), 3.49 (2H×1/2, t, J=7.4 Hz), 3.59 (2H×1/2, t, J=7.4 Hz), 6.72 (1H×1/2, d, J=8.8 Hz), 6.72 (1H×1/2, d, J=8.8 Hz), 7.80 (1H×1/2, d, J=8.8 Hz), 7.86 (1H×1/2, d, J=8.8 Hz).

Mass spectrum (ESI): 401.4 (M+H).

Example 17

Trans-5'-(piperidin-1-yl)-3'-oxo-N-methyl-N-(2-pyrrolidin-1-ylethyl)-spiro[cyclohexane-1,1'-(3'H)-4'-azaisobenzofuran]-4-carboxamide

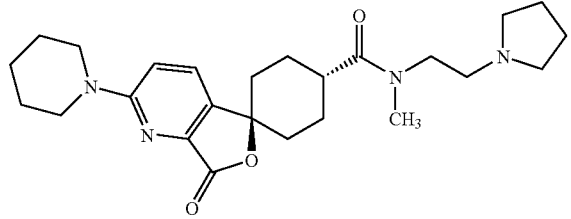

The entitled compound was obtained according to the method of Example 15 but starting from the compound obtained in Example 1 and piperidine.

$^1$HNMR (400 MHz, CDCl$_3$, δ): 1.52-2.20 (8H, m), 2.52-2.77 (6H, m), 2.80-2.93 (1H, m), 2.99 (3H×1/2, s), 3.13 (3H×1/2, s), 3.49 (2H×1/2, t, J=7.4 Hz), 3.59 (2H×1/2, t, J=7.4 Hz), 3.62-3.73 (4H, m), 6.84 (1H×1/2, d, J=9.0 Hz), 6.84 (1H×1/2, d, J=9.0 Hz), 7.79 (1H×1/2, d, J=9.0 Hz), 7.84 (1H×1/2, d, J=9.0 Hz).

Mass spectrum (ESI): 441.4 (M+H).

Example 18

Trans-5'-(piperidin-1-yl)-3'-oxo-N-methyl-N-(2-piperidin-1-ylethyl)-spiro[cyclohexane-1,1'-(3'H)-4'-azaisobenzofuran]-4-carboxamide

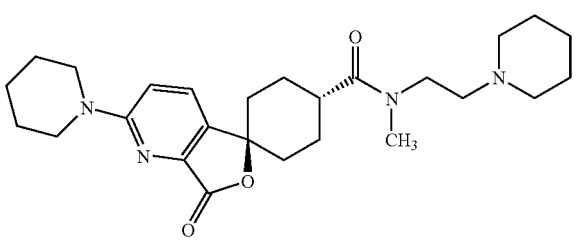

The entitled compound was obtained according to the method of Example 15 but starting from the compound obtained in Example 4 and piperidine.

$^1$HNMR (400 MHz, CDCl$_3$, δ): 1.38-1.80 (12H, m), 1.81-2.20 (8H, m), 2.36-2.59 (6H, m), 2.81-2.94 (1H, m), 2.98 (3H×1/2, s), 3.12 (3H×1/2, s), 3.46 (2H×1/2, t, J=7.1 Hz), 3.56 (2H×1/2, t, J=7.1 Hz), 3.60-3.71 (4H, m), 6.84 (1H×1/2, d, J=8.8 Hz), 6.85 (1H×1/2, d, J=8.8 Hz), 7.79 (1H×1/2, d, J=8.8 Hz), 7.84 (1H×1/2, d, J=8.8 Hz).

Mass spectrum (ESI): 455.3 (M+H).

Example 19

Trans-5'-phenoxy-3'-oxo-N-methyl-N-(2-piperidin-1-ylethyl)-spiro[cyclohexane-1,1'-(3'H)-4'-azaisobenzofuran]-4-carboxamide

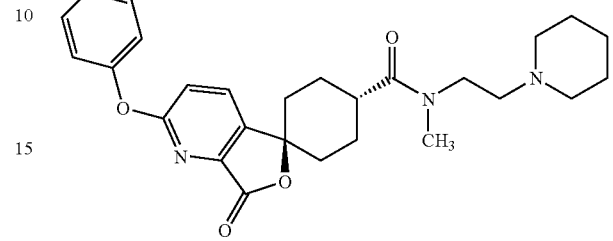

Phenol (40 mg) and cesium carbonate (209 mg) were added to DMF (2.0 mL) solution of the compound (100 mg) obtained in Example 4, and stirred at 65° C. for 23 hours. The reaction liquid was purified through reversed-phase HPLC (0.1% TFA acetonitrile/H$_2$O=5% to 75%, gradient) to obtain the entitled compound (57 mg, 57%) as a colorless oily substance.

$^1$HNMR (400 MHz, CDCl$_3$, δ): 1.39-1.50 (2H, m), 1.53-1.67 (4H, m), 1.79-2.13 (6H, m), 2.18-2.31 (2H, m), 2.37-2.62 (6H, m), 2.88-3.01 (1H, m), 2.98 (3H×1/2, s), 3.12 (3H×1/2, s), 3.46 (2H×1/2, t, J=7.0 Hz), 3.57 (2H×1/2, t, J=7.0 Hz), 7.12-7.28 (4H, m), 7.36-7.46 (2H, m), 8.06 (1H×1/2, d, J=8.5 Hz), 8.11 (1H×1/2, d, J=8.5 Hz).

Mass spectrum (ESI): 464.3 (M+H).

Example 20

Trans-5'-(pyridin-3-yloxy)-3'-oxo-N-methyl-N-(2-piperidin-1-ylethyl)-spiro[cyclohexane-1,1'-(3'H)-4'-azaisobenzofuran]-4-carboxamide

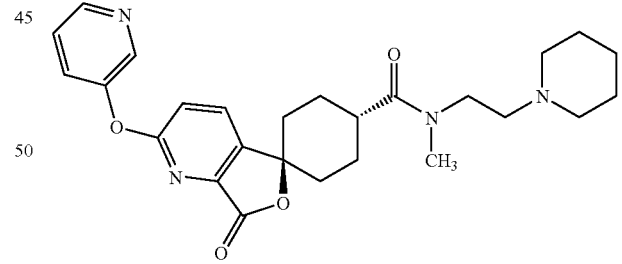

The entitled compound was obtained according to the method of Example 19 but starting from the compound obtained in Example 4 and 3-hydroxypyridine.

$^1$HNMR (400 MHz, CDCl$_3$, δ): 1.39-1.51 (2H, m), 1.52-1.65 (4H, m), 1.81-2.13 (6H, m), 2.20-2.33 (2H, m), 2.38-2.60 (6H, m), 2.88-3.01 (1H, m), 2.99 (3H×1/2, s), 3.13 (3H×1/2, s), 3.46 (2H×1/2, t, J=7.0 Hz), 3.57 (2H×1/2, t, J=7.0 Hz), 7.22-7.41 (2H, m), 7.61-7.69 (1H, m), 8.12 (1H×1/2, d, J=8.5 Hz), 8.18 (1H×1/2, d, J=8.5 Hz), 8.45-8.56 (2H, m).

Mass spectrum (ESI): 465.2 (M+H).

Example 21

Trans-5'-phenyl-3'-oxo-N-methyl-N-(2-pyrrolidin-1-ylethyl)-spiro[cyclohexane-1,1'-(3'H)-4'-azaisobenzofuran]-4-carboxamide

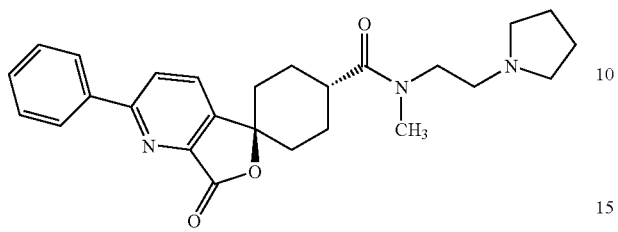

Phenylboronic acid (14 mg), palladium tetrakistriphenylphosphine (15 mg) and aqueous 2 M sodium carbonate solution (0.15 mL) were added to 1,2-dimethoxyethane (1.0 mL) solution of the compound (30 mg) obtained in Example 1, and stirred at 80° C. for 5 hours. Water was added to it, and extracted with ethyl acetate. The organic layer was washed with saturated saline water, dried with sodium sulfate, then filtered and concentrated under reduced pressure. The resulting residue was purified through silica gel column chromatography (Biotage Column NH, ethyl acetate/hexane=5% to 95%, gradient) to obtain the entitled compound (26 mg, 78%) as a colorless oily substance.

$^1$HNMR (400 MHz, CDCl$_3$, δ): 1.76-1.88 (4H, m), 1.89-2.17 (6H, m), 2.22-2.37 (2H, m), 2.52-2.77 (6H, m), 2.90-3.01 (1H, m), 3.01 (3H×1/2, s), 3.15 (3H×1/2, s), 3.51 (2H×1/2, t, J=7.3 Hz), 3.59 (2H×1/2, t, J=7.3 Hz), 7.43-7.56 (3H, m), 7.96 (1H×1/2, d, J=8.3 Hz), 7.97 (1H×1/2, d, J=8.3 Hz), 8.08-8.14 (2H, m), 8.16 (1H×1/2, d, J=8.3 Hz), 8.20 (1H×1/2, d, J=8.3 Hz).

Mass spectrum (ESI): 434.2 (M+H).

Example 22

Trans-5'-phenyl-3'-oxo-N-methyl-N-(2-piperidin-1-ylethyl)-spiro[cyclohexane-1,1'-(3'H)-4'-azaisobenzofuran]-4-carboxamide

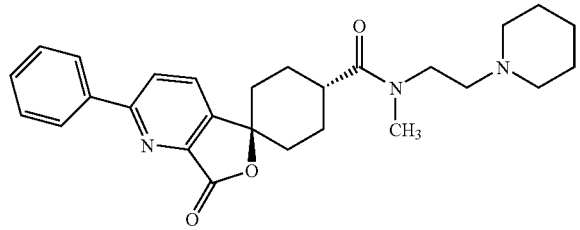

The entitled compound was obtained according to the method of Example 21 but starting from the compound obtained in Example 4 and phenylboronic acid.

$^1$HNMR (400 MHz, CDCl$_3$, δ): 1.35-1.48 (2H, m), 1.49-1.61 (4H, m), 1.84-2.13 (6H, m), 2.21-2.32 (2H, m), 2.35-2.53 (6H, m), 2.87-2.99 (1H, m), 2.96 (3H×1/2, s), 3.10 (3H×1/2, s), 3.44H×1/2, t, J=7.0 Hz), 3.53 (2H×1/2, t, J=7.0 Hz), 7.40-7.53 (3H, m), 7.93 (1H×1/2, d, J=8.2 Hz), 7.94 (1H×1/2, d, J=8.2 Hz), 8.05-8.10 (2H, m), 8.12 (1H×1/2, d, J=8.2 Hz), 8.17 (1H×1/2, d, J=8.2 Hz).

Mass spectrum (ESI): 448.3 (M+H).

Example 23

Trans-5'-(4-fluorophenyl)-3'-oxo-N-methyl-N-(2-piperidin-1-ylethyl)-spiro[cyclohexane-1,1'-(3'H)-4'-azaisobenzofuran]-4-carboxamide

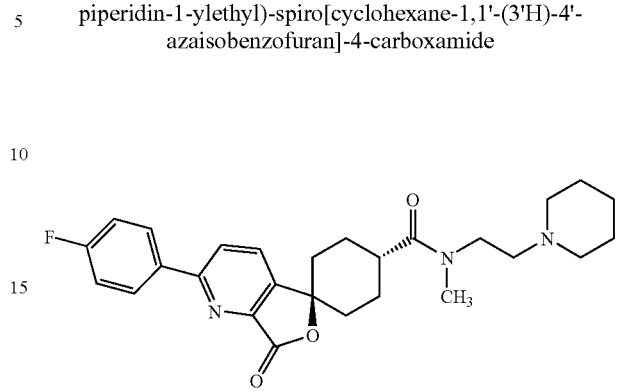

The entitled compound was obtained according to the method of Example 21 but starting from the compound obtained in Example 4 and 4-fluorophenylboronic acid.

$^1$HNMR (400 MHz, CDCl$_3$, δ): 1.35-1.47 (2H, m), 1.48-1.61 (4H, m), 1.83-2.12 (6H, m), 2.21-2.32 (2H, m), 2.34-2.51 (6H, m), 2.88-2.99 (1H, m), 2.96 (3H×1/2, s), 3.10 (3H×1/2, s), 3.44 (2H×1/2, t, J=7.0 Hz), 3.52 (2H×1/2, t, J=7.0 Hz), 7.09-7.19 (2H, m), 7.88 (1H×1/2, d, J=8.2 Hz), 7.89 (1H×1/2, d, J=8.2 Hz), 8.04-8.20 (3H, m).

Mass spectrum (ESI): 466.3 (M+H).

Example 24

Trans-5'-(pyrimidin-5-yl)-3'-oxo-N-methyl-N-(2-piperidin-1-ylethyl)-spiro[cyclohexane-1,1'-(3'H)-4'-azaisobenzofuran]-4-carboxamide

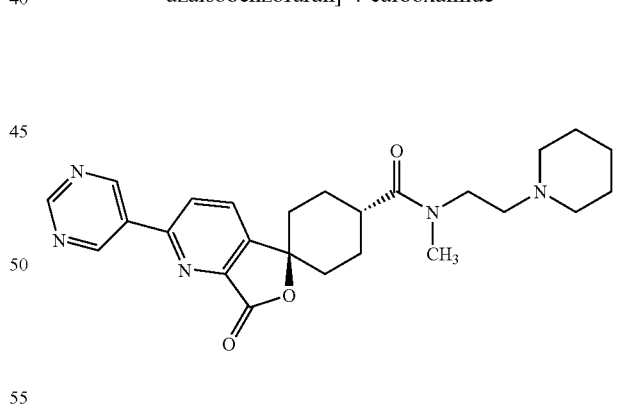

The entitled compound was obtained according to the method of Example 21 but starting from the compound obtained in Example 4 and pyrimidine-5-boronic acid.

$^1$HNMR (400 MHz, CDCl$_3$, δ): 1.39-1.51 (2H, m), 1.52-1.65 (4H, m), 1.87-2.20 (6H, m), 2.29-2.58 (8H, m), 2.94-3.07 (1H, m), 3.00 (3H×1/2, s), 3.14 (3H×1/2, s), 3.47 (2H×1/2, t, J=7.0 Hz), 3.56 (2H×1/2, t, J=7.0 Hz), 7.99 (1H×1/2, d, J=8.0 Hz), 8.00 (1H×1/2, d, J=8.0 Hz), 8.26 (1H×1/2, d, J=8.0 Hz), 8.31 (1H×1/2, d, J=8.0 Hz), 9.32 (1H, s), 9.43 (2H, s).

Mass spectrum (ESI): 450.3 (M+H).

Example 25

Trans-5'-(6-methoxypyridin-3-yl)-3'-oxo-N-methyl-N-(2-piperidin-1-ylethyl)-spiro[cyclohexane-1,1'-(3'H)-4'-azaisobenzofuran]-4-carboxamide

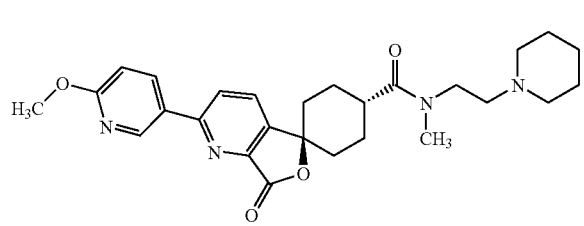

The entitled compound was obtained according to the method of Example 21 but starting from the compound obtained in Example 4 and 2-methoxy-5-pyridine-boronic acid.

$^1$HNMR (400 MHz, CDCl$_3$, δ): 1.37-1.72 (6H, m), 1.85-2.16 (6H, m), 2.22-2.37 (2H, m), 2.37-2.56 (6H, m), 2.90-3.03 (1H, m), 2.99 (3H×1/2, s), 3.13 (3H×1/2, s), 3.47 (2H×1/2, t, J=7.1 Hz), 3.55 (2H×1/2, t, J=7.1 Hz), 4.01 (3H, s), 6.87 (1H, d, J=8.8 Hz), 7.90 (1H×1/2, d, J=8.3 Hz), 7.91 (1H×1/2, d, J=8.3 Hz), 8.15 (1H×1/2, d, J=8.3 Hz), 8.20 (1H×1/2, d, J=8.3 Hz), 8.43 (1H, dd, J=8.8, 2.4 Hz), 8.77-8.85 (1H, m).

Mass spectrum (ESI): 479.2 (M+H).

Example 26

Trans-5'-[4-(methylsulfonyl)phenyl]-3'-oxo-N-methyl-N-(2-piperidin-1-ylethyl)-spiro[cyclohexane-1,1'-(3'H)-4'-azaisobenzofuran]-4-carboxamide

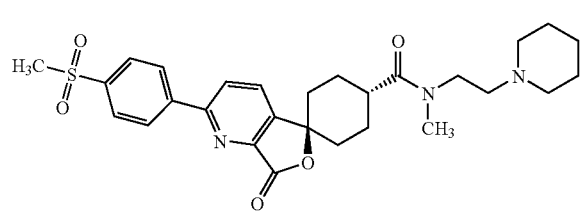

The entitled compound was obtained according to the method of Example 21 but starting from the compound obtained in Example 4 and 4-(methanesulfonyl)phenylboronic acid.

$^1$HNMR (400 MHz, CDCl$_3$, δ): 1.39-1.80 (6H, m), 1.86-2.19 (6H, m), 2.27-2.57 (6H, m), 2.93-3.04 (1H, m), 3.00 (3H×1/2, s), 3.11 (3H, s), 3.14 (3H×1/2, s), 3.48 (2H×1/2, t, J=7.0 Hz), 3.56 (2H×1/2, t, J=7.0 Hz), 8.03 (1H×1/2, d, J=8.3 Hz), 8.04 (1H×1/2, d, J=8.3 Hz), 8.06-8.11 (2H, m), 8.24 (1H×1/2, d, J=8.3 Hz), 8.29 (1H×1/2, d, J=8.3 Hz), 8.31-8.35 (2H, m).

Mass spectrum (ESI): 526.2 (M+H).

Example 27

Trans-5'-(6-methoxypyridin-3-yl)-3'-oxo-N-methyl-N-(2-pyrrolidin-1-Ylethyl)-spiro[cyclohexane-1,1'-(3'H)-4'-azaisobenzofuran]-4-carboxamide

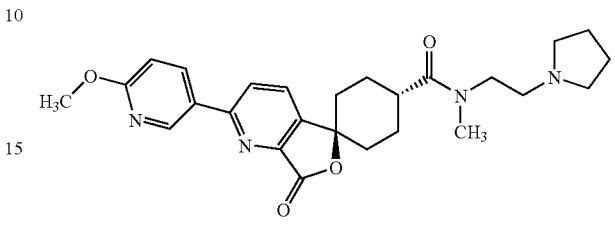

The entitled compound was obtained according to the method of Example 21 but starting from the compound obtained in Example 1 and 2-methoxy-5-pyridine-boronic acid.

$^1$HNMR (400 MHz, CDCl$_3$, δ): 1.57-1.86 (4H, m), 1.86-2.16 (6H, m), 2.21-2.38 (2H, m), 2.49-2.75 (6H, m), 2.90-3.04 (1H, m), 3.01 (3H×1/2, s), 3.14 (3H×1/2, s), 3.51 (2H×1/2, t, J=7.3 Hz), 3.57 (2H×1/2, t, J=7.3 Hz), 4.01 (3H, s), 6.87 (1H, d, J=8.8 Hz), 7.90 (1H×1/2, d, J=8.3 Hz), 7.91 (1H×1/2, d, J=8.3 Hz), 8.16 (1H×1/2, d, J=8.3 Hz), 8.20 (1H×1/2, d, J=8.3 Hz), 8.43 (1H, dd, J=8.8, 2.7 Hz), 8.81 (1H, d, J=2.7 Hz).

Mass spectrum (ESI): 465.2 (M+H).

Example 28

Trans-5'-(1-methyl-1H-pyrazol-4-yl)-3'-oxo-N-methyl-N-(2-piperidin-1-ylethyl)-spiro[cyclohexane-1,1'-(3'H)-4'-azaisobenzofuran]-4-carboxamide

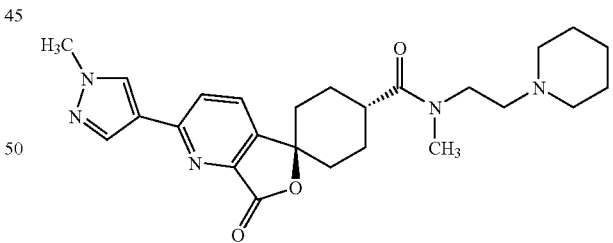

The entitled compound was obtained according to the method of Example 21 but starting from the compound obtained in Example 4 and 1-methyl-4-(4,4,5,5-tetramethyl-1,3,2-dioxabororan)-1H-pyrazole.

$^1$HNMR (400 MHz, CDCl$_3$, δ): 1.32-1.65 (6H, m), 1.79-2.11 (6H, m), 2.17-2.31 (2H, m), 2.33-2.51 (6H, m), 2.84-2.99 (1H, m), 2.95 (3H×1/2, s), 3.09 (3H×1/2, s), 3.38-3.57 (2H, m), 3.93 (3H, s), 7.58-7.66 (1H, m), 7.95-8.08 (2H, m), 8.11 (1H, s).

Mass spectrum (ESI): 452.2 (M+H).

Example 29

Trans-5'-(2,4-dimethoxypyrimidin-5-yl)-3'-oxo-N-methyl-N-(2-piperidin-1-ylethyl)-spiro[cyclohexane-1,1'-(3'H)-4'-azaisobenzofuran]-4-carboxamide

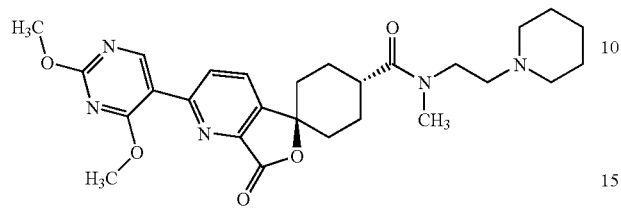

The entitled compound was obtained according to the method of Example 21 but starting from the compound obtained in Example 4 and 2,4-dimethoxypyridine-5-boronic acid.

$^1$HNMR (400 MHz, CDCl$_3$, δ): 1.32-1.75 (6H, m), 1.80-2.11 (6H, m), 2.18-2.32 (2H, m), 2.32-2.54 (6H, m), 2.85-3.00 (1H, m), 2.96 (3H×1/2, s), 3.10 (3H×1/2, s), 3.44 (2H×1/2, t, J=7.0 Hz), 3.52 (2H×1/2, t, J=7.0 Hz), 4.04 (3H, s), 4.08 (3H, s), 8.05-8.19 (2H, m), 9.04 (1H, s).

Mass spectrum (ESI): 510.2 (M+H).

Example 30

Trans-5'-ethyl-3'-oxo-N-methyl-N-(2-piperidin-1-ylethyl)-spiro[cyclohexane-1,1'-(3'H)-4'-azaisobenzofuran]-4-carboxamide

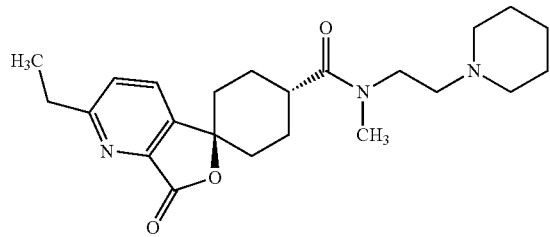

[1,1'-Bis(diphenylphosphino)ferrocene]dichloropalladium(II) (38 mg), potassium vinyltrifluoroborate (41 mg) and triethylamine (0.036 mL) were added in that order to n-propanol (2.0 mL) solution of the compound (120 mg) obtained in Example 4, and stirred at 80° C. for 3 hours. The reaction liquid was diluted with ethyl acetate, and then washed with water and saturated saline water in that order. The organic layer was dried with sodium sulfate, filtered, concentrated under reduced pressure, and purified through silica gel column chromatography (Biotage Column NH, ethyl acetate/hexane=5% to 100%, gradient). The resulting residue was dissolved in methanol (1.0 mL), 5% palladium-carbon (5 mg) was added to it, and stirred in a hydrogen atmosphere at room temperature for 1 hour. After the catalyst was removed through filtration, the residue was concentrated under reduced pressure to obtain the entitled compound (10 mg, 10%) as a pale yellow oily substance.

$^1$HNMR (400 MHz, CDCl$_3$, δ): 1.36 (3H, t, J=7.6 Hz), 1.40-1.69 (6H, m), 1.76-2.14 (6H, m), 2.16-2.33 (2H, m), 2.37-2.58 (6H, m), 2.87-3.04 (3H, m), 2.98 (3H×1/2, s), 3.12 (3H×1/2, s), 3.46 (2H×1/2, t, J=7.1 Hz), 3.55 (2H×1/2, t, J=7.1 Hz), 7.40 (1H×1/2, d, J=8.0 Hz), 7.40 (1H×1/2, d, J=8.0 Hz), 8.01 (1H×1/2, d, J=8.0 Hz), 8.06 (1H×1/2, d, J=8.0 Hz).

Mass spectrum (ESI): 400.3 (M+H).

Example 31

N-methyl-7'-oxo-N-(2-piperidin-1-ylethyl)-7'H-spiro[cyclohexane-1,5'-furo[3,4-b]pyridine]-4-carboxamide

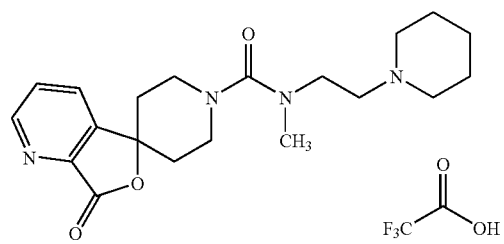

With cooling with ice, N,N-diisopropylethylamine (10.6 mL) and N-methyl-2-piperidin-1-ylethanamine (7.10 g) were added in that order to chloroform (140 mL) solution of triphosgene (8.15 g). The reaction liquid was stirred for 1 hour with cooling with ice, and then water (25 mL) was added thereto. The reaction liquid was azeotroped with toluene and then dried overnight under reduced pressure to obtain methyl (2-piperidin-1-ylethyl)carbamyl chloride monohydrochloride (20.0 g) as a pale yellow oily substance. Not further purified, the compound was used in the next reaction. Chloroform (2.0 mL), N,N-diisopropylethylamine (0.342 mL), 7H-spiro[furo[3,4-b]pyridine-5,4'-piperidin]-7-one dihydrochloride (136 mg) were added to the obtained methyl(2-piperidin-1-ylethyl)carbamyl chloride monohydrochloride (100 mg), and stirred at 70° C. for 11 hours. The reaction liquid was concentrated under reduced pressure, and then purified through reversed-phase HPLC (0.1% TFA acetonitrile/H$_2$O=5% to 50%, gradient) to obtain the entitled compound (57 mg, 24%) as a pale yellow oily substance.

$^1$HNMR (400 MHz, CDCl$_3$, δ): 1.67-1.81 (2H, m), 1.84-2.01 (4H, m), 2.14-2.29 (2H, m), 2.64-2.97 (4H, m), 2.98 (3H, s), 3.22-3.45 (4H, m), 3.52-3.64 (2H, m), 3.69-3.86 (4H, m), 7.60 (1H, dd, J=7.9, 4.8 Hz), 7.90 (1H, dd, J=7.9, 1.3 Hz), 8.92 (1H, dd, J=4.8, 1.3 Hz).

Mass spectrum (ESI): 373.2 (M+H).

Example 32

Trans-4'-chloro-3'-oxo-N-methyl-N-(2-piperidin-1-ylethyl)-spiro[cyclohexane-1,1'-(3'H)-5'-azaisobenzofuran]-4-carboxamide

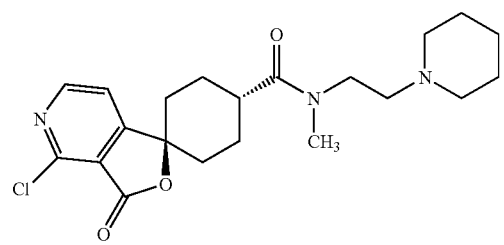

The entitled compound was obtained according to the method of Example 1 but starting from the compound obtained in Reference Example 3 and N-methyl-N-(piperidinoethyl)amine.

¹HNMR (400 MHz, CDCl₃, δ): 1.39-1.49 (2H, m), 1.52-1.65 (4H, m), 1.74-1.85 (2H, m), 1.95-2.14 (4H, m), 2.29-2.58 (8H, m), 2.92-3.04 (1H, m), 2.97 (3H×1/2, s), 3.12 (3H×1/2, s), 3.45 (2H×1/2, t, J=6.8 Hz), 3.50-3.61 (2H×1/2, m), 7.55 (1H×1/2, d, J=4.9 Hz), 7.60 (1H×1/2, d, J=4.9 Hz), 8.58-8.61 (1H, m).

Mass spectrum (ESI): 406.1, 408.1 (M+H).

Example 33

Trans-4'-chloro-3'-oxo-N-methyl-N-(2-pyrrolidin-1-yl-ethyl)-spiro[cyclohexane-1,1'-(3'H)-5'-azaisobenzofuran]-4-carboxamide

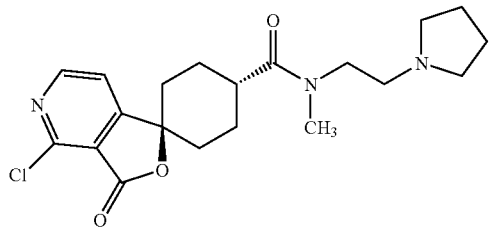

The entitled compound was obtained according to the method of Example 1 but starting from the compound obtained in Reference Example 3 and N-methyl-N-(pyrrolidinoethyl)amine.

¹HNMR (400 MHz, CDCl₃, δ): 1.74-1.86 (6H, m), 1.94-2.15 (4H, m), 2.30-2.44 (2H, m), 2.53-2.76 (6H, m), 2.94-3.03 (1H, m), 2.99 (3H×1/2, s), 3.13 (3H×1/2, s), 3.45-3.63 (2H, m), 7.53-7.63 (1H, m), 8.57-8.63 (1H, m).

Mass spectrum (ESI): 392.1, 394.1 (M+H.)

Example 34

Trans-4'-methoxy-3'-oxo-N-methyl-N-(2-piperidin-1-ylethyl)-spiro[cyclohexane-1,1'-(3'H)-5'-azaisobenzofuran]-4-carboxamide

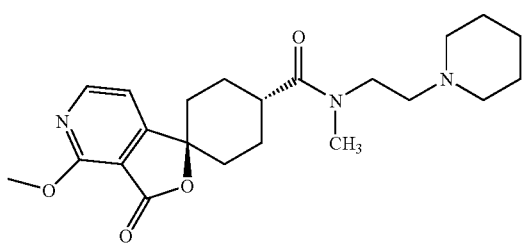

The entitled compound was obtained according to the method of Example 10 but starting from the compound obtained in Example 32 and methanol.

¹HNMR (400 MHz, CDCl₃, δ): 1.40-1.49 (2H, m), 1.53-1.63 (4H, m), 1.72-1.85 (2H, m), 1.94-2.11 (4H, m), 2.26-2.37 (2H, m), 2.38-2.55 (6H, m), 2.90-3.02 (1H, m), 2.97 (3H×1/2, s), 3.11 (3H×1/2, s), 3.45 (2H×1/2, t, J=6.8 Hz), 3.55 (2H×1/2, t, J=7.1 Hz), 4.13 (3H, s), 7.18 (1H×1/2, d, J=5.4 Hz), 7.22 (1H×1/2, d, J=5.4 Hz), 8.35-8.39 (1H, m).

Mass spectrum (ESI): 402.2 (M+H).

Example 35

Trans-4'-methoxy-3'-oxo-N-methyl-N-(2-pyrrolidin-1-ylethyl)-spiro[cyclohexane-1,1'-(3'H)-5'-azaisobenzofuran]-4-carboxamide

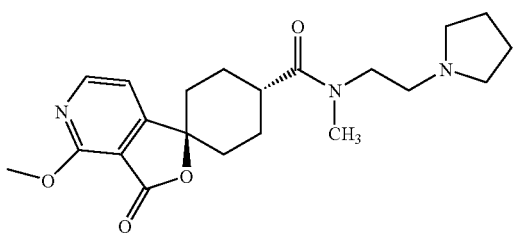

The entitled compound was obtained according to the method of Example 10 but starting from the compound obtained in Example 33 and methanol.

¹HNMR (400 MHz, CDCl₃, δ): 1.73-1.88 (6H, m), 1.94-2.12 (4H, m), 2.23-2.36 (2H, m), 2.54-2.79 (6H, m), 2.90-2.98 (1H, m), 2.99 (3H×1/2, s), 3.13 (3H×1/2, s), 3.49 (2H×1/2, t, J=7.6 Hz), 3.60 (2H×1/2, t, J=7.3 Hz), 4.13 (3H, s), 7.16-7.23 (1H, m), 8.36 (1H, d, J=5.4 Hz).

Mass spectrum (ESI): 388.2 (M+H).

Example 36

Trans-4'-ethoxy-3'-oxo-N-methyl-N-(2-piperidin-1-ylethyl)-spiro[cyclohexane-1,1'-(3'H)-5'-azaisobenzofuran]-4-carboxamide

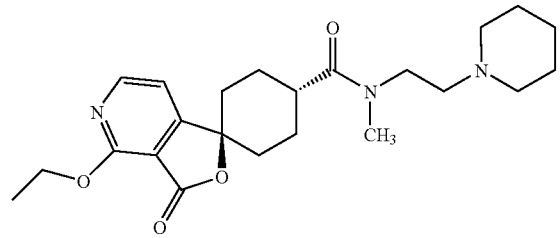

The entitled compound was obtained according to the method of Example 10 but starting from the compound obtained in Example 32 and ethanol.

¹HNMR (400 MHz, CDCl₃, δ): 1.40-1.51 (2H, m), 1.48 (3H, t, J=7.1 Hz), 1.53-1.65 (4H, m), 1.73-1.87 (2H, m), 1.94-2.11 (4H, m), 2.24-2.35 (2H, m), 2.39-2.57 (6H, m), 2.89-2.97 (1H, m), 2.97 (3H×1/2, s), 3.11 (3H×1/2, s), 3.45 (2H×1/2, t, J=7.1 Hz), 3.56 (2H×1/2, t, J=6.8 Hz), 4.61 (2H, q, J=7.2 Hz), 7.12-7.21 (1H, m), 8.31-8.36 (1H, m).

Mass spectrum (ESI): 416.2 (M+H).

Example 37

Trans-4'-ethoxy-3'-oxo-N-methyl-N-(2-pyrrolidin-1-ylethyl)-spiro[cyclohexane-1,1'-(3'H)-5'-azaisobenzofuran]-4-carboxamide

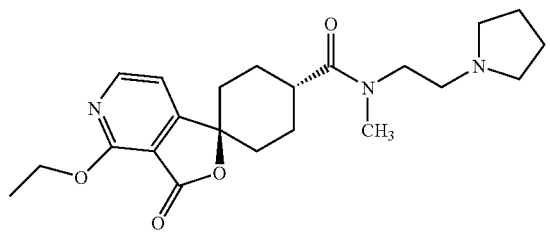

The entitled compound was obtained according to the method of Example 10 but starting from the compound obtained in Example 33 and ethanol.

¹HNMR (400 MHz, CDCl₃, δ): 1.48 (3H, t, J=7.2 Hz), 1.73-1.89 (6H, m), 1.93-2.13 (4H, m), 2.22-2.35 (2H, m), 2.52-2.77 (6H, m), 2.88-2.98 (1H, m), 2.99 (3H×1/2, s), 3.12 (3H×1/2, s), 3.48 (2H×1/2, t, J=7.3 Hz), 3.59 (2H×1/2, t, J=7.1 Hz), 4.61 (2H, q, J=7.2 Hz), 7.12-7.20 (1H, m), 8.30-8.38 (1H, m).

Mass spectrum (ESI): 402.2 (M+H).

Example 38

Trans-4'-isopropoxy-3'-oxo-N-methyl-N-(2-piperidin-1-ylethyl)-spiro[cyclohexane-1,1'-(3'H)-5'-azaisobenzofuran]-4-carboxamide

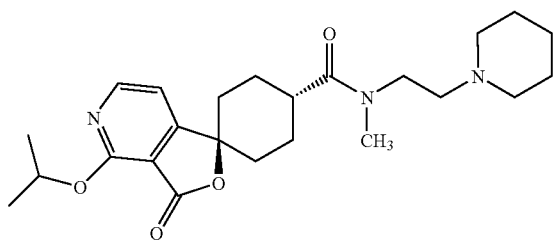

The entitled compound was obtained according to the method of Example 10 but starting from the compound obtained in Example 32 and 2-propanol.

¹HNMR (400 MHz, CDCl₃, δ): 1.40-1.49 (2H, m), 1.45 (6H, d, J=6.3 Hz), 1.54-1.64 (4H, m), 1.73-1.87 (2H, m), 1.94-2.12 (4H, m), 2.22-2.34 (2H, m), 2.38-2.57 (6H, m), 2.88-2.98 (1H, m), 2.97 (3H×1/2, s), 3.11 (3H×1/2, s), 3.44 (2H×1/2, t, J=7.1 Hz), 3.55 (2H×1/2, t, J=7.1 Hz), 5.47-5.58 (1H, m), 7.09-7.18 (1H, m), 8.30-8.36 (1H, m).

Mass spectrum (ESI): 430.3 (M+H).

Example 39

Trans-4'-isopropoxy-3'-oxo-N-methyl-N-(2-pyrrolidin-1-ylethyl)-spiro[cyclohexane-1,1'-(3'H)-5'-azaisobenzofuran]-4-carboxamide

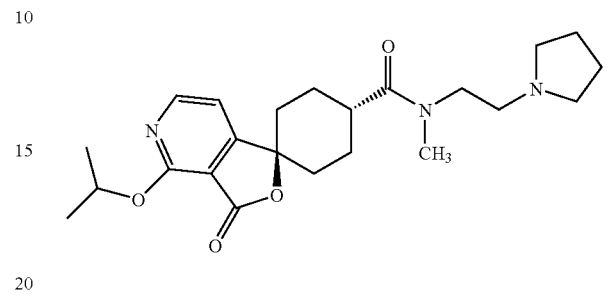

The entitled compound was obtained according to the method of Example 10 but starting from the compound obtained in Example 33 and 2-propanol.

¹HNMR (400 MHz, CDCl₃, δ): 1.45 (6H, d, J=6.3 Hz), 1.70-1.86 (6H, m), 1.94-2.10 (4H, m), 2.20-2.34 (2H, m), 2.52-2.72 (6H, m), 2.87-2.97 (1H, m), 2.99 (3H×1/2, s), 3.12 (3H×1/2, s), 3.48 (2H×1/2, t, J=7.3 Hz), 3.57 (2H×1/2, t, J=7.3 Hz), 5.47-5.58 (1H, m), 7.10-7.18 (1H, m), 8.30-8.34 (1H, m).

Mass spectrum (ESI): 416.2 (M+H).

Example 40

Trans-4'-cyclopropylmethoxy-3'-oxo-N-methyl-N-(2-pyrrolidin-1-ylethyl)-spiro[cyclohexane-1,1'-(3'H)-5'-azaisobenzofuran]-4-carboxamide

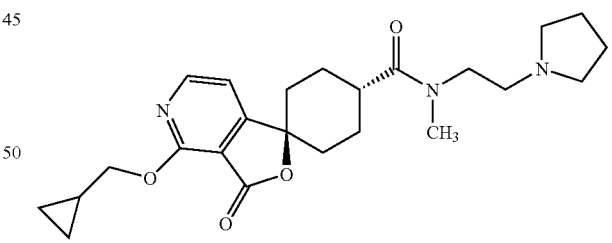

The entitled compound was obtained according to the method of Example 10 but starting from the compound obtained in Example 33 and cyclopropanemethanol.

¹HNMR (400 MHz, CDCl₃, δ): 0.37-0.45 (2H, m), 0.57-0.66 (2H, m), 1.36-1.47 (1H, m), 1.74-1.87 (6H, m), 1.94-2.12 (4H, m), 2.22-2.36 (2H, m), 2.53-2.71 (6H, m), 2.89-2.98 (1H, m), 2.99 (3H×1/2, s), 3.12 (3H×1/2, s), 3.49 (2H×1/2, t, J=7.6 Hz), 3.57 (2H×1/2, t, J=7.3 Hz), 4.37 (1H, s), 4.39 (1H, s), 7.12-7.20 (1H, m), 8.29-8.34 (1H, m).

Mass spectrum (ESI): 428.2 (M+H).

Example 41

Trans-4'-methyl-3'-oxo-N-methyl-N-(2-piperidin-1-ylethyl)-spiro[cyclohexane-1,1'-(3'H)-5'-azaisobenzofuran]-4-carboxamide

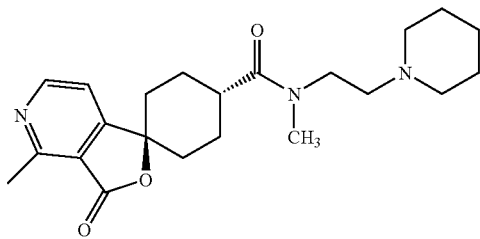

The entitled compound was obtained according to the method of Example 21 but starting from the compound obtained in Example 32 and trimethylboroxine.

$^1$HNMR (400 MHz, CDCl$_3$, δ): 1.40-1.49 (2H, m), 1.54-1.63 (4H, m), 1.76-1.90 (2H, m), 1.97-2.12 (4H, m), 2.25-2.36 (2H, m), 2.39-2.55 (6H, m), 2.90 (3H, s), 2.91-3.01 (1H, m), 2.98 (3H×1/2, s), 3.12 (3H×1/2, s), 3.45 (2H×1/2, t, J=6.8 Hz), 3.56 (2H×1/2, t, J=6.8 Hz), 7.44 (1H×1/2, d, J=5.4 Hz), 7.49 (1H×1/2, d, J=5.4 Hz), 8.64-8.69 (1H, m).

Mass spectrum (ESI): 386.2 (M+H).

Example 42

Trans-4'-ethyl-3'-oxo-N-methyl-N-(2-pyrrolidin-1-ylethyl)-spiro[cyclohexane-1,1'-(3'H)-5'-azaisobenzofuran]-4-carboxamide

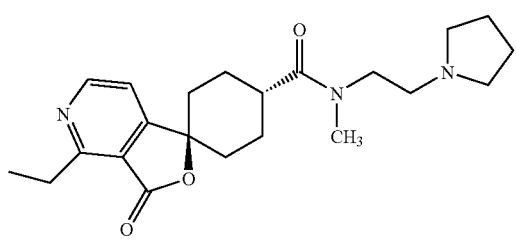

The entitled compound was obtained according to the method of Example 30 but starting from the compound obtained in Example 33.

$^1$HNMR (400 MHz, CDCl$_3$, δ): 1.31-1.39 (3H, m), 1.76-1.91 (6H, m), 1.97-2.12 (4H, m), 2.22-2.37 (2H, m), 2.53-2.83 (6H, m), 2.92-3.17 (4H, m), 3.25-3.34 (2H, m), 3.45-3.68 (2H, m), 7.42-7.51 (1H, m), 8.68-8.74 (1H, m).

Mass spectrum (ESI): 386.2 (M+H).

Example 43

Trans-4'-phenyl-3'-oxo-N-methyl-N-(2-piperidin-1-ylethyl)-spiro[cyclohexane-1,1'-(3'H)-5'-azaisobenzofuran]-4-carboxamide

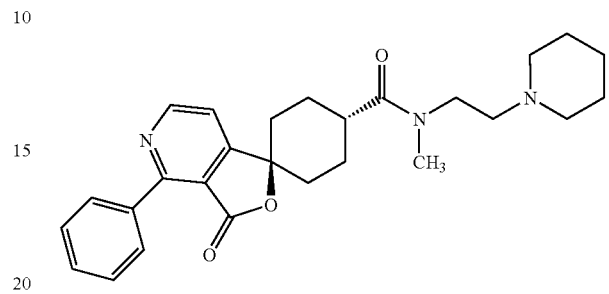

The entitled compound was obtained according to the method of Example 21 but starting from the compound obtained in Example 32 and phenylboronic acid.

$^1$HNMR (400 MHz, CDCl$_3$, δ): 1.40-1.49 (2H, m), 1.54-1.64 (4H, m), 1.79-1.90 (2H, m), 1.99-2.16 (4H, m), 2.35-2.57 (8H, m), 2.94-3.04 (1H, m), 2.99 (3H×1/2, s), 3.12 (3H×1/2, s), 3.46 (2H×1/2, t, J=7.1 Hz), 3.57 (2H×1/2, t, J=7.1 Hz), 7.48-7.52 (3H, m), 7.56 (1H×1/2, d, J=5.4 Hz), 7.60 (1H×1/2, d, J=5.4 Hz), 7.88-7.95 (2H, m), 8.84-8.88 (1H, m).

Mass spectrum (ESI): 448.2 (M+H).

Example 44

Trans-4'-(4-fluorophenyl)-3'-oxo-N-methyl-N-(2-pyrrolidin-1-ylethyl)-spiro[cyclohexane-1,1'-(3'H)-5'-azaisobenzofuran]-4-carboxamide

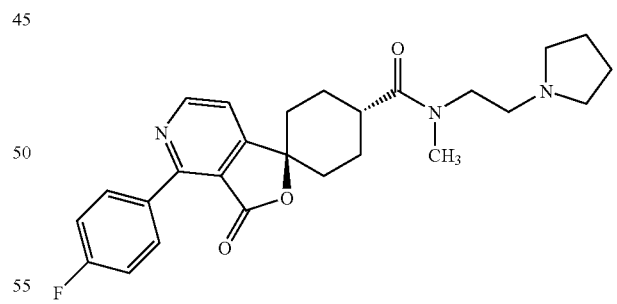

The entitled compound was obtained according to the method of Example 21 but starting from the compound obtained in Example 33 and (4-fluorophenyl)boronic acid.

$^1$HNMR (400 MHz, CDCl$_3$, δ): 1.77-1.89 (6H, m), 1.99-2.16 (4H, m), 2.35-2.47 (2H, m), 2.55-2.77 (6H, m), 2.95-3.04 (1H, m), 3.00 (3H×1/2, s), 3.14 (3H×1/2, s), 3.50 (2H×1/2, t, J=7.6 Hz), 3.61 (2H×1/2, t, J=7.3 Hz), 7.15-7.22 (2H, m), 7.53-7.61 (1H, m), 7.92-7.99 (2H, m), 8.82-8.86 (1H, m).

Mass spectrum (ESI): 452.2 (M+H).

Example 45

Trans-4'-(1-methyl-1H-pyrazol-4-yl)-3'-oxo-N-methyl-N-(2-piperidin-1-ylethyl)-spiro[cyclohexane-1,1'-(3'H)-5'-azaisobenzofuran]-4-carboxamide

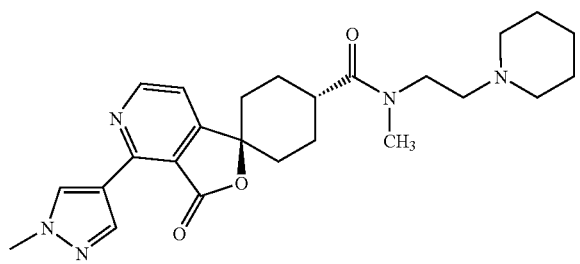

The entitled compound was obtained according to the method of Example 21 but starting from the compound obtained in Example 32 and (1-methyl-1H-pyrazol-4-yl)boronic acid.

$^1$HNMR (400 MHz, CDCl$_3$, δ): 1.40-1.50 (2H, m), 1.54-1.64 (4H, m), 1.75-1.86 (2H, m), 1.98-2.15 (4H, m), 2.31-2.56 (8H, m), 2.93-3.03 (1H, m), 2.98 (3H×1/2, s), 3.12 (3H×1/2, s), 3.46 (2H×1/2, t, J=6.8 Hz), 3.56 (2H×1/2, t, J=7.1 Hz), 4.00 (3H, s), 7.35 (1H×1/2, d, J=4.9 Hz), 7.40 (1H×1/2, d, J=4.9 Hz), 8.47 (1H, s), 8.70-8.74 (1H, m), 8.84 (1H, s).

Mass spectrum (ESI): 452.2 (M+H).

Example 46

Trans-4'-phenoxy-3'-oxo-N-methyl-N-(2-piperidin-1-ylethyl)-spiro[cyclohexane-1,1'-(3'H)-5'-azaisobenzofuran]-4-carboxamide

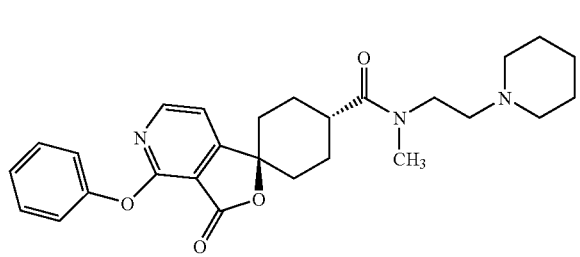

The entitled compound was obtained according to the method of Example 19 but starting from the compound obtained in Example 32 and phenol.

$^1$HNMR (400 MHz, CDCl$_3$, δ): 1.38-1.79 (6H, m), 1.80-1.91 (2H, m), 1.97-2.15 (4H, m), 2.27-2.67 (8H, m), 2.91-3.02 (1H, m), 2.98 (3H×1/2, s), 3.13 (3H×1/2, s), 3.46 (2H×1/2, t, J=7.1 Hz), 3.54-3.65 (2H×1/2, m), 7.17-7.32 (4H, m), 7.39-7.47 (2H, m), 8.29 (1H, d, J=4.9 Hz).

Mass spectrum (ESI): 464.2 (M+H).

Example 47

Trans-4'-(4-fluorophenoxy)-3'-oxo-N-methyl-N-(2-pyrrolidin-1-ylethyl)-spiro[cyclohexane-1,1'-(3'H)-5'-azaisobenzofuran]-4-carboxamide

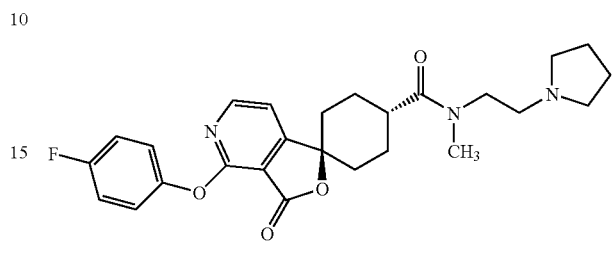

The entitled compound was obtained according to the method of Example 19 but starting from the compound obtained in Example 33 and 4-fluorophenol.

$^1$HNMR (400 MHz, CDCl$_3$, δ): 1.76-1.96 (6H, m), 1.98-2.17 (4H, m), 2.27-2.43 (2H, m), 2.52-2.88 (6H, m), 2.93-3.03 (1H, m), 2.99 (3H×1/2, s), 3.16 (3H×1/2, s), 3.46-3.73 (2H, m), 7.08-7.21 (4H, m), 7.25-7.34 (1H, m), 8.28-8.31 (1H, m).

Mass spectrum (ESI): 468.2 (M+H).

Example 48

Trans-4'-(pyrrolidin-1-yl)-3'-oxo-N-methyl-N-(2-piperidin-1-ylethyl)-spiro[cyclohexane-1,1'-(3'H)-5'-azaisobenzofuran]-4-carboxamide

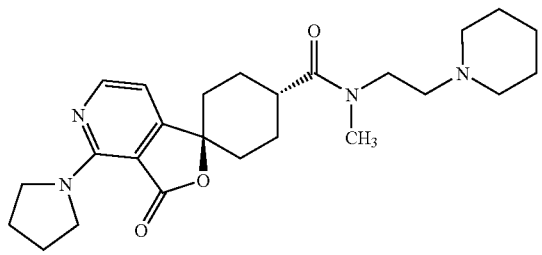

The entitled compound was obtained according to the method of Example 15 but starting from the compound obtained in Example 32 and pyrrolidine.

$^1$HNMR (400 MHz, CDCl$_3$, δ): 1.38-1.49 (2H, m), 1.52-1.62 (4H, m), 1.69-1.80 (2H, m), 1.90-2.10 (8H, m), 2.23-2.35 (2H, m), 2.38-2.54 (6H, m), 2.88-2.96 (1H, m), 2.97 (3H×1/2, s), 3.10 (3H×1/2, s), 3.44 (2H×1/2, t, J=6.8 Hz), 3.54 (2H×1/2, t, J=7.1 Hz), 3.75-3.84 (4H, m), 6.72 (1H×1/2, d, J=4.9 Hz), 6.76 (1H×1/2, d, J=5.4 Hz), 8.24-8.28 (1H, m).

Mass spectrum (ESI): 441.2 (M+H).

Example 49

Trans-4'-(piperidin-1-yl)-3'-oxo-N-methyl-N-(2-pyrrolidin-1-ylethyl)-spiro[cyclohexane-1,1'-(3'H)-5'-azaisobenzofuran]-4-carboxamide

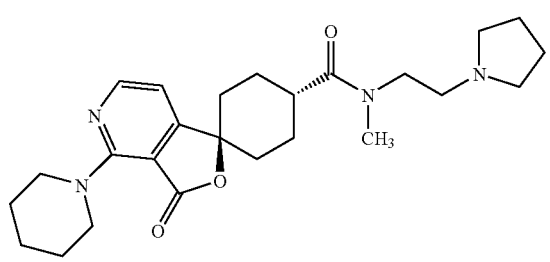

The entitled compound was obtained according to the method of Example 15 but starting from the compound obtained in Example 33 and piperidine.

$^1$HNMR (400 MHz, CDCl$_3$, δ): 1.63-1.86 (12H, m), 1.93-2.10 (4H, m), 2.21-2.35 (2H, m), 2.52-2.73 (6H, m), 2.88-2.98 (1H, m), 2.98 (3H×1/2, s), 3.11 (3H×1/2, s), 3.48 (2H×1/2, t, J=7.6 Hz), 3.57 (2H×1/2, t, J=7.3 Hz), 3.64-3.77 (4H, m), 6.79-6.88 (1H, m), 8.25-8.31 (1H, m).

Mass spectrum (ESI): 441.2 (M+H).

Example 50

Trans-4'-(pyrrolidin-1-yl)-3'-oxo-N-methyl-N-(2-pyrrolidin-1-ylethyl)-spiro[cyclohexane-1,1'-(3'H)-5'-azaisobenzofuran]-4-carboxamide

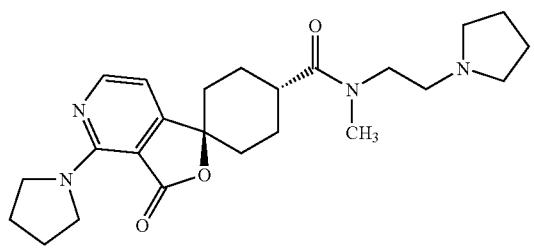

The entitled compound was obtained according to the method of Example 15 but starting from the compound obtained in Example 33 and pyrrolidine.

$^1$HNMR (400 MHz, CDCl$_3$, δ): 1.70-2.09 (14H, m), 2.22-2.35 (2H, m), 2.52-2.72 (6H, m), 2.87-2.97 (1H, m), 2.98 (3H×1/2, s), 3.11 (3H×1/2, s), 3.39-3.61 (2H, m), 3.74-3.85 (4H, m), 6.70-6.78 (1H, m), 8.23-8.29 (1H, m).

Mass spectrum (ESI): 427.2 (M+H).

Example 51

Trans-4'-(morpholin-4-yl)-3'-oxo-N-methyl-N-(2-piperidin-1-ylethyl)-spiro[cyclohexane-1,1'-(3'H)-5'-azaisobenzofuran]-4-carboxamide

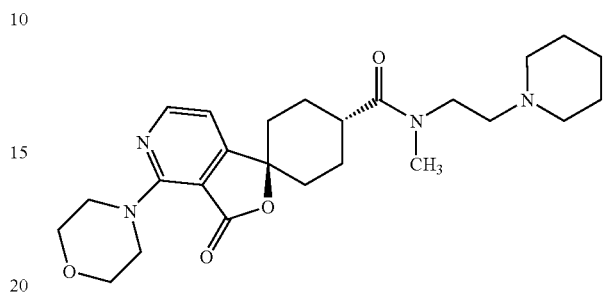

The entitled compound was obtained according to the method of Example 15 but starting from the compound obtained in Example 32 and morpholine.

$^1$HNMR (400 MHz, CDCl$_3$, δ): 1.39-1.49 (2H, m), 1.53-1.63 (4H, m), 1.68-1.84 (2H, m), 1.94-2.11 (4H, m), 2.25-2.38 (2H, m), 2.38-2.55 (6H, m), 2.90-3.00 (1H, m), 2.97 (3H×1/2, s), 3.11 (3H×1/2, s), 3.44 (2H×1/2, t, J=6.8 Hz), 3.55 (2H×1/2, t, J=7.1 Hz), 3.75-3.89 (8H, m), 6.92 (1H×1/2, d, J=4.9 Hz), 6.96 (1H×1/2, d, J=5.4 Hz), 8.29-8.34 (1H, m).

Mass spectrum (ESI): 457.2 (M+H).

Example 52

Trans-5'-(pyridin-3-yl)-3'-oxo-N-methyl-N-(2-pyrrolidin-1-ylethyl)-spiro[cyclohexane-1,1'-(3'H)-4'-azaisobenzofuran]-4-carboxamide

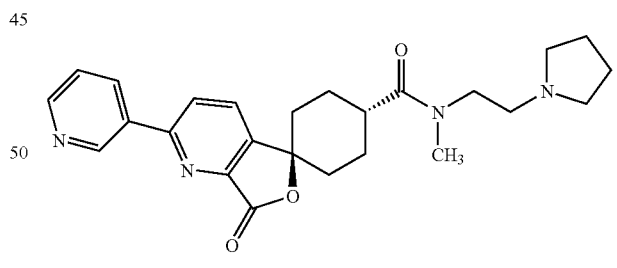

The entitled compound was obtained according to the method of Example 21 but starting from the compound obtained in Example 1 and 3-pyridine-boronic acid.

$^1$HNMR (400 MHz, CDCl$_3$, δ): 1.74-1.86 (4H, m), 1.87-2.19 (6H, m), 2.23-2.40 (2H, m), 2.52-2.75 (6H, m), 2.92-3.05 (1H, m), 3.01 (3H×1/2, s), 3.15 (3H×1/2, s), 3.51 (2H×1/2, t, J=7.4 Hz), 3.58 (2H×1/2, t, J=7.3 Hz), 7.42-7.50 (1H, m), 7.98-8.02 (1H, m), 8.20-8.28 (1H, m), 8.48-8.52 (1H, m), 8.70-8.73 (1H, m), 9.24-9.27 (1H, m).

Mass spectrum (ESI): 435.2 (M+H).

Example 53

Trans-5'-(pyridin-3-yl)-3'-oxo-N-methyl-N-(2-piperidin-1-ylethyl)-spiro[cyclohexane-1,1'-(3'H)-4'-azaisobenzofuran]-4-carboxamide

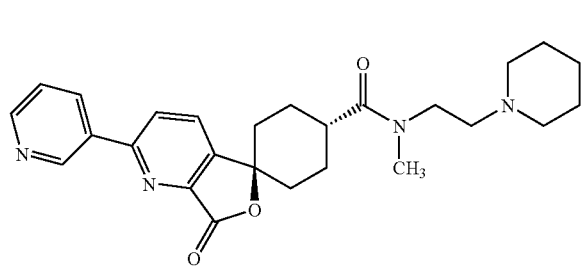

The entitled compound was obtained according to the method of Example 21 but starting from the compound obtained in Example 4 and 3-pyridine-boronic acid.

¹HNMR (400 MHz, CDCl₃, δ): 1.38-1.51 (2H, m), 1.53-1.68 (4H, m), 1.86-2.16 (6H, m), 2.26-2.38 (2H, m), 2.41-2.63 (6H, m), 2.92-3.03 (1H, m), 3.00 (3H×1/2, s), 3.15 (3H×1/2, s), 3.43-3.64 (2H, m), 7.41-7.49 (1H, m), 7.96-8.03 (1H, m), 8.18-8.29 (1H, m), 8.46-8.54 (1H, m), 8.68-8.75 (1H, m), 9.26 (1H, s).

Mass spectrum (ESI): 449.2 (M+H).

Example 54

Trans-5'-pyrazinyl-3'-oxo-N-methyl-N-(2-piperidin-1-ylethyl)-spiro[cyclohexane-1,1'-(3'H)-4'-azisobenzofuran]-4-carboxamide

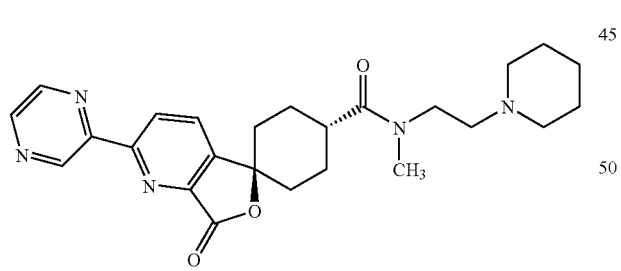

The entitled compound was obtained according to the method of Example 21 but starting from the compound obtained in Example 4 and 2-(tri-n-butyltin)pyrazine.

¹HNMR (400 MHz, CDCl₃, δ): 1.38-1.72 (6H, m), 1.87-2.20 (6H, m), 2.30-2.65 (8H, m), 2.94-3.03 (1H, m), 3.00 (3H×1/2, s), 3.15 (3H×1/2, s), 3.42-3.69 (2H, m), 8.19-8.30 (1H, m), 8.62-8.70 (3H, m), 9.83 (1H×1/2, s), 9.84 (1H×1/2, s).

Mass spectrum (ESI): 450.2 (M+H).

Example 55

Trans-5'-benzyloxy-3'-oxo-N-methyl-N-(2-piperidin-1-ylethyl)-spiro[cyclohexane-1,1'-(3'H)-4'-azaisobenzofuran]-4-carboxamide

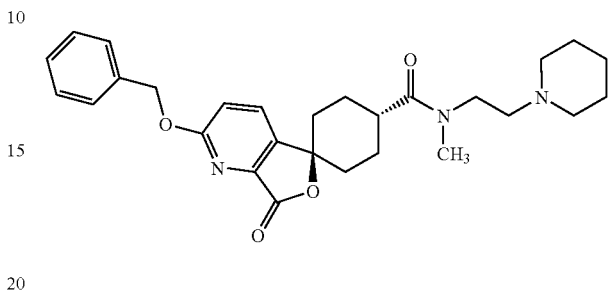

The entitled compound was obtained according to the method of Example 10 but starting from the compound obtained in Example 4 and benzyl alcohol.

¹HNMR (400 MHz, CDCl₃, δ): 1.38-1.51 (2H, m), 1.52-1.69 (4H, m), 1.82-1.95 (2H, m), 1.96-2.12 (4H, m), 2.15-2.59 (8H, m), 2.87-2.97 (1H, m), 2.98 (3H×1/2, s), 3.13 (3H×1/2, s), 3.42-3.62 (2H, m), 5.51 (2H, s), 7.01-7.08 (1H, m), 7.31-7.44 (3H, m), 7.46-7.52 (2H, m), 7.93-8.05 (1H, m).

Mass spectrum (ESI): 478.1 (M+H).

Example 56

Trans-5'-hydroxy-3'-oxo-N-methyl-N-(2-piperidin-1-ylethyl)-spiro[cyclohexane-1,1'-(3'H)-4'-azaisobenzofuran]-4-carboxamide

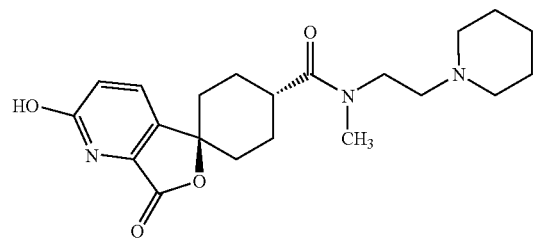

The compound (440 mg) obtained in Example 55 was dissolved in ethyl acetate (10 mL) and methanol (10 mL), added 10% palladium carbon (250 mg), and stirred for 2 hr in a hydrogen atmosphere at room temperature. After filtering the catalyst, the filtrate was concentrated in vacuo to obtain the entitled compound (331 mg, 100%) as a colorless solid.

¹HNMR (400 MHz, CDCl₃, δ): 1.39-1.68 (6H, m), 1.70-2.12 (6H, m), 2.15-2.35 (2H, m), 2.42-2.61 (6H, m), 2.69-3.03 (1H, m), 2.96 (3H×1/2, s), 3.17 (3H×1/2, s), 3.44-3.56 (2H×1/2, m), 3.68-3.84 (2H×1/2, m), 6.81-6.95 (1H, m), 7.63-7.83 (1H, m).

Mass spectrum (ESI): 388.2 (M+H).

Example 57

Trans-6'-bromo-5'-methoxy-3'-oxo-N-methyl-N-(2-piperidin-1-ylethyl)-spiro[cyclohexane-1,1'-(3'H)-4'-azaisobenzofuran]-4-carboxamide

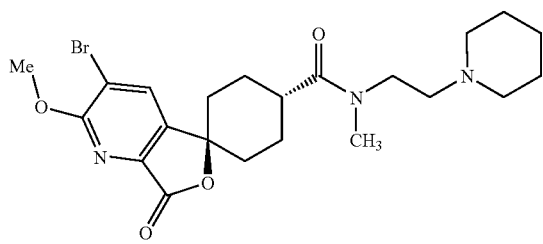

The entitled compound was obtained according to the method of Example 1 but starting from the compound obtained in Reference Example 4 (5) and N-methyl-N-(piperidinoethyl)amine.

$^1$HNMR (400 MHz, CDCl$_3$, δ): 1.39-1.50 (2H, m), 1.52-1.62 (4H, m), 1.65-2.12 (6H, m), 2.26-2.53 (8H, m), 2.89-3.00 (1H, m), 2.98 (3H×1/2, s), 3.11 (3H×1/2, s), 3.45 (2H×1/2, t, J=7.1 Hz), 3.54 (2H×1/2, t, J=7.0 Hz), 4.14 (3H, s), 8.17 (1H×1/2, s), 8.22 (1H×1/2, s).

Mass spectrum (ESI): 480/482 (M+H).

Reference Example 1

Production of trans-5'-chloro-3'-oxo-spiro[cyclohexane-1,1'-(3'H)-4'-azaisobenzofuran]-4-carboxylic acid

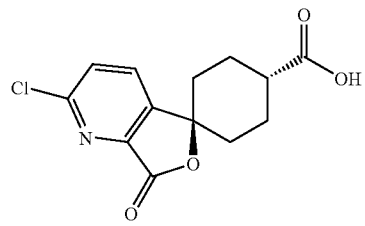

(1) Production of methyl trans-5'-chloro-3'-oxo-spiro[cyclohexane-1,1'-(3'H)-4'-azaisobenzofuran]-4-carboxylate Methanol (200 mL) and p-toluenesulfonic acid monohydrate (5.00 g) were added to trans-3'-oxo-spiro[cyclohexane-1,1'-(3'H)-4'-azaisobenzofuran]-4-carboxylic acid (5.00 g), and heated under reflux for 6 hours. The reaction liquid was concentrated under reduced pressure, saturated sodium bicarbonate water was added thereto and extracted with ethyl acetate. The organic layer was washed with saturated saline water, dried with sodium sulfate, filtered and concentrated under reduced pressure. The resulting residue was dissolved in acetonitrile (200 mL), then urea-hydrogen peroxide adduct (3.75 g) was added thereto at 0° C., and trifluoroacetic anhydride (5.63 mL) was dropwise added thereto. Next, this was stirred at room temperature for 4 hours. Aqueous 10% sodium thiosulfate solution was added to it, neutralized with saturated sodium bicarbonate water, and extracted with ethyl acetate. The organic layer was dried with sodium sulfate, filtered, and concentrated under reduced pressure. Phosphorus oxychloride (50 mL) was added to the resulting residue, and stirred at 100° C. for 2 hours. The reaction liquid was concentrated under reduced pressure, then water and chloroform were added thereto, and neutralized with potassium carbonate. The organic layer was dried with sodium sulfate, filtered, and concentrated under reduced pressure. The resulting solid was suspended in ethyl acetate added thereto, and then filtered to obtain the intended compound (3.89 g, 65%) as a colorless solid.

$^1$HNMR (400 MHz, CDCl$_3$, δ): 1.70-1.82 (2H, m), 2.06-2.20 (6H, m), 2.80-2.86 (1H, m), 3.76 (3H, s), 7.57 (1H, d, J=8.2 Hz), 7.84 (1H, d, J=8.2 Hz).

(2) Production of trans-5'-chloro-3'-oxo-spiro[cyclohexane-1,1'-(3'H)-4'-azaisobenzofuran]-4-carboxylic acid Methanol (120 mL) was added to the compound (3.00 g) obtained in the above (1), and then aqueous 2 N sodium hydroxide solution (24 mL) was added thereto and stirred at room temperature for 9 hours. The reaction liquid was made to have a pH of 2 with 2 N hydrochloric acid at 0° C., then the precipitated solid was taken out through filtration, and dried at 50° C. under reduced pressure to obtain the entitled compound (2.53 g, 89%) as a colorless solid.

$^1$HNMR (400 MHz, DMSO-d$_6$, δ): 1.70-1.85 (2H, m), 1.85-2.10 (6H, m), 2.63-2.75 (1H, m), 7.83 (1H, d, J=8.3 Hz), 8.30 (1H, d, J=8.3 Hz), 12.34 (1H, brs).

Reference Example 2

Production of 6'-fluoro-1'-oxo-1'H-spiro[cyclohexane-1,3'-furo[3,4-c]pyridine]-4-carboxylic acid

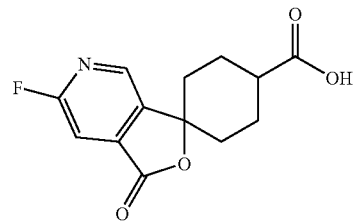

(1) 7''-Chloro-6''-fluoro-1''H-dispiro[1,3-dioxolan-2,1'-cyclohexane-4',3''-furo[3,4-c]pyridin]-1''-one At −60° C., n-butyllithium (1.50 M hexane solution) (75.9 mL) was dropwise added to tetrahydrofuran (100 mL) solution of 2,2,6,6-tetramethylpiperidine (12.5 g), and stirred at −78° C. for 30 minutes. At −78° C., 3-chloro-2-fluoroisonicotinic acid (5.00 g) was added to the reaction liquid, and stirred at −78° C. for 2 hours. Then, at −78° C., tetrahydrofuran (50 mL) solution of 1,4-dioxaspiro[4.5]decan-8-one (5.78 g) was added to the reaction liquid, and stirred for 30 minutes at −78° C. The reaction liquid was warmed up under cooling with ice, and water and hexane were added thereto in that order. The aqueous layer and the organic layer were separated from each other, then the aqueous layer was made acidic (pH of 1 to 2) with 2 M hydrochloric acid added thereto and the stirred at room temperature for 2 hours. The formed solid was taken out through filtration, washed with water, and dried under reduced pressure to obtain the entitled compound (4.39 g, 49%) as a pale brown solid.

$^1$HNMR (300 MHz, CDCl$_3$, δ): 1.79-1.93 (4H, m), 2.07-2.20 (2H, m), 2.24-2.39 (2H, m), 3.98-4.08 (4H, m), 8.25 (1H, s).

(2) 6'-Fluoro-1'H,4H-spiro[cyclohexane-1,3'-furo[3,4-c]pyridin]-1',4-dione

Triethylamine (2.00 mL) and a catalyst, 10% palladium-carbon (500 mg) were added in that order to tetrahydrofuran (60 mL) solution of the compound (4.38 g) obtained in the above (1), and stirred overnight in a hydrogen atmosphere at room temperature. The catalyst was filtered off, the solvent was evaporated off under reduced pressure, and the resulting residue was washed with ethyl acetate and dried under reduced pressure. At room temperature, water (40 mL) and p-toluenesulfonic acid monohydrate (274 mg) were added in that order to acetone (40 mL) solution of the resulting residue (4.01 g), and stirred overnight with heating under reflux. The reaction liquid was cooled to room temperature, and the solvent was evaporated off under reduced pressure. The resulting residue was diluted with saturated sodium bicarbonate water, and extracted with ethyl acetate. The organic layer was dried with sodium sulfate, filtered and concentrated under reduced pressure. The residue was purified through silica gel column chromatography (ethyl acetate/hexane=33% to 50%) to obtain the entitled compound (2.36 g, 72%) as a pale yellow solid.

$^1$HNMR (300 MHz, CDCl$_3$, δ): 2.18-2.30 (2H, m), 2.43-2.62 (4H, m), 2.89-3.03 (2H, m), 7.40-7.43 (1H, m), 8.43 (1H, s).

(3) 6'-Fluoro-4-methylene-1'H-spiro[cyclohexane-1,3'-furo[3,4-c]pyridin]-1'-one

At −78° C., n-butyllithium (2.6 M hexane solution) (33.0 mL) was added to tetrahydrofuran (300 mL) suspension of (methyl)triphenylphosphonium bromide (34.9 g), then warmed up to 0° C., and stirred for 2 hours. The reaction liquid was cooled to −78° C., then tetrahydrofuran (200 mL) solution of the compound (10.4 g) obtained in the above (2) was added to it at −78° C. The reaction liquid was warmed up to room temperature, and then made to have a pH of from 4 to 5 with 1 M hydrochloric acid added thereto. The reaction liquid was stirred overnight, then diluted with water, and extracted with ethyl acetate. The organic layer was dried with magnesium sulfate, filtered and concentrated under reduced pressure. The residue was purified through silica gel column chromatography (ethyl acetate/hexane=4% to 5% to 50%) to obtain the entitled compound (6.00 g, 58%).

$^1$HNMR (300 MHz, CDCl$_3$, δ): 1.91-2.14 (4H, m), 2.38-2.49 (2H, m), 2.54-2.70 (2H, m), 4.87 (2H, s), 7.33-7.40 (1H, m), 8.38 (1H, s).

(4) 6'-Fluoro-1'-oxo-1'H-spiro[cyclohexane-1,3'-furo[3,4-c]pyridin]-4-carboxylic acid With cooling with ice, borane methyl sulfide complex (2.75 mL) was added to tetrahydrofuran (100 mL) solution of the compound (5.82 g) obtained in the above (4). The reaction liquid was warmed up to room temperature, and stirred for 1 hour. With cooling with ice, aqueous 4 M sodium hydroxide solution (40 mL) and 30% hydrogen peroxide (40 mL) were added in that order to the reaction liquid, and then warmed up to room temperature. At 0° C., 6 M hydrochloric acid was added to the reaction liquid so as to make the liquid has a pH of 4, and then stirred for 1 hour. The reaction liquid was extracted with ethyl acetate added thereto, and the organic layer was dried with magnesium sulfate, filtered, and concentrated under reduced pressure. The residue was purified through silica gel column chromatography (hexane/ethyl acetate=50% to 60% to 66%). With cooling with ice, John's reagent (10 mL) was added to acetone (90 mL) solution of the resulting residue (6.50 g). With cooling with ice, this was stirred for 1 hour. The reaction liquid was diluted with water and extracted with ethyl acetate. The organic layer was dried with magnesium sulfate, filtered, and concentrated under reduced pressure to obtain the entitled compound (4.53 g, 68%) as a white solid.

$^1$HNMR (400 MHz, CDCl$_3$, δ): 1.80-2.35 (8H, m), 2.90-2.99 (1H, m), 7.35-7.40 (1H, m), 8.40-8.50 (1H, m).

Reference Example 3

Production of trans-4'-chloro-3'-oxo-spiro[cyclohexane-1,1'-(3'H)-5'-azaisobenzofuran]-4-carboxylic acid

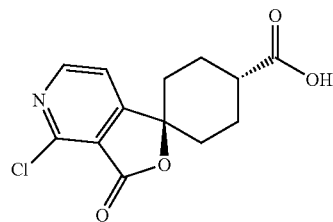

The entitled compound was obtained according to the method of Reference Example 1 but starting from trans-3'-oxo-spiro[cyclohexane-1,1'-(3'H)-5'-azaisobenzofuran]-4-carboxylic acid.

$^1$HNMR (400 MHz, CDCl$_3$, δ): 1.71-1.84 (2H, m), 2.07-2.31 (6H, m), 2.89-2.98 (1H, m), 7.39 (1H, d, J=4.9 Hz), 8.64 (1H, d, J=4.9 Hz).

Reference Example 4

Production of trans-6'-bromo-5'-methoxy-3'-oxo-spiro[cyclohexane-1,1'-(3'H)-4'-azaisobenzofuran]-4-carboxylic acid

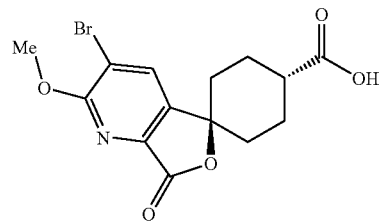

(1) Production of trans-5'-benzyloxy-3'-oxo-spiro[cyclohexane-1,1'-(3'H)-4'-azaisobenzofuran]-4-carboxylic acid Benzyl alcohol (770 mg) was dissolved in DMF (10 mL), and sodium hydride (340 mg) was added thereto at 0° C., and stirred for 20 minutes at 0° C. Trans-5'-chloro-3'-oxo-spiro[cyclohexane-1,1'-(3'H)-4'-azaisobenzofuran]-4-carboxylic acid (500 mg) obtained in Reference Example 1 was added to the solution, and stirred at 60° C. for 2 hours.

At 0° C., this was made to have a pH of 2 with 6 N hydrochloric acid, and extracted with ethyl acetate. The organic layer was washed with saturated saline water, dried with sodium sulfate, filtered, and concentrated under reduced pressure. The resulting residue was purified through silica gel column chromatography (Biotage Column, chloroform/methanol=1% to 5%, gradient) to obtain the entitled compound (532 mg, 85%) as a colorless solid.

$^1$HNMR (400 MHz, CDCl$_3$, δ): 1.70-1.83 (2H, m), 2.02-2.28 (6H, m), 2.85-2.94 (1H, m), 5.51 (2H, s), 7.05 (1H, d, J=8.3 Hz), 7.31-7.43 (3H, m), 7.46-7.52 (2H, m), 7.72 (1H, d, J=8.3 Hz).

(2) Production of methyl trans-5'-benzyloxy-3'-oxo-spiro[cyclohexane-1,1'-(3'H)-4'-azaisobenzofuran]-4-carboxylate Methanol (5.0 mL) and p-toluenesulfonic acid monohydrate (400 mg) were added to the compound (460 mg) obtained in the above (1), and heated under reflux for 3 hours. This was neutralized with saturated sodium bicarbonate water added thereto, and then extracted with ethyl acetate. The organic layer was washed with saturated saline water, dried with sodium sulfate, filtered and concentrated under reduced pressure to obtain the entitled compound (467 mg, 98%) as a colorless solid.

$^1$HNMR (400 MHz, CDCl$_3$, δ): 1.69-1.80 (2H, m), 2.02-2.21 (6H, m), 2.77-2.85 (1H, m), 3.76 (3H, s), 5.51 (2H, s), 7.05 (1H, d, J=8.3 Hz), 7.31-7.43 (3H, m), 7.46-7.52 (2H, m), 7.73 (1H, d, J=8.8 Hz).

(3) Production of methyl trans-5'-hydroxy-3'-oxo-spiro[cyclohexane-1,1'-(3'H)-4'-azaisobenzofuran]-4-carboxylate The compound (440 mg) obtained in the above (2) was dissolved in methanol (20 mL) and ethyl acetate (10 mL), then 10% palladium-carbon (250 mg) was added thereto and stirred in a hydrogen atmosphere at room temperature for 2 hours. The reaction liquid was filtered through Celite, and the filtrate was concentrated under reduced pressure to obtain the entitled compound (331 mg, 100%) as a colorless solid.

$^1$HNMR (400 MHz, DMSO-d$_6$, δ): 1.61-1.73 (2H, m), 1.85-2.07 (6H, m), 2.75-2.82 (1H, m), 3.67 (3H, s), 6.84 (1H, d, J=8.8 Hz), 7.90 (1H, d, J=8.8 Hz), 12.16 (1H, s).

(4) Production of methyl trans-6'-bromo-5'-methoxy-3'-oxo-spiro[cyclohexane-1,1'-(3'H)-4'-azaisobenzofuran]-4-carboxylate The compound (320 mg) obtained in the above (3) was dissolved in DMF (6.0 mL), and N-bromosuccinimide (247 mg) was added thereto and stirred at room temperature for 4 hours. The reaction liquid was concentrated, and the resulting residue was purified through silica gel column chromatography (Biotage Column, chloroform/methanol=0% to 6%, gradient) to obtain the entitled compound (520 mg) as a colorless solid of a roughly-purified product.

Chloroform (20 mL) was added to the obtained, roughly-purified product (200 mg), and silver carbonate (500 mg) and methyl iodide (1.0 mL) were added thereto and stirred at 40° C. for 7 hours. Methyl iodide (1.0 mL) was added to it, and further stirred for 22 hours. The reaction liquid was filtered through Celite, the filtrate was concentrated under reduced pressure, and the resulting residue was purified through silica gel column chromatography (Biotage Column, hexane/ethyl acetate=0% to 100%, gradient) to obtain the entitled compound (112 mg, 68%) as a colorless solid.

$^1$HNMR (400 MHz, CDCl$_3$, δ): 1.68-1.78 (2H, m), 2.00-2.19 (6H, m), 2.78-2.85 (1H, m), 3.76 (3H, s), 4.14 (3H, s), 7.96 (1H, s).

(5) Production of trans-6'-bromo-5'-methoxy-3'-oxo-spiro[cyclohexane-1,1'-(3'H)-4'-azaisobenzofuran]-4-carboxylic acid Methanol (5.0 mL) was added to the compound (154 mg) obtained in the above (4), and aqueous 2 N sodium hydroxide solution (0.83 mL) was added to it, and stirred at room temperature for 16 hours. At 0° C., the reaction liquid was made to have a pH of 2 with 2 N hydrochloric acid, and extracted with ethyl acetate. The organic layer was washed with saturated saline water, dried with sodium sulfate, filtered, and concentrated under reduced pressure to obtain the entitled compound (145 mg, 98%) as a colorless solid.

$^1$HNMR (400 MHz, CDCl$_3$, δ): 1.70-1.82 (2H, m), 2.02-2.25 (6H, m), 2.87-2.95 (1H, m), 4.15 (3H, s), 7.97 (1H, s).

Pharmaceutical test examples with the compounds of Examples are described below.

Pharmaceutical Test Example 1

Histamine Analogue-binding Inhibition Test

A cDNA sequence coding for a human histamine-H3 receptor [see WO00/39164) was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see Proceedings of the National Academy of Sciences of the United States of America, Vol., 84, p. 7413 (1987)] to obtain histamine-H3 receptor expression cells.

A membrane specimen prepared from the cells having expressed a histamine-H3 receptor was incubated in an assay buffer (50 mM Tris buffer, pH 7.4) along with a test compound and 20,000 cpm [3H]N-α-methylhistamine (by NEN) therein, at 25° C. for 2 hours, and then filtered through a glass filter GF/C. After washed with 50 mM Tris buffer (pH 7.4), the radioactivity on the glass filter was determined. The non-specific binding was determined in the presence of 10 μM thioperamide (by SIGAM), and the 50% inhibitory concentration (IC$_{50}$) of the test compound to the specific N-alpha-methylhistamine binding was calculated [see Molecular Pharmacology, Vol. 55, p. 1101 (1999)]. Table 1 shows the result of the test.

TABLE 1

| example compound | IC50 (nM) |
| --- | --- |
| 3 | 0.72 |
| 11 | 0.92 |
| 13 | 0.92 |
| 17 | 1.90 |
| 21 | 0.42 |
| 34 | 0.32 |
| 41 | 0.51 |
| 45 | 0.14 |
| 54 | 0.07 |

As in the above, the compounds of the invention strongly inhibited the binding of N-alpha-methylhistamine (histamine analogue) to histamine-H3 receptor.

Industrial Applicability

The present compounds have a strong histamine-H3 receptor antagonistic or inverse-agonistic activity, and are useful for prevention or remedy of metabolic system diseases such as obesity, diabetes, hormone secretion disorder, hyperlipemia, gout, fatty liver; circulatory system diseases such as stenocardia, acute/congestive cardiac insufficiency, cardiac infarction, coronary arteriosclerosis, hypertension, nephropathy, electrolyte abnormality; or central or peripheral nervous system diseases such as sleep disorder, various diseases accompanied by sleep disorder (e.g., idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia), bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism, tremor et al.

The invention claimed is:

1. A compound which is selected from the group consisting of:
    trans-5'-chloro-3'-oxo-N-methyl-N-(2-pyrrolidin-1-ylethyl)-spiro[cyclohexane-1,1'-(3'H)-4'-azaisobenzofuran]-4-carboxamide,
    trans-3'-oxo-N-methyl-N-(2-piperidin-1-ylethyl)-spiro[cyclohexane-1,1'-(3'H)-4'-azaisobenzofuran]-4-carboxamide,
    trans-3'-oxo-N-methyl-N-(2-pyrrolidin-1-ylethyl)-spiro[cyclohexane-1,1'-(3'H)-4'-azaisobenzofuran]-4-carboxamide,
    trans-5'-chloro-3'-oxo-N-methyl-N-(2-piperidin-1-ylethyl)-spiro[cyclohexane-1,1'-(3'H)-4'-azaisobenzofuran]-4-carboxamide,
    trans-3'-oxo-N-methyl-N-(2-piperidin-1-ylethyl)-spiro[cyclohexane-1,1'-(3'H)-5'-azaisobenzofuran]-4-carboxamide,
    trans-3'-oxo-N-methyl-N-(2-pyrrolidin-1-ylethyl)-spiro[cyclohexane-1,1'-(3'H)-5'-azaisobenzofuran]-4-carboxamide,
    trans-3'-oxo-N-methyl-N-(2-piperidin-1-ylethyl)-spiro[cyclohexane-1,1'-(3'H)-6'-azaisobenzofuran]-4-carboxamide,
    trans-3'-oxo-N-methyl-N-(2-piperidin-1-ylethyl)-spiro[cyclohexane-1,1'-(3'H)-7'-azaisobenzofuran]-4-carboxamide,
    trans-5'-fluoro-3'-oxo-N-methyl-N-(2-pyrrolidin-1-ylethyl)-spiro[cyclohexane-1,1'-(3'H)-6'-azaisobenzofuran]-4-carboxamide,
    trans-5'-ethoxy-3'-oxo-N-methyl-N-(2-pyrrolidin-1-ylethyl)-spiro[cyclohexane-1,1'-(3'H)-4'-azaisobenzofuran]-4-carboxamide,
    trans-5'-methoxy-3'-oxo-N-methyl-N-(2-piperidin-1-ylethyl)-spiro[cyclohexane-1,1'-(3'H)-4'-azaisobenzofuran]-4-carboxamide,
    trans-5'-ethoxy-3'-oxo-N-methyl-N-(2-piperidin-1-ylethyl)-spiro[cyclohexane-1,1'-(3'H)-4'-azaisobenzofuran]-4-carboxamide,
    trans-5'-methoxy-3'-oxo-N-methyl-N-(2-pyrrolidin-1-ylethyl)-spiro[cyclohexane-1,1'-(3'H)-4'-azaisobenzofuran]-4-carboxamide,
    trans-5'-propoxy-3'-oxo-N-methyl-N-(2-pyrrolidin-1-ylethyl)-spiro[cyclohexane-1,1'-(3'H)-4'-azaisobenzofuran]-4-carboxamide,
    trans-5'-(morpholin-4-yl)-3'-oxo-N-methyl-N-(2-pyrrolidin-1-ylethyl)-spiro[cyclohexane-1,1'-(3'H)-4'-azaisobenzofuran]-4-carboxamide,
    trans-5'-(dimethylamino)-3'-oxo-N-methyl-N-(2-pyrrolidin-1-ylethyl)-spiro[cyclohexane-1,1'-(3'H)-4'-azaisobenzofuran]-4-carboxamide,
    trans-5'-(piperidin-1-yl)-3'-oxo-N-methyl-N-(2-pyrrolidin-1-ylethyl)-spiro[cyclohexane-1,1'-(3'H)-4'-azaisobenzofuran]-4-carboxamide,
    trans-5'-(piperidin-1-yl)-3'-oxo-N-methyl-N-(2-piperidin-1-ylethyl)-spiro[cyclohexane-1,1'-(3'H)-4'-azaisobenzofuran]-4-carboxamide,
    trans-5'-phenoxy-3'-oxo-N-methyl-N-(2-piperidin-1-ylethyl)-spiro[cyclohexane-1,1'-(3'H)-4'-azaisobenzofuran]-4-carboxamide,
    trans-5'-(pyridin-3-yloxy)-3'-oxo-N-methyl-N-(2-piperidin-1-ylethyl)-spiro[cyclohexane-1,1'-(3'H)-4'-azaisobenzofuran]-4-carboxamide,
    trans-5'-phenyl-3'-oxo-N-methyl-N-(2-pyrrolidin-1-ylethyl)-spiro[cyclohexane-1,1'-(3'H)-4'-azaisobenzofuran]-4-carboxamide,
    trans-5'-phenyl-3'-oxo-N-methyl-N-(2-piperidin-1-ylethyl)-spiro[cyclohexane-1,1'-(3'H)-4'-azaisobenzofuran]-4-carboxamide,
    trans-5'-(4-fluorophenyl)-3'-oxo-N-methyl-N-(2-piperidin-1-ylethyl)-spiro[cyclohexane-1,1'-(3'H)-4'-azaisobenzofuran]-4-carboxamide,
    trans-5'-(pyrimidin-5-yl)-3'-oxo-N-methyl-N-(2-piperidin-1-ylethyl)-spiro[cyclohexane-1,1'-(3'H)-4'-azaisobenzofuran]-4-carboxamide,
    trans-5'-(6-methoxypyridin-3-yl)-3'-oxo-N-methyl-N-(2-piperidin-1-ylethyl)-spiro[cyclohexane-1,1'-(3'H)-4'-azaisobenzofuran]-4-carboxamide,
    trans-5'-[4-(methylsulfonyl)phenyl]-3'-oxo-N-methyl-N-(2-piperidin-1-ylethyl)-spiro[cyclohexane-1,1'-(3'H)-4'-azaisobenzofuran]-4-carboxamide,
    trans-5'-(6-methoxypyridin-3-yl)-3'-oxo-N-methyl-N-(2-pyrrolidin-1-ylethyl)-spiro[cyclohexane-1,1'-(3'H)-4'-azaisobenzofuran]-4-carboxamide,
    trans-5'-(1-methyl-1H-pyrazol-4-yl)-3'-oxo-N-methyl-N-(2-piperidin-1-ylethyl)-spiro[cyclohexane-1,1'-(3'H)-4'-azaisobenzofuran]-4-carboxamide,
    trans-5'-(2,4-dimethoxypyrimidin-5-yl)-3'-oxo-N-methyl-N-(2-piperidin-1-ylethyl)-spiro[cyclohexane-1,1'-(3'H)-4'-azaisobenzofuran]-4-carboxamide,
    trans-5'-ethyl-3'-oxo-N-methyl-N-(2-piperidin-1-ylethyl)-spiro[cyclohexane-1,1'-(3'H)-4'-azaisobenzofuran]-4-carboxamide,
    N-methyl-7'-oxo-N-(2-piperidin-1-ylethyl)-7'H-spiro[cyclohexane-1,5'-furo[3,4-b]pyridine]-4-carboxamide,
    trans-4'-chloro-3'-oxo-N-methyl-N-(2-piperidin-1-ylethyl)-spiro[cyclohexane-1,1'-(3'H)-5'-azaisobenzofuran]-4-carboxamide,
    trans-4'-chloro-3'-oxo-N-methyl-N-(2-pyrrolidin-1-ylethyl)-spiro[cyclohexane-1,1'-(3'H)-5'-azaisobenzofuran]-4-carboxamide,
    trans-4'-methoxy-3'-oxo-N-methyl-N-(2-piperidin-1-ylethyl)-spiro[cyclohexane-1,1'-(3'H)-5'-azaisobenzofuran]-4-carboxamide,
    trans-4'-methoxy-3'-oxo-N-methyl-N-(2-pyrrolidin-1-ylethyl)-spiro[cyclohexane-1,1'-(3'H)-5'-azaisobenzofuran]-4-carboxamide, trans-4'-ethoxy-3'-oxo-N-methyl-N-(2-piperidin-1-yl-ethyl)-spiro[cyclohexane-1,1'-(3'H)-5'-azaisobenzofuran]-4-carboxamide,
trans-4'-ethoxy-3'-oxo-N-methyl-N-(2-pyrrolidin-1-yl-ethyl)-spiro[cyclohexane-1,1'-(3'H)-5'-azaisobenzofuran]-4-carboxamide,
trans-4'-isopropoxy-3'-oxo-N-methyl-N-(2-piperidin-1-ylethyl)-spiro[cyclohexane-1,1'-(3'H)-5'-azaisobenzofuran]-4-carboxamide,
trans-4'-isopropoxy-3'-oxo-N-methyl-N-(2-pyrrolidin-1-ylethyl)-spiro[cyclohexane-1,1'-(3'H)-5'-azaisobenzofuran]-4-carboxamide,
trans-4'-cyclopropylmethoxy-3'-oxo-N-methyl-N-(2-pyrrolidin-1-ylethyl)-spiro[cyclohexane-1,1'-(3'H)-5'-azaisobenzofuran]-4-carboxamide,
trans-4'-methyl-3'-oxo-N-methyl-N-(2-piperidin-1-yl-ethyl)-spiro[cyclohexane-1,1'-(3'H)-5'-azaisobenzofuran]-4-carboxamide,
trans-4'-ethyl-3'-oxo-N-methyl-N-(2-pyrrolidin-1-yl-ethyl)-spiro[cyclohexane-1,1'-(3'H)-5'-azaisobenzofuran]-4-carboxamide,
trans-4'-phenyl-3'-oxo-N-methyl-N-(2-piperidin-1-yl-ethyl)-spiro[cyclohexane-1,1'-(3'H)-5'-azaisobenzofuran]-4-carboxamide,
trans-4'-(4-fluorophenyl)-3'-oxo-N-methyl-N-(2-pyrrolidin-1-ylethyl)-spiro[cyclohexane-1,1'-(3'H)-5'-azaisobenzofuran]-4-carboxamide,
trans-4'-(1-methyl-1H-pyrazol-4-yl)-3'-oxo-N-methyl-N-(2-piperidin-1-ylethyl)-spiro[cyclohexane-1,1'-(3'H)-5'-azaisobenzofuran]-4-carboxamide,
trans-4'-phenoxy-3'-oxo-N-methyl-N-(2-piperidin-1-yl-ethyl)-spiro[cyclohexane-1,1'-(3'H)-5'-azaisobenzofuran]-4-carboxamide,
trans-4'-(4-fluorophenoxy)-3'-oxo-N-methyl-N-(2-pyrrolidin-1-ylethyl)-spiro[cyclohexane-1,1'-(3'H)-5'-azaisobenzofuran]-4-carboxamide,
trans-4'-(pyrrolidin-1-yl)-3'-oxo-N-methyl-N-(2-piperidin-1-ylethyl)-spiro[cyclohexane-1,1'-(3'H)-5'-azaisobenzofuran]-4-carboxamide,
trans-4'-(piperidin-1-yl)-3'-oxo-N-methyl-N-(2-pyrrolidin-1-ylethyl)-spiro[cyclohexane-1,1'-(3'H)-5'-azaisobenzofuran]-4-carboxamide,
trans-4'-(pyrrolidin-1-yl)-3'-oxo-N-methyl-N-(2-pyrrolidin-1-ylethyl)-spiro[cyclohexane-1,1'-(3'H)-5'-azaisobenzofuran]-4-carboxamide,
trans-4'-(morpholin-4-yl)-3'-oxo-N-methyl-N-(2-piperidin-1-ylethyl)-spiro[cyclohexane-1,1'-(3'H)-5'-azaisobenzofuran]-4-carboxamide,
trans-5'-(pyridin-3-yl)-3'-oxo-N-methyl-N-(2-pyrrolidin-1-ylethyl)-spiro[cyclohexane-1,1'-(3'H)-4'-azaisobenzofuran]-4-carboxamide,
trans-5'-(pyridin-3-yl)-3'-oxo-N-methyl-N-(2-piperidin-1-ylethyl)-spiro[cyclohexane-1,1'-(3'H)-4'-azaisobenzofuran]-4-carboxamide,
trans-5'-pyrazinyl-3'-oxo-N-methyl-N-(2-piperidin-1-yl-ethyl)-spiro[cyclohexane-1,1'-(3'H)-4'-azaisobenzofuran]-4-carboxamide,
trans-5'-benzyloxy-3'-oxo-N-methyl-N-(2-piperidin-1-yl-ethyl)-spiro[cyclohexane-1,1'-(3'H)-4'-azaisobenzofuran]-4-carboxamide,
trans-5'-hydroxy-3'-oxo-N-methyl-N-(2-piperidin-1-yl-ethyl)-spiro[cyclohexane-1,1'-(3'H)-4'-azaisobenzofuran]-4-carboxamide, and
trans-6'-bromo-5'-methoxy-3'-oxo-N-methyl-N-(2-piperidin-1-ylethyl)-spiro[cyclohexane-1,1'-(3'H)-4'-azaisobenzofuran]-4-carboxamide,
or a pharmaceutically acceptable salt thereof.

2. A compound which is selected from the group consisting of:
trans-5'-methoxy-3'-oxo-N-methyl-N-(2-piperidin-1-yl-ethyl)-spiro[cyclohexane-1,1'-(3'H)-4'-azaisobenzofuran]-4-carboxamide;
trans-5'-methoxy-3'-oxo-N-methyl-N-(2-pyrrolidin-1-yl-ethyl)-spiro[cyclohexane-1,1'-(3'H)-4'-azaisobenzofuran]-4-carboxamide;
trans-4'-methoxy-3'-oxo-N-methyl-N-(2-piperidin-1-yl-ethyl)-spiro[cyclohexane-1,1'-(3'H)-5'-azaisobenzofuran]-4-carboxamide;
trans-4'-methyl-3'-oxo-N-methyl-N-(2-piperidin-1-yl-ethyl)-spiro[cyclohexane-1,1'-(3'H)-5'-azaisobenzofuran]-4-carboxamide;
trans-4'-(1-methyl-1H-pyrazol-4-yl)-3'-oxo-N-methyl-N-(2-piperidin-1-ylethyl)-spiro[cyclohexane-1,1'-(3'H)-5'-azaisobenzofuran]-4-carboxamide; and
trans-5'-pyrazinyl-3'-oxo-N-methyl-N-(2-piperidin-1-yl-ethyl)-spiro[cyclohexane-1,1'-(3'H)-4'-azaisobenzofuran]-4-carboxamide;
or a pharmaceutically acceptable salt thereof.

3. A compound which is trans-5'-methoxy-3'-oxo-N-methyl-N-(2-piperidin-1-ylethyl)-spiro[cyclohexane-1,1'-(3'H)-4'-azaisobenzofuran]-4-carboxamide, or a pharmaceutically acceptable salt thereof.

4. A compound which is trans-5'-methoxy-3'-oxo-N-methyl-N-(2-piperidin-1-ylethyl)-spiro[cyclohexane-1,1'-(3'H)-4'-azaisobenzofuran]-4-carboxamide.

5. A compound which is trans-5'-methoxy-3'-oxo-N-methyl-N-(2-piperidin-1-ylethyl)-spiro[cyclohexane-1,1'-(3'H)-4'-azaisobenzofuran]-4-carboxamide in the form of a pharmaceutically acceptable salt thereof.

6. The compound of claim 2 which is trans-5'-methoxy-3'-oxo-N-methyl-N-(2-pyrrolidin-1-ylethyl)-spiro[cyclohexane-1, 1'-(3'H)-4'-azaisobenzofuran]-4-carboxamide, or a pharmaceutically acceptable salt thereof.

7. The compound of claim 2 which is trans-4'-methoxy-3'-oxo-N-methyl-N-(2-piperidin-1-ylethyl)-spiro[cyclohexane-1,1'-(3'H)-5'-azaisobenzofuran]-4-carboxamide, or a pharmaceutically acceptable salt thereof.

8. The compound of claim 2 which is trans-4'-methyl-3'-oxo-N-methyl-N-(2-piperidin-1-ylethyl)-spiro[cyclohexane-1,1'-(3'H)-5'-azaisobenzofuran]-4-carboxamide, or a pharmaceutically acceptable salt thereof.

9. The compound of claim 2 which is trans-4'-(1-methyl-1H-pyrazol-4-yl)-3'-oxo-N-methyl-N-(2-piperidin-1-yl-ethyl)-spiro[cyclohexane-1,1 '-(3 'H)-5'-azaisobenzofuran]-4-carboxamide, or a pharmaceutically acceptable salt thereof.

10. The compound of claim 2 which is trans-5'-pyrazinyl-3'-oxo-N-methyl-N-(2-piperidin-1-ylethyl)-spiro[cyclohexane-1,1'-(3'H)-4'-azaisobenzofuran]-4-carboxamide, or a pharmaceutically acceptable salt thereof.

11. A pharmaceutical composition which comprises a pharmaceutically-acceptable additive and a compound of claim 1 or a pharmaceutical acceptable salt thereof.

12. A pharmaceutical composition which comprises a pharmaceutically-acceptable additive and a compound of claim 2 or a pharmaceutical acceptable salt thereof.

13. A pharmaceutical composition which comprises a pharmaceutically-acceptable additive and the compound trans-5'-methoxy-3'-oxo-N-methyl-N-(2-piperidin-1-yl-ethyl)-spiro[cyclohexane-1,1'-(3'H)-4'-azaisobenzofuran]-4-carboxamide, or a pharmaceutically acceptable salt thereof.

14. A pharmaceutical composition which comprises a pharmaceutically-acceptable additive and trans-5'-methoxy-3'-oxo-N-methyl-N-(2-piperidin-1-ylethyl)-spiro[cyclohexane-1,1'-(3'H)-4'-azaisobenzofuran]-4-carboxamide.

15. A pharmaceutical composition which comprises a pharmaceutically-acceptable additive and trans-5'-methoxy-3'-oxo-N-methyl-N-(2-piperidin-1-ylethyl)-spiro[cyclohexane-1,1'-(3'H)-4'-azaisobenzofuran]-4-carboxamide in the form of a pharmaceutically acceptable salt thereof.

16. A pharmaceutical composition which comprises a pharmaceutically-acceptable additive and the compound of claim 6 or a pharmaceutical acceptable salt thereof.

17. A pharmaceutical composition which comprises a pharmaceutically-acceptable additive and the compound of claim 7 or a pharmaceutical acceptable salt thereof.

18. A pharmaceutical composition which comprises a pharmaceutically-acceptable additive and the compound of claim 8 or a pharmaceutical acceptable salt thereof.

19. A pharmaceutical composition which comprises a pharmaceutically-acceptable additive and the compound of claim 9 or a pharmaceutical acceptable salt thereof.

20. A pharmaceutical composition which comprises a pharmaceutically-acceptable additive and the compound of claim 10 or a pharmaceutical acceptable salt thereof.

* * * * *